US012644108B2

(12) United States Patent
Sheaffer et al.

(10) Patent No.: US 12,644,108 B2
(45) Date of Patent: Jun. 2, 2026

(54) PROCESS INTERMEDIATE IN THE PURIFICATION OF COLLAGENASE DRUG SUBSTANCES

(71) Applicant: Endo Ventures Ltd., Dublin (IE)

(72) Inventors: Christine A. Sheaffer, Doylestown, PA (US); Michael Berbaum, Pottstown, PA (US); John Hanna, East Norriton, PA (US); Jason Dziadosz, Quakertown, PA (US); Daniel Shanafelt, Red Hill, PA (US)

(73) Assignee: Endo Operations Limited, Dublin (IE)

( * ) Notice: Subject to any disclaimer, the term of this patent is extended or adjusted under 35 U.S.C. 154(b) by 84 days.

(21) Appl. No.: 18/169,480

(22) Filed: Feb. 15, 2023

(65) Prior Publication Data

US 2024/0110171 A1 Apr. 4, 2024

Related U.S. Application Data

(60) Continuation of application No. 17/559,782, filed on Dec. 22, 2021, which is a division of application No. 15/939,231, filed on Mar. 28, 2018, now Pat. No. 11,473,074.

(60) Provisional application No. 62/477,846, filed on Mar. 28, 2017.

(51) Int. Cl.
| *C12N 9/52* | (2006.01) |
| *A61K 31/00* | (2006.01) |
| *A61K 38/00* | (2006.01) |
| *G01N 33/569* | (2006.01) |

(52) U.S. Cl.
CPC ........ *C12N 9/52* (2013.01); *C12Y 304/24003* (2013.01); *A61K 31/00* (2013.01); *A61K 38/00* (2013.01); *G01N 33/56911* (2013.01)

(58) Field of Classification Search
None
See application file for complete search history.

(56) References Cited

U.S. PATENT DOCUMENTS

| 3,821,364 | A | | 6/1974 | Chiulli et al. |
| 4,338,000 | A | | 7/1982 | Kamimori et al. |
| 4,338,300 | A | | 7/1982 | Gelbard |
| 4,524,065 | A | | 6/1985 | Pinnell |
| 4,542,065 | A | | 9/1985 | Gaa |
| 4,645,668 | A | | 2/1987 | Pinnell |
| 4,732,758 | A | | 3/1988 | Hurion et al. |
| 5,252,461 | A | | 10/1993 | Weisbart |
| 5,252,481 | A | | 10/1993 | Holjevac et al. |
| 5,256,140 | A | | 10/1993 | Fallick |
| 5,332,503 | A | | 7/1994 | Lee et al. |
| 5,393,792 | A | | 2/1995 | Stern et al. |
| 5,422,103 | A | | 6/1995 | Stern et al. |
| 5,462,739 | A | | 10/1995 | Dan et al. |
| 5,514,340 | A | | 5/1996 | Lansdorp et al. |
| 5,514,370 | A | | 5/1996 | Stern et al. |
| 5,589,171 | A | | 12/1996 | Wegman |
| 5,705,170 | A | | 1/1998 | Kong et al. |
| 5,753,485 | A | | 5/1998 | Dwulet et al. |
| 5,753,785 | A | | 5/1998 | Reddy et al. |
| 5,830,741 | A | * | 11/1998 | Dwulet ................... C12N 9/52 |
| | | | | 435/220 |
| 5,952,215 | A | | 9/1999 | Dwulet et al. |
| 5,989,888 | A | | 11/1999 | Dwulet et al. |
| 6,022,539 | A | | 2/2000 | Wegman |
| 6,086,872 | A | | 7/2000 | Wegman |
| 6,086,877 | A | | 7/2000 | Nishioka et al. |
| 6,086,887 | A | | 7/2000 | Parrott |
| 6,146,626 | A | | 11/2000 | Markert et al. |
| 6,280,993 | B1 | | 8/2001 | Yamato et al. |
| 6,335,388 | B1 | | 1/2002 | Fotinos |
| 6,358,539 | B1 | | 3/2002 | Murad |
| 6,475,764 | B1 | | 11/2002 | Burtscher et al. |
| 6,953,583 | B1 | | 10/2005 | Ghisalberti |
| 6,958,150 | B2 | | 10/2005 | Wegman et al. |
| 7,083,964 | B2 | | 8/2006 | Kurfuerst et al. |
| RE39,941 | E | | 12/2007 | Wegman |
| 7,355,027 | B2 | | 4/2008 | Brehm et al. |
| 7,358,067 | B2 | | 4/2008 | Vrang et al. |
| 7,622,130 | B2 | | 11/2009 | Kolodney et al. |
| 7,811,560 | B2 | | 10/2010 | Sabatino et al. |
| 7,824,673 | B2 | | 11/2010 | Wegman et al. |
| 7,842,673 | B2 | | 11/2010 | Brink et al. |
| 7,854,929 | B2 | | 12/2010 | Badalemente et al. |
| 8,323,643 | B2 | | 12/2012 | Badalamente et al. |

(Continued)

FOREIGN PATENT DOCUMENTS

| AU | 2006206393 A1 | 7/2006 |
| BR | PI0607280-1 A2 | 8/2009 |
| CA | 2308842 A1 | 12/2000 |
| CA | 2643171 A1 | 9/2007 |
| CN | 1529751 A | 9/2004 |
| CN | 101684461 A | 3/2010 |
| EP | 0468411 A2 | 1/1992 |
| EP | 1433845 A1 | 6/2004 |
| EP | 2130551 | 12/2009 |
| EP | | |

(Continued)

OTHER PUBLICATIONS

Ji-Wei et al. (Appl. Microbiol. Biotech., 2011, vol. 92, pp. 253-262).*

(Continued)

*Primary Examiner* — Hope A Robinson
(74) *Attorney, Agent, or Firm* — BakerHostetler

(57) ABSTRACT

The present invention relates to the fields of collagenase production and collagenase products, and particularly to improving the reproducibility, purity, and stability of collagenase I and collagenase II compositions, where the compositions are pure to at least 95% by area as measured by reverse phase high pressure liquid chromatography (RP-HPLC) and essentially free of neutral protease.

11 Claims, 51 Drawing Sheets

Specification includes a Sequence Listing.

(56) References Cited

U.S. PATENT DOCUMENTS

| | | | |
|---|---|---|---|
| 8,380,531 B2 | 2/2013 | Paty et al. | |
| 9,757,435 B2 | 9/2017 | Herber | |
| 10,119,131 B2 | 11/2018 | Wegman et al. | |
| 10,123,959 B2 | 11/2018 | Badalamente et al. | |
| 10,603,365 B2 | 3/2020 | Herber | |
| 10,870,833 B2 * | 12/2020 | Goto | C12N 5/067 |
| 2002/0036328 A1 | 3/2002 | Richards et al. | |
| 2003/0022856 A1 | 1/2003 | Richardson et al. | |
| 2003/0026844 A1 | 2/2003 | Lee et al. | |
| 2003/0129178 A1 | 7/2003 | Wegman et al. | |
| 2004/0137596 A1 | 7/2004 | Kurfuerst et al. | |
| 2005/0227910 A1 | 10/2005 | Yang et al. | |
| 2005/0261584 A1 | 11/2005 | Eshel et al. | |
| 2005/0267080 A1 | 12/2005 | Kolodney et al. | |
| 2006/0020448 A1 | 1/2006 | Chelba et al. | |
| 2006/0204488 A1 | 9/2006 | Badalamente | |
| 2006/0241673 A1 | 10/2006 | Zadini et al. | |
| 2006/0251581 A1 | 11/2006 | Mcintyre et al. | |
| 2007/0003541 A1 | 1/2007 | Faudoa et al. | |
| 2007/0031482 A1 | 2/2007 | Castro et al. | |
| 2007/0224183 A1 | 9/2007 | Sabatino et al. | |
| 2007/0224184 A1 | 9/2007 | Badalemente et al. | |
| 2008/0020001 A1 | 1/2008 | Brehm et al. | |
| 2008/0206228 A1 | 8/2008 | Vaccaro et al. | |
| 2008/0233614 A1 | 9/2008 | Cranenburgh et al. | |
| 2008/0279900 A1 | 11/2008 | Longo et al. | |
| 2008/0300429 A1 | 12/2008 | Sakanishi et al. | |
| 2009/0053276 A1 | 2/2009 | Richard | |
| 2010/0015262 A1 | 1/2010 | Goralczyk et al. | |
| 2010/0021416 A1 | 1/2010 | Lichter et al. | |
| 2010/0035868 A1 | 2/2010 | Jabbour | |
| 2010/0086971 A1 | 4/2010 | Suppmann et al. | |
| 2010/0137747 A1 | 6/2010 | Thomas et al. | |
| 2010/0159564 A1 | 6/2010 | Dwulet et al. | |
| 2010/0233150 A1 | 9/2010 | Wegman et al. | |
| 2010/0233151 A1 | 9/2010 | Sabatino et al. | |
| 2010/0330065 A1 | 12/2010 | Sabatino et al. | |
| 2011/0070622 A1 | 3/2011 | Hoelke et al. | |
| 2011/0158972 A1 | 6/2011 | Sabatino et al. | |
| 2011/0160617 A9 | 6/2011 | Thomas et al. | |
| 2011/0189153 A1 | 8/2011 | Sabatino et al. | |
| 2011/0189163 A1 | 8/2011 | Sabatino et al. | |
| 2011/0217252 A1 | 9/2011 | Koverech | |
| 2011/0243908 A1 | 10/2011 | Sabatino et al. | |
| 2011/0243909 A1 | 10/2011 | Sabatino et al. | |
| 2011/0243919 A1 | 10/2011 | Sabatino et al. | |
| 2011/0243920 A1 | 10/2011 | Sabatino et al. | |
| 2011/0262508 A1 | 10/2011 | Watt et al. | |
| 2011/0294192 A1 | 12/2011 | Fukushima et al. | |
| 2012/0164131 A1 | 6/2012 | Huang et al. | |
| 2012/0237492 A1 | 9/2012 | Walker | |
| 2012/0237497 A1 | 9/2012 | Wegman et al. | |
| 2012/0315265 A1 | 12/2012 | Lai et al. | |
| 2013/0096596 A1 | 4/2013 | Schafer | |
| 2013/0129663 A1 | 5/2013 | Friberg et al. | |
| 2013/0195828 A1 | 8/2013 | Kibbe et al. | |
| 2013/0217789 A1 | 8/2013 | Taylor et al. | |
| 2013/0287759 A1 | 10/2013 | Ramon | |
| 2014/0004094 A1 | 1/2014 | Sabatino et al. | |
| 2014/0271508 A1 | 9/2014 | Florence et al. | |
| 2014/0271612 A1 | 9/2014 | Leppert et al. | |
| 2014/0335072 A1 | 11/2014 | Hart | |
| 2015/0010532 A1 | 1/2015 | Herber | |
| 2015/0301064 A1 | 10/2015 | Yoshida et al. | |
| 2016/0000890 A1 | 1/2016 | Yu et al. | |
| 2016/0279046 A1 | 9/2016 | Badalemente et al. | |
| 2017/0136039 A1 | 5/2017 | Jung et al. | |
| 2017/0209201 A1 | 7/2017 | Slayton et al. | |
| 2017/0228517 A1 | 8/2017 | Saliman et al. | |
| 2017/0290848 A1 | 10/2017 | Walker | |
| 2017/0319601 A1 | 11/2017 | Walker | |
| 2018/0327731 A1 * | 11/2018 | Sheaffer | C12N 9/52 |
| 2019/0240253 A1 | 8/2019 | Abst et al. | |
| 2022/0119791 A1 | 4/2022 | Sheaffer et al. | |
| 2024/0110171 A1 * | 4/2024 | Sheaffer | C12N 9/52 |

FOREIGN PATENT DOCUMENTS

| | | | | | |
|---|---|---|---|---|---|
| | | 2133415A1 | 12/2009 | | |
| EP | 2180002 A1 | 4/2010 | | | |
| EP | 2363461 A1 | 9/2011 | | | |
| FR | 2788682 A1 | 7/2000 | | | |
| IL | 192878 A | 3/2013 | | | |
| JP | 61-289885 A | 12/1986 | | | |
| JP | 03-091478 A | 4/1991 | | | |
| JP | 05-219942 A | 8/1993 | | | |
| JP | 06-237764 A | 8/1994 | | | |
| JP | 08-500970 A | 2/1996 | | | |
| JP | 09-508026 A | 8/1997 | | | |
| JP | 10-262658 A | 10/1998 | | | |
| JP | 11-501517 A | 2/1999 | | | |
| JP | 11-504225 A | 4/1999 | | | |
| JP | 2002-530873 A | 9/2002 | | | |
| JP | 2003-284553 A | 10/2003 | | | |
| JP | 2004-535197 A | 11/2004 | | | |
| JP | 2005-006552 A | 1/2005 | | | |
| JP | 2006-254876 A | 9/2006 | | | |
| JP | 2008-500970 A | 1/2008 | | | |
| JP | 2009-525283 A | 7/2009 | | | |
| JP | 2009-291195 A | 12/2009 | | | |
| JP | 2010-262658 A | 11/2010 | | | |
| JP | 2011-504225 A | 2/2011 | | | |
| JP | 2011-528716 A | 11/2011 | | | |
| JP | 5309289 B2 | 10/2013 | | | |
| JP | 2014-530873 A | 11/2014 | | | |
| JP | 2016-515521 A | 5/2016 | | | |
| JP | 6496386 B2 | 4/2019 | | | |
| JP | 7227918 B2 | 2/2023 | | | |
| KR | 10-2008-0093142 A | 10/2008 | | | |
| KR | 10-2009-0125705 A | 12/2009 | | | |
| KR | 10-2011-0046537 A | 5/2011 | | | |
| RU | 2180002 C2 | 2/2002 | | | |
| WO | 94/00580 A1 | 1/1994 | | | |
| WO | 94/16086 A1 | 7/1994 | | | |
| WO | WO-9417839 A1 * | 8/1994 | | A61L 26/0066 | |
| WO | 96/00283 A1 | 1/1996 | | | |
| WO | 96/28543 A1 | 9/1996 | | | |
| WO | 98/10079 A1 | 3/1998 | | | |
| WO | 98/24889 A1 | 6/1998 | | | |
| WO | 00/30182 A2 | 5/2000 | | | |
| WO | 01/21574 A1 | 3/2001 | | | |
| WO | 03/04628 A2 | 1/2003 | | | |
| WO | 2004/085643 A1 | 10/2004 | | | |
| WO | 2005/073367 A1 | 8/2005 | | | |
| WO | 2005/123764 A1 | 12/2005 | | | |
| WO | 2006/002646 A2 | 1/2006 | | | |
| WO | 2006/010057 A2 | 1/2006 | | | |
| WO | 2006/025226 A1 | 3/2006 | | | |
| WO | 2006/078870 A2 | 7/2006 | | | |
| WO | 2006/121968 A2 | 11/2006 | | | |
| WO | 2007/089851 A2 | 8/2007 | | | |
| WO | 2007/100590 A2 | 9/2007 | | | |
| WO | 2007/100675 A2 | 9/2007 | | | |
| WO | 2008/101406 A1 | 8/2008 | | | |
| WO | 2010/011605 A2 | 1/2010 | | | |
| WO | 2011/073925 A2 | 6/2011 | | | |
| WO | 2011/130537 A2 | 10/2011 | | | |
| WO | 2012/031245 A1 | 3/2012 | | | |
| WO | 2012/041512 A1 | 4/2012 | | | |
| WO | 2013/059619 A1 | 4/2013 | | | |
| WO | 2015/108901 A1 | 7/2015 | | | |
| WO | 2018/160905 A1 | 9/2018 | | | |
| WO | 2018/183582 A2 | 10/2018 | | | |

OTHER PUBLICATIONS

Staley, "Auxilium Pharmaceuticals Announces First Patients Dosed in Xiaflex Phase lb Cellulite Study;" Jan. 26, 2012; 1 page; downloaded from: https://www.benzinga.com/news/12/01/2291202/auxilium-pharmaceuticals-announces-first-patients-dosed-in-xiaflex-hase-ib-cellu.

Steinbrink et al., "Substrate Specificity of Beta-Collagenase from Clostridium histolyticum," The Journal of Biological Chemistry, 1985, vol. 260, pp. 2771-2776.

(56) References Cited

OTHER PUBLICATIONS

Stewart, "Uterine fibroids", The Lancet, 2001, vol. 357, pp. 293-298.

Strömberg et al., "Comparison of Treatment Outcome After Collagenase and Needle Fasciotomy for Dupuytren Contracture: A Randomized, Single-Blinded, Clinical Trial With a 1-Year Follow-Up", J Hand Surg Am., 2016, vol. 41, No. 9, pp. 873-880.

Strömberg et al., "Percutaneous Needle Fasciotomy Versus Collagenase Treatment for Dupuytren Contracture, A Randomized Controlled Trial with a Two-Year Follow-up", J Bone Joint Surg Am. 2018, vol. 100, pp. 1079-1086.

Successful Phase II Results Lead to Phase III Approval—Dupuytren's Disease, Internet Citation, retrieved Aug. 20, 2010, pp. 1-2 (2001).

Sugasawara et al., "Purification and Characterization of Three Forms of Collagenase from Clostridium histolytium," Entrez Pubmed abstract, 1984, vol. 23, pp. 5175-5181.

surgerynews.net, "Is this the End of Cellulite? Some Doctors Say, Fat Chance", 2005, pp. 1-3.

Takahashi et al., "New Culture Conditions for Clostridium histolyticum Leading to Production of Collagenase of High Specific Activity," J. Appl. Bact., 1972, vol. 35, pp. 647-657.

Takahashi, et al., "Elastolytic Activities of Clostridium histolyticum," Biochem. Biophys Res. Commun., 1970, vol. 39, No. 6, pp. 1058-1064.

Tay et al., "Comparison between Collagenase Injection and Partial Fasciectomy in the Treatment of Dupuytren's Contracture," Hand Surg. 2015, vol. 20, No. 3, pp. 386-390.

Taylor et al., "Putting the Moose on the Table: Understanding the Molecular Biology of Uterine Fibroids and Development of Non-invasion Treatment," XP055257658, 2012, pp. 1-64.

Taylor et al., "Recent scientific advances in leiomyoma (uterine fibroids) research facilitates better understanding and management," F1000Research, XP055257667, 2015, pp. 1-11.

Taylor et al., "Temperature-responsive biocompatibie copolymers incorporating hyperbranched polyglycerols for adjustable functionality", Journal of Functional Biomaterials 2011, vol. 2, pp. 173-194.

Taylor et al., "Treatment for Uterine Fibroids: Searching for Effective Drug Therapies," Drug Discovery Today Therapeutic Strategies, 2012, vol. 9, No. 1, pp. e41-e49, 2012.

TeensHealth, "Cellulite," TeensHealth.org, May 2009, pp. 1-2.

Thomas et. al., "The Emerging Role of Clostridium histolyticum Collagenase in the Treatment of Dupuytren Disease", Ther Clin Risk Manag., 2010, vol. 6, pp. 557-572.

Thorne et al., "Dynamic Reciprocity Between Cells and Their Microenvironment in Reproduction," Biology of Reproduction, 2014, vol. 92, No. 1, Article 25, pp. 1-10.

Tonkin, "Classification of Congenital Anomalies of the Hand and Upper Limb", J Hand Surg Am., 2015, vol. 40, No. 2, pp. 415-416.

Vos-Scheperkeuter et al., "Histochemical Analysis of the Role of Class I and Class II Clostridium Istochemical Analysis of the Role Histolyticum Collagenase in the Degradation of Rat Pancreatic Extracellular Matrix for Islet Isolation", Cell Transplantation, 1997, vol. 6, pp. 403-412.

Wanner et al., "An Evidence-Based Assessment of Treatments for Cellulite", J. Drugs Dermatol., 2008, vol. 7, No. 4, pp. 341-345.

Waters et al., "Collagenase Enzymatic Fasciotomy for Dupuytren Contracture in Patients on Chronic Immunosuppression", Am J Orthop (Belle Mead NJ), 2015, vol. 44, No. 11, pp. 518-521.

Welton et al., "Collagenase Production by Achromobacter lophagus," Biochimica et Biophysica Acta (BBA)—Enzymology, 1975, vol. 384, pp. 228-234.

Wetmore et al., "The Efficiency of Processing and Secretion of the Thermolysin-like Neutral Protease from Bacillus cereus Does Not Require the Whole Prosequence, But Does Depend on the Nature of the Amino Acid Sequence in the Region of the Cleavage Site", Mol. Microbiol., 1994, vol. 12, No. 5, pp. 747-759.

Why Choose Recombinant Enzymes New England Bio Labs, retrieved at https://international.neb.com/tools-and-resources/selection-charts/why-choose-recombinant-enzymes, retrieved on Mar. 2, 2022, pp. 1-7.

Wikipedia.org "Cellulite," http://en.wikipedia.org/wiki/cellulite, 2012, pp. 1-5.

Wolters et al., "Different Roles of Class I and Class II Clostridium Histolyticum Collagenase in Rat Pancreatic Islet isolation", Diabetes, 1995, vol. 44, pp. 227-233.

Xiaflex, "collagenase clostridium histolyticum", Prescribing Information, Malvern, PA: Endo Pharmaceuticals Inc., Revised Nov. 2019, pp. 1-43.

Yoshihara et al., "Cloning and Nucleotide Sequence Analysis of the colH Gene from Clostridium histolyticum Encoding a Collagenase and a Gelatinase", Journal of Bacteriology, 1994, vol. 176, No. 21, pp. 6489-6496.

Young et al., "Efficacy and safety of collagenase clostridium histolyticum for the treatment of edematous fibrosclerotic panniculopathy (cellulite)", Podium presented at the American Society of Plastic Surgeons Aesthetica 2017 Super Symposium, Mar. 2-4, 2017, pp. 1-4.

Zhou et al., "Collagenase Clostridium Histolyticum versus Limited Fasciectomy for Dupuytren's Contracture", Plast Reconstr Surg, 2015, vol. 136, No. 1, pp. 87-97.

"Basic Biochemistry Experiment, Department of Biology, Beijing Normal University, Higher Education Press", pp. 38-39, Feb. 1984.

BD Bionutrients Technical Manual: Advanced Processing, 3rd edition, Oct. 2006.

Kagedal et al.; "Chemical, physical and chromatographic properties of Superdex 75 prep grade and Superdex 200 prep grade gel filtration media;" Journal of Chromatography; vol. 537, 1991, pp. 17-32.

Liberase Research Grade Purified Enzyme Blends, Reference material A10, Roche Diagnostics GmbH, Aug. 2013, Version 06, pp. 1-18.

Protein Purification Handbook, Amersham Biosciences; 2001, 1-98.

Rhodes et al., "Determination of Protein Purity," Methods in Enzymology, vol. 463, 2009, pp. 677-689.

Sigma-Aldrich, "Product Information on Collagenase, High Purity", dated Sep. 13, 2018, pp. 1-6.

Hexsel et al., "Side-By-Side Comparison of Areas with and without Cellulite Depressions Using Magnetic Resonance Imaging," Dermatol. Surg. 2009, vol. 35, pp. 1471-1477.

High Performance Liquid Chromatography (HPLC) Tutorial, 2012, pp. 1-7.

Hiroshi et al., "Cloning a neutral protease of Clostridium histolyticum, determining its substrate specificity, and designing a specific substrate", Applied Microbiology and Biotechnology, Springer, DE, 2015, vol. 99, No. 24, pp. 10489-10499.

Hulstyn et al., "Adhesive capsulitis of the shoulder", Orthopaedic Review, 1993, pp. 425-433.

Hurst et al., "Injectable clostridial collagenase: striving toward nonoperative treatment options for fibroproliferative disorders," 2009, pp. 1-30, available at http://www.aaos.org/research/committee/research/Kappa/KD2009.sub.-Hurst.pdf.

Hurst et al., "Injectable Collagenase Clostridium Histolyticum for Dupuytren's Contracture", N Engl J Med. 2009, vol. 361, No. 10, pp. 968-979.

Hutchinson et al., "Dupuytren's Disease and Frozen Shoulder Induced by Treatment with a Matrix Metalloproteinase Inhibitor," The Journal of Bone and Joint Surgery, 1998, vol. 80B, No. 5 pp. 907-908.

Ibrahim-Grant et al., "Expression of PZ-Peptidases by Cultures of Several Pathogenic Fungi. Purification and Characterization of a Collagenase from Trichophyton Schoenleinii", Journal of Medical & Veterinary Mycology, 1996, vol. 34, pp. 83-90.

Imhof et al., "A Phase III Study of IncobotulinumtoxinA in the Treatment of Glabellar Frown Lines", J Clin Aesthet Dermatol, 2011, vol. 4, No. 10, pp. 28-34.

Information Related to ClinicalTrials.gov Identifier: NCT01518907, "The Safety, Effectiveness, and Pharmacokinetics of AA4500 for the Treatment of Edematous Fibrosclerotic Panniculopathy (Commonly Known as Cellulite)", pp. 1-9 first Posted: Jan. 26, 2012.

(56) References Cited

OTHER PUBLICATIONS

Ippolito et al., "Experimental Study on the Use of Collagenase in Localized Connective Tissue Fibrosis", Database EMBASE on STN., 1976, Acc. No. 1976196184, pp. 279-290.

Iwahashi et al., "Immunohistochemical analysis of collagen expression in uterine leiomyornata during the D menstrual cycle," Experimental and Therapeutic Medicine, 2011, vol. 2, pp. 287-290.

Jang et al., "The Anti-Wrinkle and Whitening Effect of Extracts of Castanea crenata Inner Shell," Journal of Life Science, 2011, vol. 21, No. 5, pp. 734-738.

Jayes et al., "Loss of stiffness in collangen-rich uterine fibroids after digestion with purified collagenase Clostridium histolyticum," American Journal of Obstetrics & Gynecology, 2016, vol. 1.e1, pp. 1-8.

Jin et al., "Reversibility of Experimental Rabbit Liver Cirrhosis by Portal Collagenase Administration", Laboratory Investigation, 2005, vol. 85, pp. 992-1002.

Jung et al., "Identification of Metal Ligands in the Clostridium histolyticum ColH Collagenase," J. of Bacteriology, 1999, vol. 181, No. 9, pp. 2816-2822.

Jung et al., "Expression of the colH gene encoding clostridium histolyticum collagenase in bacillus subtilis and its application to enzyme purification," Microbial. Immunol., 1996, vol. 40, No. 12, pp. 923-929.

Kaplan et al., "Predictors of recurrence for joints successfully treated with collagenase clostridium histolyticum injections", Podium presented at the 39th Annual Meeting of the American Society for Hand Therapists (ASHT), 2016, pp. 1-3.

Keil et al., "Some Newly Characterized Collagenases from Procaryotes and Lower Eucaryotes," Entrez Pubmed Abstract, 1979, vol. 23, pp. 87-108.

Kembhavi et al., "Clostripain: Characterization of the Active Site," FEBS Letters, 1991, vol. 283, Issue 2, pp. 277-280.

Khan et al., "Treatment of cellulite: Part I. Pathophysiology," J. Am. Acad. Dermatol., 2010, vol. 62, No. 3, pp. 361-370.

Kikuchi et al., "Intra articular injection of collagenase induces experimental osteoarthritis in mature rabbits", Osteoarthritis and Cartilage, 1998, vol. 6, pp. 177-186.

Kilian et al., "The frozen shoulder. 1-10 Arthroscopy, histological findings and transmission electron microscopy imaging", Der Chirurg; Zeitschrift Fur Alle Gebiete Der Operativen Medizen, 2001, vol. 72, No. 11, pp. 1303-1308.

Kirby et al., "Assessing cellulite severity: method for assessing reliability of a new clinician-reported and a new patient-reported photonumeric scale", Poster presented at the International Society of Pharmacoeconomics and Outcomes Research (ISPOR), 2018, 1 page.

Kooi et al., "Differentiation of Thermolysins and Serralysins by Monoclonal Antibodies", J. Med. Microbiol., 1996, vol. 45, pp. 219-225.

Kooi et al., "Identification of Neutralizing Epitopes on Pseudomonas aeruginosa Elastase and Effects of Cross-Reactions on Other Thermolysin-Like Proteases," Infection and Immunity, 1997, vol. 65, No. 2, pp. 472-477.

Krishna et al., "Immunogenicity to Biotherapeutics—The Role of Anti-Drug Immune Complexes", Frontiers in Immunology, 2016, vol. 7, Article 21, pp. 1-13.

Kurnik et al., "Buffer Exchange Using Size Exclusion Chromatography, Countercurrent Dialysis, and Tangential Flow Filtration: Models, Development and Industrial Application", Biotechnology and Bioengineering, 1995, vol. 45, pp. 149-157.

Kuwayama, "Enhancement of Homologous Recombination Efficiency by Homologous Oligonucleotides", Cell Interaction; Chapter 9, 2012, pp. 233-244.

Labrou et al., "The Structure-Function Relationship in the Clostripain Family of Peptidase," Eur. J. Biochem, 2004, vol. 271, pp. 983-992.

Lecroisey et al., "Purification, Stability and Inhibition of the Collagenase from Achromobacter lophagus", Febs Letters, 1975, vol. 59, No. 2, pp. 167-172.

Leppert et al., "Comparative ultrastructure of collagen fibrils in uterine leiomyomas and normal myometrium", Fertil Steril, 2004vol. 82, No. 3, pp. 1182-1187.

Leppert et al., "The Extracellular Matrix Contributes to Mechanotransduction in Uterine Fibroids", Hindawi Publishing Corporation, 2014, vol. 2014, Article ID 783289, pp. 1-12.

Lola et al., "Quantitative model of cellulite: Three-dimensional skin surface topography, biophysical characterization, and relationship to human perception", J. Cosmet. Set., 2005, vol. 56, pp. 105-120.

Lukac et al., "The Metalloenzymic Nature of Collagenase-Like Peptidase of the Rat Testis", J Reprod. Fert., 1977, vol. 49, pp. 95-99.

MacLennan, "The Histotoxic Clostridial Infections of Man," Bacteriol. Rev., 1962, vol. 26, pp. 177-274.

Madan, M., et al., "In situ forming polymeric drug delivery systems," Indian Journal of Pharmaceutical Sciences, vol. 71 (3), May-Jun. 2009, pp. 242-251.

Mandl et al., "Multiplicity of Clostridium histolyticum Collagenases", Biochemistry, 1964, vol. 3, pp. 1737-1741.

Matsushita et al., "Gene Duplication and Multiplicity of Collagenases in Clostridium histolyticum," J. of Bacteriology, 1999, vol. 181, No. 3, pp. 923-933.

McLane et al., "Analysis of potential impact of healthcare provider gender on rating cellulite severity", The American Society of Plastic Surgeons (ASPS) Aesthetica, 2018, pp. 1-3.

McLane et al., "Assessing Cellulite Severity: Test-Retest Reliability of and Concordanance Between New Clinician Reported and Patient Reported Photonumeric Scales", The American Society of Plastic Surgeons (ASPS) 97th Annual Meeting, 2018, pp. 1-3.

McMahon et al., "Pharmacokinetics, Clinical Efficacy, Safety Profile, and Patient-Reported Outcomes in Patients Receiving Subcutaneous Testosterone Pellets 900 mg for Treatment of Symptoms Associated With Androgen Deficiency", J Sex Med., 2017, vol. 14, No. 7, pp. 883-890.

MedlinePlus "Cellulite," http://www.nlm.nih.gov/medlineplus/encv/article/002033.htm, updated Oct. 10, 2010, pp. 1-2.

Melton-Witt et al., "Identification of Functional Domains of Clostridium septicum Alpha Toxin," Biochem., 2006, vol. 45, No. 48, pp. 14347-14354.

Muppavarapu et al., "Clinical outcomes following collagenase injections compared to fasciectomy in the treatment of Dupuytren's contracture," Hand, 2015, vol. 10, No. 2, pp. 260-265.

Naam NH. "Functional outcome of collagenase injections compared with fasciectomy in treatment of Dupuytren's contracture", Hand, 2013, vol. 8, No. 4, pp. 410-416.

Narins et al., "A randomized, double-blind, multicenter comparison of the efficacy and tolerability of restylane versus zyplast for the correction of nasolabial folds", Dermatol Surg, 2003, vol. 29, No. 6, pp. 588-595.

National Library of Medicine "MeSH Descriptor Data—Hyaluronoglucosaminidase," http://www.nlm.nih.gov/cgi/mesh/2008/MB_cgi?mode=&term=hyaluronidase, 1 page, 2008.

Newsday Article—"Promising New Treatments For Stiff-Shoulder Condition", published on Oct. 2, 2001, p. 1.

The Declaration of Thomas Wegman and Bo Yu Dated Mar. 13, 2013 and Filed in U.S. Appl. No. 13/713,019.

Akers, "Excipient-Drug Interactions in Parenteral Formulations," J. Pharm. Sci., 2002, vol. 91, No. 11, pp. 2283-2300.

Almeida et al., "Intra- and inter-observer reliability of the application of the cellulite severity scale to a Spanish female population : CSS reliability in a Spanish female population", Jeadv. Journal of the european academy of dermatology and venereology., vol. 27, No. 6, Apr. 6, 2012, pp. 694-698.

Angleton et al., "Preparation and Reconstitution with Divalent Metal Ions of Class I and Class II Clostridium Histolyticum Apocollagenases," Biochemistry, 1988, vol. 27, pp. 7406-7412.

Anonymous: "Stony Brook Announces New Clinical Trial with BioSpecifics Injectable Collagenase for Adhesive Capsulitis," (Oct. 2000); Retrieved from the Internet Oct. 12, 2015, pp. 1-3.

Apostol et al., "Uncertainty Estimates of Purity Measurements Based on Current Information: Toward a "Live Validation" of Purity Methods", Pharm Res, 2012, pp. 1-16.

(56)            References Cited

OTHER PUBLICATIONS

Assessment Report, Xiapex, Common name: Collagenase clostridium histolyticum, Procedure No. EMEA/H/C/2048, 2011, pp. 1-71.

Atroshi et al., "Costs for collagenase injections compared with fasciectomy in the treatment of Dupuytren's contracture: a retrospective cohort study," BMJ Open. 2014, vol. 4, No. 1:e004166, pp. 1-7.

Avram, "Cellulite: a review of its physiology and treatment," J Cosmet Laser Ther., 2004, vol. 6, No. 4, pp. 181-185.

Badalamente et al., "Collagen as a clinical target: Nonoperative treatment of dupuytren's disease" The Journal of Hand Surgery, W.B. Saunders, 2002, vol. 27, No. 5, pp. 788-798.

Badalamente et al., "Efficacy and Safety of Injectable Mixed Collagenase Subtypes in the Treatment of Dupuytren's Contracture", The J. of Hand Surgery, 2007, vol. 32A, No. 06, pp. 767-774.

Badalamente et al., "Enzyme injection as a nonoperative treatment for Dupuytren's disease", Drug Delivery, 1996, vol. 3, pp. 35-40.

Badalamente et al., "Enzyme Injection as Nonsurgical Treatment of Dupuytren's Disease," The Journal of Hand Surgery, 2000, vol. 25A, No. 4, pp. 629-636.

Bains et al., "Primary frozen shoulder, The untold story!", Journal of Bone and Joint Surgery, 2006, vol. 90-B, Supp. sub.-II, 1 page.

Balci et al., "Shoulder Adhesive Capsulitis and shoulder range of motion in Type II Diabetes Mellitus: association with diabetic complications", Journal of Diabetes and its Complications, Elsevier Science, New York, 1999, vol. 13, pp. 135-140.

Ballard et al., "Purification and Characterization of the Lethal Toxin (Alpha-Toxin) of Clostridium septicum," Infection and Immunity, 1990, vol. 60, No. 3 pp. 784-790.

Bauer et al., "Non-contact thermal imaging as potential tool for personalized diagnosis and prevention of cellulite", Journal of Thermal Analysis and Calorimetry, 2018, vol. 133, pp. 571-578.

BD BioPharmaceutical Production, "Bionutrient Technical Manual", Second Eddition, Mar. 2004, pp. 1-13.

Bear et. al., "Treatment of Recurrent Dupuytren Contracture in Joints Previously Effectively Treated with Collagenase Clostridium Histolyticum", J Hand Surg Am., 2017, vol. 42, No. 5, pp. 391.e1-391.e8.

Behera et al., "Thrombospondin-1 and Thrombospondin-2 mRNA and TSP-1 and TSP-2 Protein Expression in Uterine Fibroids and Correlation to the Genes COL1A1 and COL3A1 and to the Collagen Cross-link Hydroxyproline," Reproductive Sciences., 2007, vol. 14, No. 8S, pp. 63-76.

Bielfeldt et al., "Non-invasive evaluation techniques to quantify the efficacy of cosmetic anti-cellulite products", Skin Research and Technology 2008, vol. 14, pp. 336-346.

Billington et al., "Thiol-Activated Cytolysins: Structure, Function and Role in Pathogenesis," FEMS Microbiol. Lett., 2000, vol. 182, No. 2, pp. 197-205.

Bio-Rad, "Chromatography Column Performance and Data Analysis Success Guide", Jun. 2014, pp. 1-17.

Bond et al., "Characterization of the Individual Collagenases from Clostridium Histolyticum", Biochemistry, 1984, vol. 23, pp. 3085-3091.

Bond et al., "Purification and separation of individual collagenases of clostridium histolyticum using red dye ligand chromatography," Biochemistry 1984, vol. 23, pp. 3077-3085.

Bonnerjea et al., "Protein purification: the right step at the right time;" Biotechnology, 1986, vol. 4, pp. 954-958.

Bowen, "A Comparison of the Lethal and Hemolytic Toxins of Clostridium Histolyticum," Yale J. Biol. Med., 1952, vol. 25, No. 2, pp. 124-138.

Brandhorst et al., "Adjustment of the Ratio Between Collagenase Class II and I Improves Islet Isolation Outcome," Transplantation Proceedings, 2005, 37, 3450-3451.

Brandhorst et al., "The ratio between collagenase class I and class II influences the efficient islet release from the rat pancreas", Transplantation, 2008, vol. 85, No. 3, pp. 456, 457.

Brandt et al., "Safety and Effectiveness of Small and Large Gel-Particle Hyaluronic Acid in the Correction of Perioral Wrinkles", J Drugs Dermatol., 2011, vol. 10, No. 9, pp. 982-987.

Brunengraber et al., "Injectable Clostridium Histolyticum Collagenase as a Potential Treatment for Uterine Fibroids", Reproductive Sciences, 2014, vol. 21, No. 12, pp. 1452-1459.

Buhren et al., "Hyaluronidase: From Clinical Applications to Molecular and Cellular Mechanisms," Eur. J. Med. Res. 2016, vol. 21, No. 5, pp. 1-8.

Bunker et al., "The pathology of frozen shoulder. A Dupuytren-like disease", The Journal of Bone and Joint Surgery.British vol. Sep. 1995, vol. 77, No. 5, pp. 677-683.

Bunker, "Frozen shoulder: unravelling the enigma", Ann R Coll Surg Engl, 1997, vol. 79, pp. 210-213.

Callaghan III et al., "Cellulite: a review of pathogenesis-directed therapy", Seminars in Cutaneous Medicine and Surgery, Dec. 2017, vol. 36, pp. 179-184.

Camper et al., "Cost per episode of care with collagenase clostridium histolyticum versus fasciectomy for Dupuytren's contracture: a real-world claims database analysis", Poster presented at the Annual Academy of Managed Care Pharmacy Nexus (AMCP Nexus), Oct. 16-19, 2017, pp. 57-64.

Casabona et al., "Microfocused Ultrasound with Visualization and Calcium Hydroxlapatite for Improving Skin Laxity and Cellulite Appearance," PRS Global Open, 2017, pp. 1-8.

Center for Drug Evaluation and Research; Application No. 206330Orig1s000; Other Review(S); PMR/PMC Development Template; https://www.accessdata.fda.gov/drugsatfda_docs/nda/2015/206333Orig1s000OtherR.pdf; Last Updated Apr. 27, 2015, pp. 1-140.

Center Watch Staff, "BioSpecifics Technologies announces positivedata from phase lib cellulite study" Nov. 21, 2016, pp. 1-2.

Chen et al., "Clinicopathological Study on Submucosal Injection of Collagenase in the Treatment of Submucous Fibrosis in the Oral Cavity", The Kaohsiung Journal of Medical Sciences, 1986, vol. 2, No. 3, pp. 212-219.

Citation of Prior Art and Statements Under 35 U.S.C. 301 dated Dec. 23, 2019, pp. 1-17.

Collagenase—Worthington Enzyme Manual, available at http://www.worthington-biochem.com/cls/default.html; downloaded from internet on Dec. 1, 2020; pp. 1-4.

Collagenase, From Clostridium histolyticum; Roche Diagnostics GmbH, Jul. 2005, pp. 1-2.

Coons et al., "Recommendations on Evidence Needed to Support Measurement Equivalence between Electronic and Paper-Based Patient-Reported Outcome (PRO) Measures", ISPOR ePRO Good Research Practices Task Force Report, Value in Health, 2009, vol. 12, pp. 419-429.

Costas et al., "A randomized phase 2A, double-blind, placebo-controlled, dose-ranging study to evaluate the safety and effectiveness of collagenase clostridium histolyticum (cch) in the treatment of Dupuytren disease nodules", Podium presented at the 71st Annual Meeting of the American Society for Surgery of the Hand (ASSH), 2016, pp. 1-2.

Costas, B., et al., "Efficacy and safety of collagenase clostridium histolyticum for Dupuytren disease nodules: a randomized controlled trial", BMC Musculoskelet Disord. Aug. 30, 2017;18(1):374.

Court Decision dated Aug. 11, 2017 in Korean Appeal Suit case for Korean Patent Application No. 10-2011-7006197, pp. 1-15.

Cuggino et al., "Synthesis, characterization and slow drug delivery of hydrogels based in N-acryloyl-tris-(hydroxymethyl) aminomethane and N-isopropyl acrylamide", Reactive & Functional Polymers, 2011, vol. 71, pp. 440-446.

Dargatz et al., "The Heterodimeric Protease Clostripain from Clostridium Histolyticum is Encoded by a Single Gene," Mol. Gen. Genet., 1993, vol. 240, pp. 140-145.

Declaration of Dr. Dagum dated Sep. 4, 2017: "Curriculum Vitae of Alexander B. Dagum, M.D", pp. 1-19.

Nguyen et al., "Injectable biodegradable hydrogels," Macromol. Biosci., 2010, vol. 10, pp. 563-579.

Nielsen et al., "Prediction of Signal Peptides and Signal Anchors by a Hidden Markov Model," AAAI Press, 1998, pp. 122-130.

(56)　　　　　References Cited

OTHER PUBLICATIONS

Norian et al., "Characterization of tissue biomechanics and mechanical signaling in uterine leiomyoma," Matrix Biol., 2011, vol. 31, No. 1, pp. 57-65.
Nydick et al., "A comparison of percutaneous needle fasciotomy and collagenase injection for dupuytren disease", J Hand Surg Am., 2013, vol. 38, No. 12, pp. 2377-2380.
O'Donohue et al., "Cloning and Expression in Bacillus subtilis of the NPR Gene from Bacillus thermoproteolyticus Rokko Coding for the Thermostable Metalloprotease Thermolysin", Biochem. J., 1994, vol. 300, pp. 599-603.
O'Donohue et al., "The Roles of the Prosequence of Thermolysin in Enzyme Inhibition and Folding in Vitro," J. Biol. Chem., 1996, vol. 271, No. 43, pp. 26477-26481.
obgyn.net Headline News, Successful phase II results lead to phase III approval-Dupuytren disease. Posted at the web on Oct. 8, 2001, (at the web: http://www.obgyn.net/newsrx/g eneral_h ealth-dupuytren_ disease-20011008-21.asp), especially pp. 1-2, last paragraph.
Omi et al., "Ultrastructural Assessment of Cellulite Morphology: Clues to a Therapeutic Strategy?" Laser Therapy, 2013, vol. 22, No. 2, pp. 131-136.
Oppenheim et al., "A modified procedure for the purification of clostridial collagenase", Preparative Biochemistry and Biotechnology, 1978, vol. 8, No. 5, pp. 387-407.
Pall BioPharmaceuticals, "Mustang Q Capsule: The Only Disposable Process Chromatography Column for Pharmaceutical Manufacturing", Pharmaceutical Online, 2000, 1 page.
Peavey et al., "Collagen-Binding .alpha. II Integrin Expression in Human Myometrium and Fibroids Utilizing a Novel RNA in Situ Probe," Reproductive Sciences, 2014, vol. 21, No. 9, pp. 1139-1144.
Peimer et al., "Dupuytren contracture recurrence following treatment with collagenase clostridium histolyticum (CORDLESS [Collagenase Option for Reduction of Dupuytren Long-Term Evaluation of Safety Study]): 5-year data", J Hand Surg Am., 2015, vol. 40, No. 8, pp. 1597-1605.
Povlsen et al., "What is the better treatment for single digit dupuytren's contracture: surgical release or collagenase clostridium histolyticum (Xiapex) injection?," Hand Surg, 2014 vol. 19, No. 3, pp. 389-392.
Press Release, "Auxilium Pharmaceuticals, Inc. Announces First Patients Dosed in Xiaflex Phase IB Cellulite Study", Exhibit-5, Jan. 26, 2012; pp. 1-7; downloaded from: https://www.pmewswire.com/news-releases/auxilium-pharmaceuticals-inc-announces-first-patients-dosed-in-xiaflex-phase-ib-cellulite-study-138113223.html.
Press Release, "Auxilium Pharmaceuticals, Inc. Announces First Patients Dosed in Xiaflex Phase lb Cellulite Study", Exhibit-1, Jan. 26, 2011; pp. 1-4; downloaded from: https://www.sec.gov/Archives/edgar/data/1182129/000119312512024205/d290313dex991.htm.
Press Releases, "Endo Announces Positive Results from Phase 3 Studies of Collagenase Clostridium Histolyticum (CCH) in Patients with Cellulite", Exhibit-2, 2018, pp. 1-3.
Priestley et al., "Converting from Transdermal to Buccal Formulations of Buprenorphine: A Pharmacokinetic Meta-Model Simulation in Healthy Volunteers", Pain Med., 2018, vol. 19, No. 10, pp. 1988-1996.
Proprietary Product Name: Xiaflex, "Australian Public Assessment Report for Collagenase clostridium histolyticum", Australian Government, Department of Health, Therapeutic Goods Administration, Sponsor: Actelion Pharmaceuticals Australia Pty Ltd, Nov. 2013, pp. 1-83.
Protein I—Separation, Purification, and Property-, edited by Japan Biochemical Society, 1st Edition, 1st Issue, published by Tokyo Kagaku Dojin, Feb. 26, 1990, pp. 161-169.
Q6A Specifications, "Test procedures and acceptance guidance criteria for new drug substances and new drug products", Chemical Substances, 2000, vol. 65, No. 251, pp. 83041-83063.
Queiroz et al, "Hydrophobic Interaction Chromatography of Proteins", Journal of Biotechnology, 2001, vol. 87, pp. 143-159.

Querleux et al, "Anatomy and physiology of subcutaneous adipose tissue by in vivo magnetic resonance imaging and spectroscopy: relationships with sex and presence of cellulite", Skin Res Technol., 2002, vol. 8, No. 2, pp. 118-124.
Ralph et al., "Collagenase clostridium histolyticum in combination with vacuum therapy in patients with Peyronie's disease", Podium presented at the 22nd Annual Fall Scientific Meeting of the Sexual Medicine Society of North America (SMSNA); Nov. 3-6, 2016; Scottsdale, AZ, 1 page.
Ralph et al., "The safety and efficacy of collagenase clostridium histolyticum (CCH) in combination with vacuum therapy for the treatment of Peyronie's disease", 2017, vol. 14, pp. 1430-1437.
Ralph et al., "The safety and efficacy of collagenase clostridium histolyticum in combination with vacuum therapy for the treatment of Peyronie's disease", Podium presented at the 112th Annual Meeting of the American Urological Association (AUA), May 12-16, 2017, 1 page.
Ralph et. al., "Treatment of Peyronie's Disease With Collagenase Clostridium histolyticum and Vacuum Therapy: A Randomized, Open-Label Pilot Study", J Sex Med. 2017, vol. 14, No. 11, pp. 1430-1437.
Roche Applied Science, The Complete Guide for Protease Inhibition, 2004, pp. 1-12.
Rogers et al., "Mechanical homeostasis is altered in uterine leiomyoma," Am. J. Obstet. Gynecol., 2008, vol. 198, No. 4, pp. 474.e1-474.11.
Rotunda et al., "Mesotherapy and phosphatidycholine injections: historical clarification and review", Dematologic Surgery: Official Publication for American Society for Dermatologic Surgery, 2006, vol. 32, No. 4, pp. 465-480.
Sadick et al., "Collagenase Clostridium Histolyticum for the Treatment of Edematous Fibrosclerotic Panniculopathy (Cellulite): A Randomized Trial", Dermatol Surg., 2019 vol. 45, pp. 1047-1056.
Sadick et al., Comparisons of Clinical Reported and Patient Reported Cellulite Severity Scales With Existing Scales for Measurement of Cellulite Severity, Maui Derm 2018, pp. 1-33.
Sadick et al., "Comparisons of Clinician Reported and Patient Reported Cellulite Severity Scales With Existing Scales for Measurement of Cellulite Severity", Poster presented at the 2017 American Society for Dermatologic Surgery Annual Meeting (ASDS), 2017; Chicago, IL, 1 page.
Sadick et al., "Efficacy and Safety Evaluation of Collagenase Clostridium Histolyticum for the Treatment of Edematous Fibrosclerotic Panniculopathy", Poster presented at the Maui Derm for Dermatologist, Jan. 28-Feb. 1, 2018; Maui, HI, 1 page.
Sadick, "New measurement and treatment options for edematous fibrosclerotic panniculopathy (cellulite): results from a randomized, double-blind, placebo-controlled trial of CCH", Podium presented by Dr. John Joseph at the Vegas Cosemetic Surgery (VCS); Jun. 6-10, 2018, NV, pp. 1-2.
Sasaki, "Single Treatment of Grades II and III Cellulite Using a Minimally Invasive 1,440-nm Pulsed Nd:YAG Laser and Side-Firing Fiber: an Institutional Review Board-Approved Study witha 24-Month Follow-Up Period", published on Oct. 11, 2013, vol. 37, pp. 1073-1089.
Scherman et al., "One-year results of needle fasciotomy and collagenase injection in treatment of Dupuytren's contracture: A two-centre prospective randomized clinical trial,"J Hand Surg Eur, 2016, vol. 41, No. 6, pp. 577-582.
Serefoglu et.al., "Factors Associated With Erectile Dysfunction and the Peyronie's Disease Questionnaire in Patients With Peyronie Disease", Urology, 2017, vol. 107, pp. 155-160.
Shimada et al., "C-terminal Amino Acid Residues are Required for the Folding and Cholesterol Binding Property of Perfringolysin O, a Pore-forming Cytolysin," The Journal of Biological Chemistry, 1999, vol. 274, No. 26, pp. 18536-18542.
Siegel et al., "Adhesive Capsulitis: A Sticky Issue", American Family Physician, 1999, vol. 59, No. 7, pp. 1843-1852.
Sigma Aldrich, "Collagenase Guide", 2005, pp. 1-4.
Skov et al., "Injectable Collagenase Versus Percutaneous Needle Fasciotomy for Dupuytren Contracture in Proximal Interphalangeal Joints: A Randomized Controlled Trial", J Hand Surg Am., 2017, vol. 42, No. 5, pp. 321-328.

(56)  References Cited

OTHER PUBLICATIONS

Smalls, "Development of Quantitative Modes for the Investigation of Gynoid Lipodystrophy (Cellulite)", Ph.D. Thesis, University of Cincinnati, Apr. 21, 2005, pp. 1-210.

Smalls, "Effect of Weight Loss on Cellulite: Gynoid Lypodystrophy", Plast. Reconstr. Surg., 2006, vol. 118, No. 2, pp. 510-516.

Smith et al., "A multicenter, double-blind, placebo-controlled trial of autologous fibroblast therapy (Azficel-T) for the treatment of nasolabial fold wrinkles", Dermatol Surg., 2012, vol. 38, No. 7, pp. 1234-1243.

Soledad et al., "Mechanical Signaling in Reproductive Tissues: Mechanisms and Importance," Reproductive Sciences, 2014, vol. 21, No. 9, pp. 1093-1107.

Specific Activity—https://terms.naver.com/entry.nhn?docId=1913800 &cid=50314&categoryId=50314, dated Jun. 10, 2017, pp. 1-3.

Specific Activity—Reference Material—Korean Appeal Suit case for Korean Patent Application No. 10-2011-7006197, 2017, pp. 1-3.

Staby et al., "Comparison of Chromatographic Ion-Exchange Resins. II. More Strong Anion-Exchange Resins," Journal of Chromatography A, 2001, vol. 908, pp. 149-161.

Cawston et al., Mammalian Collagenases, Biochem. Biophys. Acta, 455, 1976:711-722.

Jovanovic et al., The Influence of Metal Salts, Surfactants, and Wound Care Products on Enzymatic Activity of Collagenase, the Would Debriding Enzyme, 2012, 24(9): 242-253.

Wu et al., "Purification and Characterization of a Novel Collagenase from Bacillus Pumilus Col..J", Appl Biochem Biotech., 2010, 160:129-139.

U.S. Appl. No. 17/559,782, filed Dec. 22, 2021.

U.S. Appl. No. 15/939,231, filed Mar. 28, 2018.

Declaration of Dr. Michael Mclane: "Auxilium Drug Shipment Request Form for Domestic Studies regarding Protocol No. AUX-CC-830," 2011.

Declaration of Dr. Susan G. Emeigh Hart: "Assignment Recorded with the USPTO on Aug. 17, 2016 at Reel 039466 Frame 0337".

Declaration of inventor Benjamin Del Tito, Jr. dated Feb. 7, 2010 and filed in U.S. Appl. No. 11/699,302.

Demidyuk et al., "Structural Organization of Precursors of Thermolysin-like Proteinases," Protein J., 2008, vol. 27, pp. 343-354.

Denkler et al., "Evidence-Based Medicine: Options for Dupuytren's Contracture: Incise, Excise, and Dissolve," Plastic and Reconstructive Surgery, 2016, vol. 139, No. 1, pp. 240e-255e.

Dhaneshwar et al., "Dextran: A promising macromolecular drug carrier," Indian Journal of Pharmaceutical Sciences, 2006, pp. 705-714.

Difeo and BBL Manual, "Manual of Microbiological Culture Media", 2003, pp. 458-460.

Dimarcantonio, "Multiple Collagenase Injections Effective, Safe for Treating Frozen Shoulder", OrthoSuper Site, 2008, Retrieved from the Internet: http://www.orthosupersite.com/view.aspx?rid= 16738#jump, retrieved on Nov. 8, 2011, pp. 1-2.

Divino et al., "Total cost of care associated with collagenase clostridium histolyticum versus fasciectomy for the treatment of Dupuytren's contracture: a retrospective cohort analysis", American Association for Hand Surgery (AAHS) Annual Meeting, 2018, pp. 1-3.

Draelos, "The disease of cellulite", Journal of Cosmetic Dermatology, vol. 4, Issue 4, First Published Dec. 5, 2005, pp. 1-3.

Ducka et al., "A Universal Strategy for High-Yield Production of Soluble and Functional Clostridial Collagenases in E. coli," Appl. Microbiol Biotechnol, 2009, vol. 83, pp. 1055-1065.

Eckhard et al., "Structural Basis for Activity Regulation and Substrate Preference of Clostridial Collagenases G, H, and T", J. Biol. Chem., vol. 288, No. 28, Jul. 12, 2013, pp. 20184-20194.

Edkins et al., "Assessment of Potential Cross-Reactivity of Human Endogenous Matrix Metalloproteinases With Collagenase Clostridium Histolyticum Antibodies in Human Sera Obtained From Patients With Dupuytren's Contracture", Clinical and Vaccine Immunology, 2012, vol. 19, No. 4, pp. 562-569.

EMBL, "Protein Expression and Purification Core Facility", Cloning Choice of Expression Systems, 2002, pp. 1-4.

Eoanna Bauer, "Endo Announces Positive Data from Phase 2b Study of Collagenase Clostridium Histolyticum (CCH) in Patients with Cellulite", Endo International plc, 2016, pp. 1-4.

Eschbach et al., "Improved Erythrocyte Lysis Assay in Microtitre Plates for Sensitive Detection and Efficient Measurements of Hemolytic Compounds from Ichthyotoxic Algae", Journal of Applied Toxicology, 2001, vol. 21, pp. 513-519.

Evans, "The lanthanide-enhanced affinity chromatography of clostridial collagenase", Biochem J, 1985, vol. 225, No. 2, pp. 553-556.

Food and Drug Administration, "Guidance for Industry on Patient-Reported Outcome Measures: Use in Medical Product Development to Support Labeling Claims", Availability Use in Medical Product Development to Support Labeling claims, Federal Register, 2009, vol. 74, No. 235, pp. 65132-65133.

Friedman et al. "Degradation of porcine dermal connective tissue by collagenase and hyaluronidase," British Journal of Dermatology, 1986, vol. 115, pp. 403-408.

Friedmann et al., "Cellulite: a Review with a Focus on Subcision," Clin Cosmet Investig Dermatol, 2017, vol. 10, pp. 17-23.

Frigerio et al., "Model Building of a Thermolysin-Like Protease by Mutagenesis," Protein Eng., 1997, vol. 10, No. 3, pp. 223-230.

Galardy et al., "Inhibition of Collagenase from Clostridium histolyticum by Phosphoric and Phosphonic Amides," Biochemistry, 1983, vol. 22, pp. 4556-4561.

Gaston et al., "The Efficacy and Safety of Concurrent Collagenase Clostridium Histolyticum Injections for 2 Dupuytren Contractures in the Same Hand: a Prospective, Multicenter study", J Hand Surg Am. 2015, vol. 40, No. 10, pp. 1963-1971.

Gelbard et al., "Collagenase Versus Placebo in the Treatment of Peyronie's Disease: A Double-Blind Study", The Journal of Urology, 1993, vol. 1489, pp. 56-58.

Gelbard et al., "The Use of Collagenase in the Treatment of Peyronie's Disease", The Journal of Urology, 1985, vol. 134, pp. 280-283.

GenBank Database accession No. D29981, "Clostridium Histolyticum colH gene for collagenase, complete cds", Retreived from https://www.ncbi.nlm.nih.gov/nuccore/D29981, 2003, pp. 1-2.

GenBank Database accession No. D87125, "Ascaris Suum mRNA for ASABF-delta, complete cds", Retrieved from https://www.ncbi.nlm.nih.gov/nuccore/D87125, 2003, pp. 1-1.

GenBank Database accession No. D87215, "Clostridium histolyticum orfluG, colG, mscL, orf2dG, orf3dG genes, complete cds", Retrieved from https://www.ncbi.nlm.nih.gov/nuccore/D87215, 2007, pp. 1-3.

GenBank Database accession No. X63673, "C.histolyticum closl gene for alpha-clostripain", Retrieved from https://www.ncbi.nlm.nih.gov/nuccore/X63673, 1993, pp. 1-2.

GenBank Under Accession No. CAA54291; Retrieved from: https://www.ncbi.nlm.nih.gov/protein/CAA54291; Retrieved on: May 19, 2023.

Gill et al., "Does needle size matter?," Journal of Diabetes Science and Technology, 2007, vol. 1, No. 5, pp. 725-729.

Gilpin et al., "Injectable collagenase clostridium histolyticum: a new nonsurgical treatment for Dupuytren's disease,"J Hand Surg Am, 2010, vol. 35, No. 12, pp. 2027-2038.

Giudicelli et al. "Influence of trypsin on lipolysis in human fat cells comparison with rat adipocytes," Biochimica et Biophysica Acta, 1976, vol. 450, Issue 3, pp. 358-366.

Goldman et al., "Cellulite: A New Treatment Approach Combining Subdermal Nd: YAG Laser Lipolysis and Autologous Fat Transplantation", Aesthetic Surg J., 2008, vol. 28, pp. 656-662.

Goldstein et al., "Baseline severity of Peyronie's Disease Symptoms Predicts Improved Female Partner Burden Scores After Treatment with Collagenase Clostridium Histolyticum", Moderated poster presented at the Sexual Medicine Society of North America (SMSNA): Oct. 26-29, 2017: San Antonio, TX, pp. 1-6.

Goldstein et al., "Impact of Collagenase Clostridium Histolyticum Treatment of Men With Peyronie's Disease on Improvement of Female Partner Sexual Function", AUA, 2018, p. 1.

(56) References Cited

OTHER PUBLICATIONS

Goldstein et al., "Changes in the Effects of Peyronie's Disease After Treatment With Collagenase Clostridium histolyticum: Male Patients and Their Female Partners", Sex Med., 2017, vol. 5, No. 2, pp. e124-e130.

Gordon et al., "Clostridium septicum Alpha Toxin is Proteolytically Activated by Furin," Infection and Immunity, 1997, vol. 65, No. 10, pp. 4130-4134.

Green et al., "Cellfina Observations: Pearls and Pitfalls," Seminars in Cutaneous Medicine and Surgery, 2015, vol. 34, pp. 144-146.

Hale et al., "Long-term safety and analgesic efficacy of buprenorphine buccal film in patients with moderate-to-severe chronic pain requiring around-the-clock opioids", J Pain Res., 2017, vol. 10, pp. 233-240.

Hannafin, et al., "Adhesive capsulitis, A treatment approach", Clinical Orthopaedics and Related Research, 2000, No. 372, pp. 95-109.

Harmon "Is Cellulite Forever?" Scientific American, Monday May 4, 2009, 56, pp. 1-4.

Hatheway C. L., "Toxigenic Clostridia," Clinical Microbiology Reviews, Jan. 1990, p. 66-98.

Hay et al., "Surgical findings in the treatment of Dupuytren's disease after initial treatment with clostridial collagenase (Xiaflex)," J Hand Surg Eur, 2014, vol. 39, No. 5, pp. 463-465.

Health News, "Goodbye, Cellulite Thighs", WebMD, 2006, pp. 1-2.

Hellstrom et al., "Safety Profile of Collagenase Clostridium Histolyticum Stratified by Degree of Penile Curvature in Patients With Peyronie Disease", Urology, Aug. 2017, vol. 106, p. 237.e9-237.e14.

Hesse et al., "Recombinant enzymes for islet isolation: purification of a collagenase from clostridium histolyticum and cloning/ expression of the gene," Transplantation Proceedings, 1995, vol. 27, No. 6, pp. 3287-3289.

Heuck et al., "Conformational Changes That Effect Oligomerization and Initiate Pore Formation are Triggered Throughout Perfringolysin O Upon Binding to Cholesterol," J. Biol. Chem., 2007, vol. 282, No. 31, pp. 22629-22637.

Hexsel DM, Dal'Forno T, Hexsel CL. A validated photonumeric cellulite severity scale. JEADV 2009; 23: 523-528.

Hexsel et al., "Noninvasive Treatment of Cellulite Utilizing an Expedited Treatment Protocol with a Dual Wavelength Laser-suction and Massage Ddevice", Journal of Cosmetic and Laser Therapy, 2013, vol. 15, pp. 65-69.

Endo et al., "Purification and Properties of Collagenase from a *Streptomyces* Species", J. Biochem, vol. 102, 1987, pp. 163-170.

Matsushita et al., "Substrate recognition by collagen-binding domain of Clostridium histolyticum Class I Collagenase", J Biol Chem, vol. 278, No. 12, 2001, pp. 8761-8770.

* cited by examiner

AUX-II 96 kD Impurity

| Frequency of Impurity Occurrence by Fraction |
| --- |

| Mean and Range of Relative Percent Quantity of Impurity by Fraction |
| --- |

| Location of Band Relative to Molecular Weight Standards | The band is very close to and may appear merged with the main product band. |
| --- | --- |
| Apparent Molecular Weight Range Reported by Software | 97-111 |

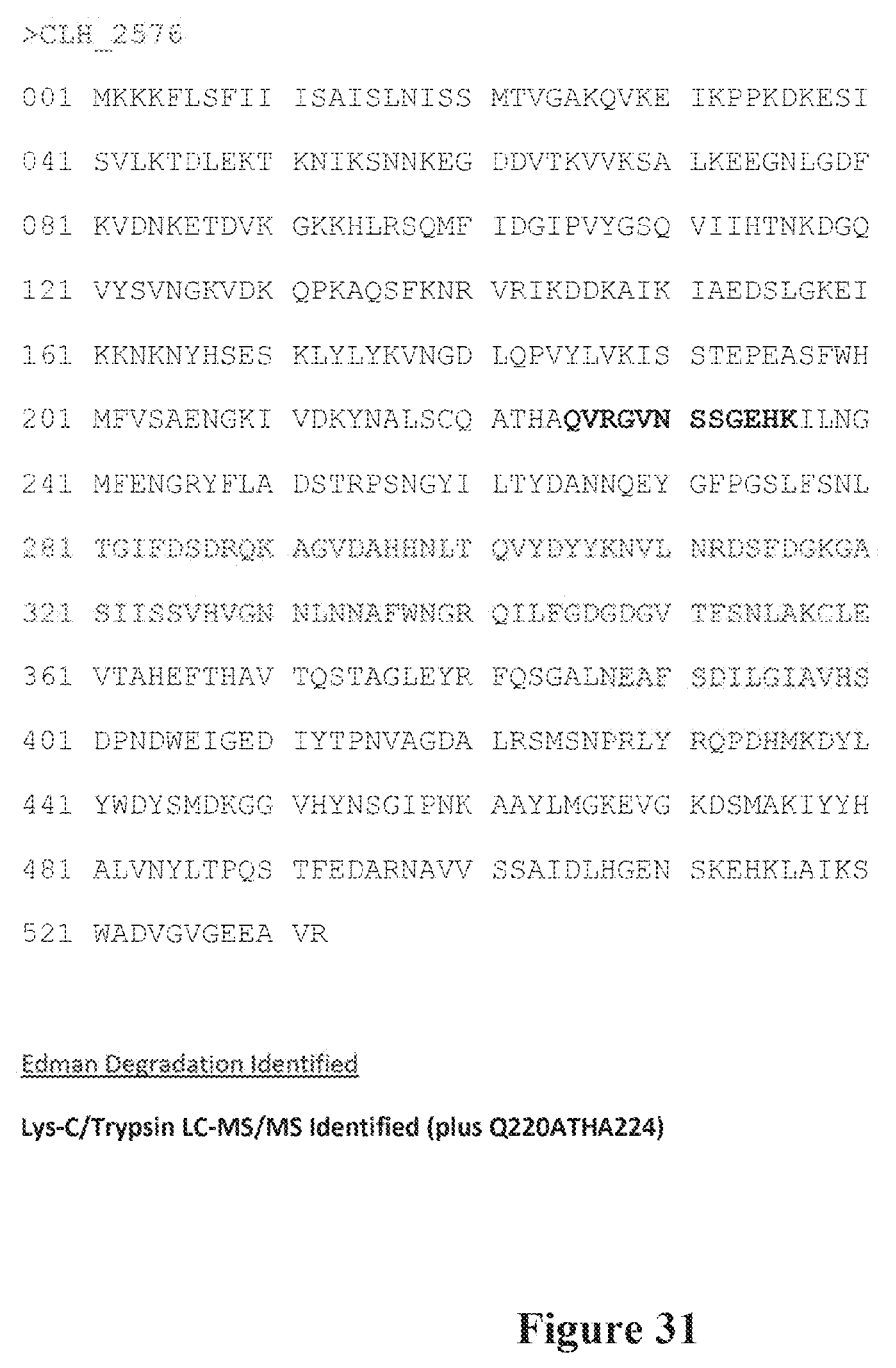

>CLH_2576

```
001  MKKKFLSFII  ISAISLNISS  MTVGAKQVKE  IKPPKDKESI
041  SVLKTDLEKT  KNIKSNNKEG  DDVTKVVKSA  LKEEGNLGDF
081  KVDNKETDVK  GKKHLRSQMF  IDGIPVYGSQ  VIIHTNKDGQ
121  VYSVNGKVDK  QPKAQSFKNR  VRIKDDKAIK  IAEDSLGKEI
161  KKNKNYHSES  KLYLYKVNGD  LQPVYLVKIS  STEPEASFWH
201  MFVSAENGKI  VDKYNALSCQ  ATHAQVRGVN  SSGEHKILNG
241  MFENGRYFLA  DSTRPSNGYI  LTYDANNQEY  GFPGSLFSNL
281  TGIFDSDRQK  AGVDAHHNLT  QVYDYYKNVL  NRDSFDGKGA
321  SIISSVHVGN  NLNNAFWNGR  QILFGDGDGV  TFSNLAKCLE
361  VTAHEFTHAV  TQSTAGLEYR  FQSGALNEAF  SDILGIAVRS
401  DPNDWEIGED  IYTPNVAGDA  LRSMSNPRLY  RQPDHMKDYL
441  YWDYSMDKGG  VHYNSGIPNK  AAYLMGKEVG  KDSMAKIYYH
481  ALVNYLTPQS  TFEDARNAVV  SSAIDLHGEN  SKEHKLAIKS
521  WADVGVGEEA  VR
```

Edman Degradation Identified

Lys-C/Trypsin LC-MS/MS Identified (plus Q220ATHA224)

Figure 31

100.0% identity in 532 residues overlap; Score: 2776.0; Gap frequency: 0.0%

```
nprA          1  MKKKFLSFIIISAISLNISSMTVGAKQVKEIKPPKDKESISVLKTDLEKTKNIKSNNKEG
CLH_2576      1  MKKKFLSFIIISAISLNISSMTVGAKQVKEIKPPKDKESISVLKTDLEKTKNIKSNNKEG
                 ************************************************************ nprA         61  DDVTKVVKSALKEEGNLGDFKVDNKETDVKGKKHLRSQMFIDGIPVYGSQVIIHTNKDGQ
CLH_2576     61  DDVTKVVKSALKEEGNLGDFKVDNKETDVKGKKHLRSQMFIDGIPVYGSQVIIHTNKDGQ
                 ************************************************************ nprA        121  VYSVNGKVDKQPKAQSFKNRVRIKDDKAIKIAEDSLGKEIKKNKNYHSESKLYLYKVNGD
CLH_2576    121  VYSVNGKVDKQPKAQSFKNRVRIKDDKAIKIAEDSLGKEIKKNKNYHSESKLYLYKVNGD
                 ************************************************************ nprA        181  LQPVYLVKISSTEPEASFWHMFVSAENGKIVDKYNALSC ATHAQVRGVNSSGEHKILNG
CLH_2576    181  LQPVYLVKISSTEPEASFWHMFVSAENGKIVDKYNALSC ATHAQVRGVNSSGEHKILNG
                 ************************************************************ nprA        241  MFENGRYFLADSTRPSNGYILTYDANNQEYGFPGSLFSNLTGIFDSDRQKAGVDAHHNLT
CLH_2576    241  MFENGRYFLADSTRPSNGYILTYDANNQEYGFPGSLFSNLTGIFDSDRQKAGVDAHHNLT
                 ************************************************************ nprA        301  QVYDYYKNVLNRDSFDGKGASIISSVHVGNNLNNAFWNGRQILFGDGDGVTFSNLAKCLE
CLH_2576    301  QVYDYYKNVLNRDSFDGKGASIISSVHVGNNLNNAFWNGRQILFGDGDGVTFSNLAKCLE
                 ************************************************************ nprA        361  VTAHEFTHAVTQSTAGLEYRFQSGALNEAFSDILGIAVHSDPNDWEIGEDIYTPNVAGDA
CLH_2576    361  VTAHEFTHAVTQSTAGLEYRFQSGALNEAFSDILGIAVHSDPNDWEIGEDIYTPNVAGDA
                 ************************************************************ nprA        421  LRSMSNPRLYRQPDHMKDYLYWDYSMDKGGVHYNSGIPNKAAYLMGKEVGKDSMAKIYYH
CLH_2576    421  LRSMSNPRLYRQPDHMKDYLYWDYSMDKGGVHYNSGIPNKAAYLMGKEVGKDSMAKIYYH
                 ************************************************************ nprA        481  ALVNYLTPQSTFEDARNAVVSSAIDLHGENSKEHKLAIKSWADVGVGEEAVR
CLH_2576    481  ALVNYLTPQSTFEDARNAVVSSAIDLHGENSKEHKLAIKSWADVGVGEEAVR
                 ***************************************************
```

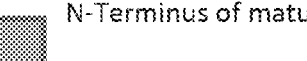 N-Terminus of mature protease

Figure 33

LEGEND:

| | | | |
|---|---|---|---|
| 1 | +control (thermolysin), 1 ng | 7 | Blank |
| 2 | Molecular Weight Reference | 8 | Blank |
| 3 | Blank | 9 | HIC Eluate Dev-25A, 4 µg |
| 4 | MQF Dev-25A, 2 µg | 10 | Blank |
| 5 | Blank | 11 | Aux II Pool 1000808, 10 µg |
| 6 | HIC Load Dev-13, 3 µg | 12 | Blank |

Figure 35: Casein Zymography PAGE Image of CCH In-Process Product Streams: TFF-1 conc., AUX-I Pool, AUX-I Intermediate, AUX-II Intermediate, BDS

LEGEND:

1  + Control (Thermolysin), 1 ng
2  Molecular Weight Reference
3  Blank
4  TFF-1 Conc. 10000808, 10 μg
5  Blank
6  AUX-I Pool 10000808, 10 μg 7  Blank
8  AUX-I Int. 10000808, 10 μg
9  Blank
10  AUX-II Int. 10000808, 10 μg
11  Blank
12  BDS 10000808, 10 μg

LEGEND:

1   + Control (thermolysin), 1 ng
2   Molecular Weight Reference
3   AUX-II Fxn 1 1000414, 6.4 µg
4   AUX-II Fxn 2 1000414, 14.4 µg
5   AUX-II Fxn 3 1000414, 10 µg 6   AUX-II Fxn 4 1000414, 10 µg
7   AUX-II Fxn 5 1000414, 10 µg
8   AUX-II Fxn 6 1000414, 11.2 µg
9   AUX-II Fxn 7 1000414, 6.2 µg
10  AUX-II Fxn 8 1000414, 5.8 µg

LEGEND:

1  Molecular Weight Reference

2  AUX-I Fxn 9 1000414, 8.8 µg

3  AUX-I Fxn 10 1000414, 10 µg

4  AUX-I Fxn 11 1000414, 10 µg

5  AUX-I Fxn 12 1000414,10 µg

6  AUX-I Fxn 13 1000414, 10 µg

7  AUX-I Fxn 14 1000414, 10 µg

8  AUX-I Fxn 15 1000414, 10 µg

9  AUX-I Fxn 16 1000414, 14 µg

10  AUX-I Fxn 17 1000414, 10 µg

LEGEND:

1   + Control (thermolysin), 1 ng
2   Molecular Weight Reference
3   AUX-II Fxn 1 1000414 Tris-Gly, 10 µg
4   AUX-II Fxn 1 1000414 LDS, 10 µg
5   AUX-II Fxn 7 1000414 Tris-Gly, 9.3 µg 6   AUX-II Fxn 7 1000414 LDS, 9.3 µg
7   AUX-I Fxn 8 1000414 Tris-Gly, 6.5 µg
8   AUX-I Fxn 8 1000414 LDS, 6.5 µg
9   AUX-I Fxn 17 1000414 Tris-Gly, 11 µg
10  AUX-I Fxn 17 1000414 LDS, 11 µg

LEGEND:

| | | | |
|---|---|---|---|
| 1 | TFF-1 Conc. Dev-25A, 34 µg | 7 | Blank |
| 2 | Molecular Weight Reference | 8 | AUX-I Fxn 17 001138, 14.8 µg |
| 3 | Blank | 9 | Blank |
| 4 | AUX-I Fxn 7 Dev-25A, 4.5 µg | 10 | AUX-I Fxn 18 001138, 10.3 µg |
| 5 | Blank | 11 | Blank |
| 6 | AUX-I Fxn 17 Dev-25A, 5 µg | 12 | AUX-I Fxn 19 001138, 8.1 µg |

Figure 40A: Zymography SDS-PAGE Gel Images of CCH Lot 0010987

LEGEND:

1  Positive Control (TL)
2  Molecular Weight Reference
3  Empty
4  Mustang Q Filtrate, 2.1 μg load
5  Empty
6  HIC Eluate, 4.9 μg load 7  Empty
8  AUX-I Pool, 10 μg load
9  Empty
10  AUX-I Intermediate, 10 μg load
11  Empty
12  Assay Blank

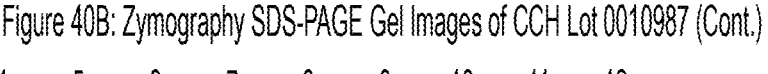
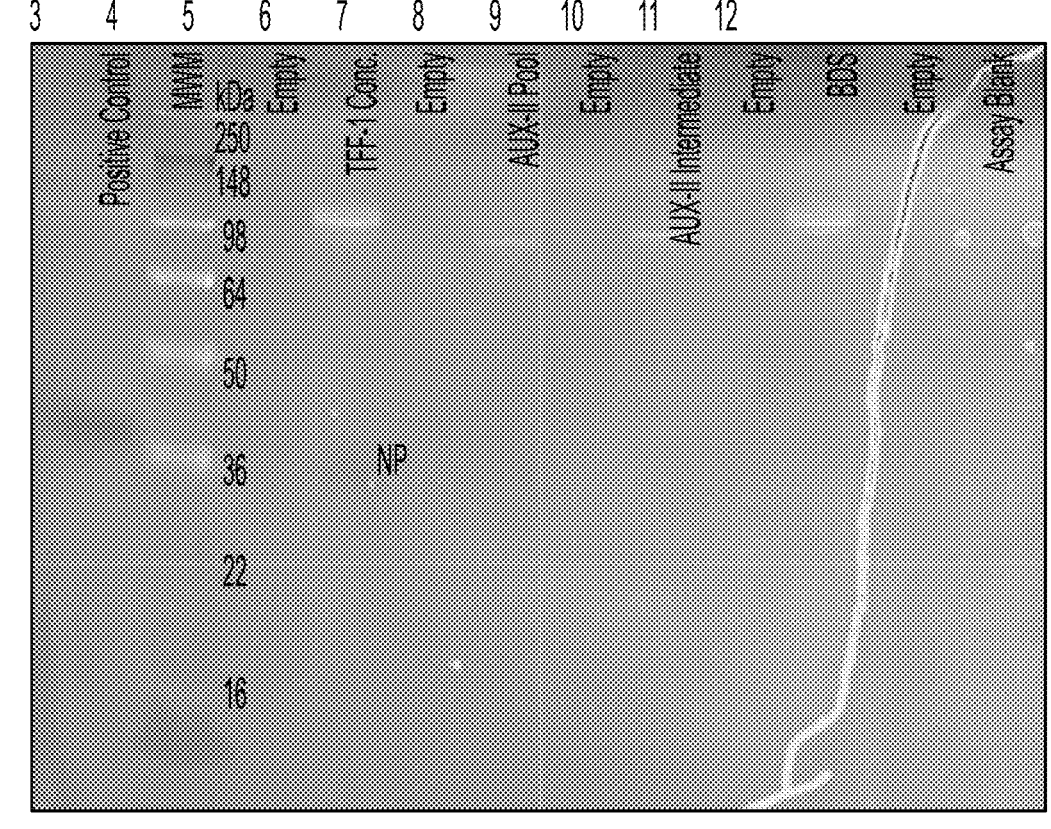
LEGEND:
1  Positive Control (TL)          7  Empty
2  Molecular Weight Reference     8  AUX-II Intermediate, 10 μg load
3  Empty                          9  Empty
4  TFF-1 Concentrate, 10 μg load  10  Bulk Drug Substance, 10 μg load
5  Empty                          11  Empty
6  AUX-II Pool, 10 μg load        12  Assay Blank
Figure 40 B

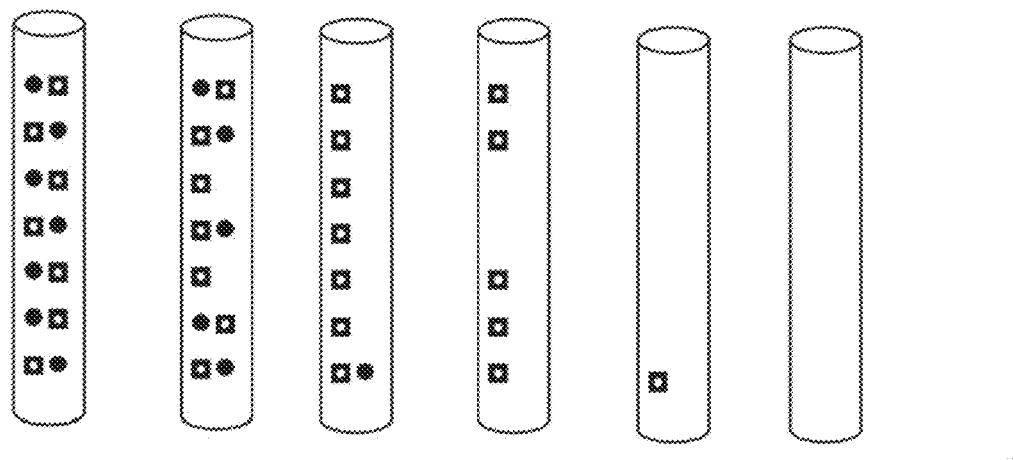
Ion Exchange (IEX) Chromatography Column depicting amount of collagenase II (●) and Collagenase I (▫) retained over time
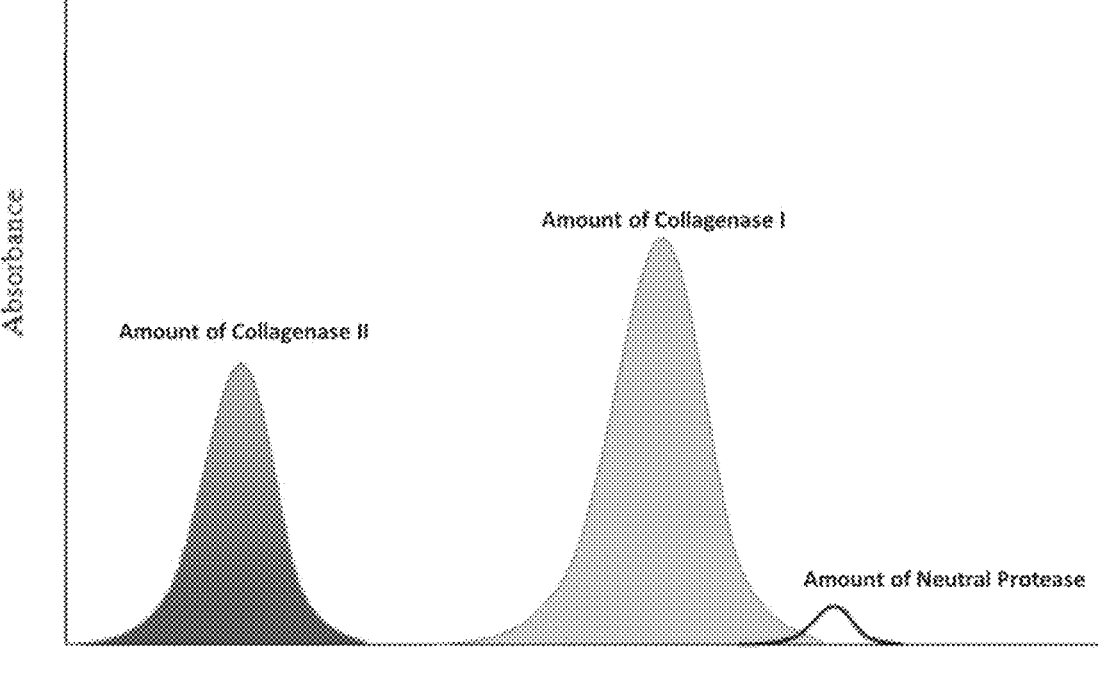
Figure 41

| AUX Peak and Band | Batch Number | Estimated Percent in Product Peak |
|---|---|---|
| AUX- I - Product | C50-1000357- IEX | 95.4 |
| AUX- I - Product | C50-1000375- IEX | 95.6 |
| AUX- I - Product | C50-1000413- IEX | 95.1 |
| AUX- I - Product | C50-1000415- IEX | 95.8 |
| AUX- I - Product | C50-1000416- IEX | 93.8 |
| AUX- I - Product | C50-1000516- IEX | 93.0 |
| AUX- I - Product | C50-1000517- IEX | 93.7 |
| AUX- I - Product | C50-1000518- IEX | 92.9 |
| AUX- I - Product | C50-1000519- IEX | 94.0 |
| AUX- I - Product | C50-1000520- IEX | 94.7 |
| AUX- I - Product | C50-1000656- IEX | 94.6 |
| AUX- I - Product | C50-1000807- IEX | 95.3 |
| AUX- I - Product | C50-1000808- IEX | 87.8 |
| AUX- I - Product | C50-1000809- IEX | 85.3 |
| AUX- I - Product | C50-1000810- IEX | 88.4 |
| AUX- I - Product | C50-1000811- IEX | 84.7 |
| AUX- I - Product | C50-1001031- IEX | 96.1 |
| AUX- I - Product | C50-1001032- IEX | 97.5 |
| AUX- I - Product | C50-1001045- IEX | 96.7 |
| AUX- I - Product | C50-0005453- IEX | 97.0 |
| AUX- I - Product | C50-0005725- IEX | 96.2 |
| AUX- I - Product | C50-0006126- IEX | 96.5 |
| AUX- I - Product | C50-0006337- IEX | 95.0 |
| AUX- I - Product | C50-0006544- IEX | 95.9 |
| AUX- I - Product | C50-0006775- IEX | 94.4 |
| AUX- I - Product | C50-0006955- IEX | 94.7 |
| AUX- I - Product | C50-0007273- IEX | 95.2 |
| AUX- I - Product | C50-0007449- IEX | 94.5 |
| AUX- II - Product | C50-1000357- IEX | 96.5 |
| AUX- II - Product | C50-1000375- IEX | 96.6 |
| AUX- II - Product | C50-1000413- IEX | 95.6 |
| AUX- II - Product | C50-1000415- IEX | 97.2 |

Figure 46 A

| AUX Peak and Band | Batch Number | Estimated Percent In Product Peak |
|---|---|---|
| AUX-II - Product | C50-1000416-IEX | 95.6 |
| AUX-II - Product | C50-1000516-IEX | 96.4 |
| AUX-II - Product | C50-1000517-IEX | 95.6 |
| AUX-II - Product | C50-1000518-IEX | 96.1 |
| AUX-II - Product | C50-1000519-IEX | 96.2 |
| AUX-II - Product | C50-1000520-IEX | 96.7 |
| AUX-II - Product | C50-1000656-IEX | 95.8 |
| AUX-II - Product | C50-1000807-IEX | 96.9 |
| AUX-II - Product | C50-1000808-IEX | 94.0 |
| AUX-II - Product | C50-1000809-IEX | 91.6 |
| AUX-II - Product | C50-1000810-IEX | 94.3 |
| AUX-II - Product | C50-1000811-IEX | 89.4 |
| AUX-II - Product | C50-1001031-IEX | 97.7 |
| AUX-II - Product | C50-1001032-IEX | 95.3 |
| AUX-II - Product | C50-1001045-IEX | 95.1 |
| AUX-II - Product | C50-0005453-IEX | 97.3 |
| AUX-II - Product | C50-0005725-IEX | 96.8 |
| AUX-II - Product | C50-0006126-IEX | 97.7 |
| AUX-II - Product | C50-0006337-IEX | 97.4 |
| AUX-II - Product | C50-0006544-IEX | 95.9 |
| AUX-II - Product | C50-0006775-IEX | 96.5 |
| AUX-II - Product | C50-0006955-IEX | 93.9 |
| AUX-II - Product | C50-0007273-IEX | 96.9 |
| AUX-II - Product | C50-0007449-IEX | 96.1 |
| AUX-I - 90 kDa | C50-1000357-IEX | 2.3 |
| AUX-I - 90 kDa | C50-1000375-IEX | 2.3 |
| AUX-I - 90 kDa | C50-1000413-IEX | 2.6 |
| AUX-I - 90 kDa | C50-1000415-IEX | 2.4 |
| AUX-I - 90 kDa | C50-1000416-IEX | 2.7 |
| AUX-I - 90 kDa | C50-1000516-IEX | 3.8 |
| AUX-I - 90 kDa | C50-1000517-IEX | 3.6 |
| AUX-I - 90 kDa | C50-1000518-IEX | 4.0 |
| AUX-I - 90 kDa | C50-1000519-IEX | 3.3 |
| AUX-I - 90 kDa | C50-1000520-IEX | 3.3 |
| AUX-I - 90 kDa | C50-1000656-IEX | 3.4 |
| AUX-I - 90 kDa | C50-1000807-IEX | 2.8 |
| AUX-I - 90 kDa | C50-1000808-IEX | 9.7 |
| AUX-I - 90 kDa | C50-1000809-IEX | 12.2 |

Figure 46 B

| AUX Peak and Band | Batch Number | Estimated Percent In Product Peak |
|---|---|---|
| AUX-I - 90 kDa | C50-1000810-IEX | 10.2 |
| AUX-I - 90 kDa | C50-1000811-IEX | 13.2 |
| AUX-I - 90 kDa | C50-1001031-IEX | 2.0 |
| AUX-I - 90 kDa | C50-1001032-IEX | 1.5 |
| AUX-I - 90 kDa | C50-1001045-IEX | 1.8 |
| AUX-I - 90 kDa | C50-0005453-IEX | 1.6 |
| AUX-I - 90 kDa | C50-0005725-IEX | 2.1 |
| AUX-I - 90 kDa | C50-0006126-IEX | 1.9 |
| AUX-I - 90 kDa | C50-0006337-IEX | 2.3 |
| AUX-I - 90 kDa | C50-0006544-IEX | 2.2 |
| AUX-I - 90 kDa | C50-0006775-IEX | 2.7 |
| AUX-I - 90 kDa | C50-0006955-IEX | 2.7 |
| AUX-I - 90 kDa | C50-0007273-IEX | 2.2 |
| AUX-I - 90 kDa | C50-0007449-IEX | 2.5 |
| AUX-II - 96 kDa | C50-1000357-IEX | 0.1 |
| AUX-II - 96 kDa | C50-1000375-IEX | 0.3 |
| AUX-II - 96 kDa | C50-1000413-IEX | 0.0 |
| AUX-II - 96 kDa | C50-1000415-IEX | 0.1 |
| AUX-II - 96 kDa | C50-1000416-IEX | 0.1 |
| AUX-II - 96 kDa | C50-1000516-IEX | 0.5 |
| AUX-II - 96 kDa | C50-1000517-IEX | 0.3 |
| AUX-II - 96 kDa | C50-1000518-IEX | 0.4 |
| AUX-II - 96 kDa | C50-1000519-IEX | 0.6 |
| AUX-II - 96 kDa | C50-1000520-IEX | 0.5 |
| AUX-II - 96 kDa | C50-1000656-IEX | 0.6 |
| AUX-II - 96 kDa | C50-1000807-IEX | 0.1 |
| AUX-II - 96 kDa | C50-1000808-IEX | 2.7 |
| AUX-II - 96 kDa | C50-1000809-IEX | 3.3 |
| AUX-II - 96 kDa | C50-1000810-IEX | 2.2 |
| AUX-II - 96 kDa | C50-1000811-IEX | 6.7 |
| AUX-II - 96 kDa | C50-1001031-IEX | 0.1 |
| AUX-II - 96 kDa | C50-1001032-IEX | 0.2 |
| AUX-II - 96 kDa | C50-1001045-IEX | 0.1 |
| AUX-II - 96 kDa | C50-0005453-IEX | 0.1 |
| AUX-II - 96 kDa | C50-0005725-IEX | 0.2 |
| AUX-II - 96 kDa | C50-0006126-IEX | 0.1 |
| AUX-II - 96 kDa | C50-0006337-IEX | 0.1 |
| AUX-II - 96 kDa | C50-0006544-IEX | 0.0 |

Figure 46 C

| AUX Peak and Band | Batch Number | Estimated Percent In Product Peak |
|---|---|---|
| AUX-II - 96 kDa | C50-0006775-IEX | 0.0 |
| AUX-II - 96 kDa | C50-0006955-IEX | 0.1 |
| AUX-II - 96 kDa | C50-0007273-IEX | 0.1 |
| AUX-II - 96 kDa | C50-0007449-IEX | 0.0 |

Figure 46 D

PROCESS INTERMEDIATE IN THE PURIFICATION OF COLLAGENASE DRUG SUBSTANCES

RELATED APPLICATIONS

This application is a continuation of U.S. application Ser. No. 17/559,782, filed on Dec. 22, 2021, which is a divisional of U.S. application Ser. No. 15/939,231, filed on Mar. 28, 2018, which issued on Oct. 18, 2022, as U.S. Pat. No. 11,473,074, which claims priority to U.S. Provisional Application Ser. No. 62/477,846, filed on Mar. 28, 2017, the disclosure of each of which is incorporated herein by reference in its entirety.

SEQUENCE LISTING

The contents of the electronic sequence listing (117326000532_SL.xml; Size: 10,666 bytes; and Date of Creation: Feb. 15, 2023) is herein incorporated by reference in its entirety.

TECHNICAL FIELD

The present invention relates to the fields of collagenase production and collagenase products, and particularly to improving the reproducibility, purity, and stability of collagenase I and collagenase II compositions, wherein the compositions are pure to at least 95% by area as measured by reverse phase high pressure liquid chromatography (RP-HPLC) and essentially free of neutral protease.

BACKGROUND

A process for manufacturing highly pure (at least 95% pure) collagenase from fermentations of *C. histolyticum* has been previously described in U.S. Pat. No. 7,811,560. Collagenase I and II are enzymes that break down collagen, the most abundant structural protein in mammals. These enzymes are used for the treatment of a variety of collagen-mediated diseases, e.g., Dupuytren's contracture, Peyronie's disease, lipoma and adhesive capsulitis. U.S. Pat. Nos. 6,086,872 and 5,589,171, disclose the use of collagenase preparations in the treatment of Dupuytren's disease. U.S. Pat. No. 6,022,539, discloses the use of collagenase preparations in the treatment of Peyronie's disease. U.S. Pat. Nos. 6,958,150 and 7,842,673, disclose the use of collagenase for the treatment of lipoma. U.S. Patent Application Publication No. 2006/020448A1, discloses the use of collagenase in the treatment of adhesive capsulitis. U.S. Patent Application Publication Nos. 2014/0335072 and 2016/0279046 disclose the use of collagenase for treating cellulite.

A major source of collagenase is from the fermentation of *C. histolyticum*. An injectable formulation comprising *C. histolyticum* collagenase I and collagenase II is sold under the trade name XIAFLEX® and is approved by the U.S. Food and Drug Administration for the treatment of Dupuytren's contracture and Peyronie's disease. The injectable formulation is called XIAPEX® in Europe and other countries. Amino acid sequences for collagenase I and collagenase II are encoded by the colG and colH genes, respectively. An amino acid sequence for colG is described in GenBank Acc. No. D87215 and Matsushita et al. (1999), *Journal of Bacteriology* 181(3): 923-933, and an amino acid sequence for colH is described in GenBank Acc. No. D29981 and Yoshihara et al. (1994), *Journal of Bacteriology* 176(21): 6489-6496. Collagenase AUX I has a single polypeptide chain consisting of approximately 1000 amino acids with a molecular weight of about 113 kDa. Collagenase AUX II has also a single polypeptide chain consisting of about 1000 amino acids with a molecular weight of about 112 kDa.

Collagenase I and collagenase II are metalloproteases and require tightly bound zinc and loosely bound calcium for their activity (Eddie L. Angleton and H. E. Van Wart, *Biochemistry* 1988, 27, 7406-7412). Both collagenase I and collagenase II have broad specificity toward all types of collagen (Steinbrink, D; Bond, M and Van Wart, H; (1985), *JBC*, 260 p 2771-2776). These collagenases digest collagen by hydrolyzing the triple-helical region of collagen under physiological conditions (Steinbrink, D; Bond, M and Van Wart, H; (1985), *JBC*, 260 p 2771-2776). Even though each collagenase shows different specificity (i.e., each has a different preferred amino sequence for cleavage), together, they have synergistic activity toward collagen (Mandl, I., (1964), *Biochemistry*, 3: p. 1737-1741; Vos-Scheperkeuter, G H, (1997), *Cell Transplantation*, 6: p. 403-412).

Collagenase for use in therapy may be obtained from a variety of sources including mammalian, fungal, and bacterial sources. One common source of crude collagenase is from a bacterial fermentation process, specifically the fermentation of *Clostridium histolyticum* (*C. histolyticum*). The crude collagenase obtained from *C. histolyticum* may be purified using any of a number of chromatographic techniques. However, many other enzymes besides collagenases are secreted into the fermentation liquid, including a variety of toxins.

Previously as described in U.S. 2015/0010532, genomic sequencing and analysis of secreted toxins from *C. histolyticum* strain 004 were performed to investigate the functionality of these toxins in fermentations that produced collagenases. The toxins investigated were alpha toxin (lethal factor), beta toxins (type I and type II collagenases), gamma toxin (clostripain), delta toxin (neutral protease), and epsilon toxin (oxygen labile hemolysin). Based on the genomic sequence analysis, only the collagenases and clostripain were thought to be functional toxins of strain 004. The other toxins were deemed non-functional based on critical amino acid sequence differences between the *C. histolyticum* proteins and respective model proteins.

Delta toxin, also known as neutral protease (NP), is a metalloprotease from *C. histolyticum*. Neutral protease is a member of the M4 family of metalloproteases and according to the MEROPS peptidase database, neutral protease has structural similarities to the M4 family including common sequence motifs, substrate specificity, and cofactor requirements. Thermolysin is the most studied and understood enzyme of the M4 family. Relevant to this study, thermolysin from *Bacillus thermoproteolyticus* has previously been cloned and sequenced and the information deposited in GenBank under accession number CAA54291. Thermolysin is a zinc metalloprotease with a mature enzyme molecular weight of 34.6 kDa. Thermolysin and all members of the M4 peptidase family are composed of a signal peptide, a prosequence, and a mature sequence.

When thermolysin is generated by a cell, it starts as an inactive enzyme (pro-enzyme) because the protein prosequence ahead of the mature enzyme sequence inhibits the thermolysin. The prosequence represents two thirds the size of secreted pro-enzyme while the mature enzyme represents one third. The prosequence in thermolysin is auto-catalytically cleaved, resulting in the activation of the mature enzyme in its destination environment. The thermolysin secretion strategy is shared with neutral protease, and was the basis for concluding that the *C. histolyticum* neutral protease also started as an inactive protease. Likewise, the *C. histolyticum* neutral protease in its mature form has a similar molecular weight to thermolysin, as described in Herber (U.S. 2015/0010532) and in Maeda et al., *Cloning a neutral protease of Clostridium histolyticum, determining its substrate specificity, and designing a specific substrate*, Appl. Microbiol. Biotech., 99: 10489-99 (2015).

The similarities of thermolysin in its synthesis, secretion, activation, and substrate specificity make thermolysin a model for the neutral protease from *C. histolyticum* strain 004. While these attributes between thermolysin and the neutral protease are comparable based on the shared structural features, sequence differences do exist between the two enzymes. Relevant to the present invention, previous genomic analysis of delta toxin and homology comparison to thermolysin in Herber (U.S. 2015/0010532) concluded that neutral protease was likely secreted into the growth media, but was not active due to a divergent consensus sequence in the autocatalysis site.

A characteristic feature of thermolysin (and all neutral proteases) is the wide range of proteins on which it can act. The presence of non-specific proteases in medicines, particularly those injected into a body, are problematic as they undesirably degrade untargeted enzymes, cells, and tissues in the body—even when present in minute amounts.

Previous processes for making collagenase can sometimes result in atypical collagenase degradation. For efficient and effective commercial manufacturing of collagenase, the reproducible manufacture of highly pure collagenase free of toxins is needed.

SUMMARY

The present disclosure provides an improved process for collagenase manufacturing that removes detectable amounts of neutral protease from collagenase I and II products. The disclosure provides a collagenase product that is less susceptible to degradation, and purer than previous collagenase compositions for medical uses. In one embodiment, an investigation was conducted to identify the cause of atypical collagenase I and II degradation from *C. histolyticum* during a manufacturing process. It was discovered that neutral protease from *C. histolyticum* is present in fermentations of *C. histolyticum* in its active, mature form. Further, this neutral protease is highly active on collagenase I and collagenase II, and may cause significant degradation of both collagenases. Its continued presence during the purification process may also degrade both collagenases.

The neutral protease, previously thought to be inactive, unexpectedly becomes extensively more active in the presence of elevated amounts of one or more metals (e.g., nickel and zinc). This metal-mediated activity generates elevated levels of collagenase product fragments during the collagenase manufacturing process in the presence of parts-per-million levels of such metals, causing purity failures in at least the ion exchange (IEX) chromatography steps of the process.

The present invention also provides methods for isolating the neutral protease from the manufacturing process, methods for removing it from the process, and methods for determining its presence throughout the manufacturing process. Further, the present invention provides improved repeatability and stability of highly purified collagenase, provides collagenase I and II products essentially free from neutral protease (i.e., below detectable limits), and provides safer and more pure collagenase compositions that are essentially free of neutral protease.

Manufacturing repeatability is improved by controlling for metals during the fermentation and purification processes. Surprisingly, it was found that the presence or absence of certain metals during the purification of collagenase I and II from *C. histolyticum* affected the purity of the collagenase products. In one embodiment, zinc levels of about 80 ppm or more, or nickel levels of about 1 ppm or more result in collagenase I product and collagenase II product impurities at an elevated level as measured by SDS-PAGE (Sodium Dodecyl Sulfate Polyacrylamide Gel Electrophoresis), resulting in unacceptable levels of impurities for a drug product.

In another embodiment, when zinc levels are above about 2.75 ppm and less than about 80 ppm, collagenase is not degraded into fragments. And when nickel levels are above about 0.4 ppm and less than about 1 ppm in at least one step of the purification process, collagenase is not degraded into fragments. Further, controlling the drug purification process to maintain zinc levels at about 3 ppm or less, or nickel levels of about 0.5 ppm or less, improves the reliability and repeatability of manufacturing of collagenase products at high purities. Operating a collagenase manufacturing process with metals zinc and nickel (or other metals) at trace amounts that do not cause elevated levels of collagenase degradation results in significantly improved reliability and repeatability as compared to the previous processes.

In certain embodiments, when nickel or zinc is present in buffers for the hydrophobic interaction chromatography (HIC) step of the collagenase manufacturing process, neutral protease actively degrades collagenase I and II into smaller fragments and results in low purity (less than 95% pure as measured by SDS-PAGE) collagenase product. In some embodiments, nickel (in amounts between about 0.4 ppm and about 1 ppm) and zinc (in amounts between about 2.8 ppm and 84 ppm) do not amplify the neutral protease specific activity in the HIC and tangential flow filtration (TFF) unit operations, and do not cause significantly increased product fragment impurities in the IEX unit operation. In one embodiment, controlling the collagenase manufacturing process for nickel or zinc levels is important to obtaining high purity collagenase I and II products.

Eliminating or at least reducing neutral protease from the collagenase manufacturing process such that the collagenase composition is essentially free of neutral protease improves the safety of the product and prevents degradation of the collagenases in the product by neutral protease. Collagenase compositions are improved by adding at least one neutral protease elimination step in the manufacturing process. Reducing or eliminating neutral protease from the manufacture of collagenase products may be achieved by one or more of the following elimination steps: (a) excluding any fraction that has less than about 90% collagenase I or II content and more than about 7% content of any single impurity as measured by SDS PAGE gel or HPLC; (b) excluding any fraction that has a detectable level of neutral protease as measured by SDS PAGE gel or Zymography; or (c) excluding any fraction that is calculated to contain an excess level of neutral protease. Each may be employed individually or in combination.

More particularly, the elimination step may include the rejection of fractions that are collected after the collagenase is passed through a separation column or filter (or other separation medium) and that contains detectable levels of neutral protease as tested by SDS-PAGE or Zymography assays, before pooling the collagenase I or collagenase II fractions. In certain embodiments, fractions may be rejected even if they contain significant amounts of collagenase. Elimination may also entail rejecting or discarding any collagenase I or II fractions that have less than about 90% collagenase I or II content and more than about 7% content of any single impurity as measured by SDS PAGE gel or HPLC. The elimination step may include using the estimated amount of collagenase II produced in the process to control for which collagenase I fractions are pooled for the collagenase I product. Any of these steps can be employed in the collagenase manufacturing process to generate a collagenase I and II products essentially free of neutral protease.

One embodiment of neutral protease elimination implements process controls on ion exchange chromatography (IEX) fraction purity, where each fraction is analyzed for both purity and the most abundant impurity, and each fraction has to meet this criteria in order for the fraction to be forward processed (acceptable for pooling, drug product, and use as a pharmaceutical formulation). In this embodiment, the positional nature of neutral protease elution at the end of the collagenase I peak of the IEX step provides an effective mechanism for removal of neutral protease by autorejecting the fraction(s) that show detectable limits of neutral protease by SDS-PAGE, SDS-PAGE with densitometry, or Zymography (with or without densitometry) assays. In another embodiment, the peak fractions of collagenase I fractions collected from an IEX elution are forward processed based on the fraction meeting the desired purity and impurity criteria, along with pooling only collagenase I peak fractions until the approximate amount of collagenase I pooled matches the approximate amount of collagenase II produced by the process. This control strategy results in the elimination of additional end fractions of the collagenase I peak, such that the pooled fractions of collagenase I are essentially free of neutral protease.

The invention further provides methods for preparing pharmaceutical formulations according to the present disclosure, and methods for treating patients suffering from a collagen-mediated disease using a collagenase composition of the invention. For example, methods of treating a collagen-mediated disease are contemplated by administering an effective amount of collagenase, collagenase I, collagenase II, or a combination thereof. In one embodiment, the present disclosure is directed to a method of treating a collagen-mediated condition in a patient in need thereof (e.g., cellulite), wherein the method comprises the step of administering to the patient an effective amount of a collagenase composition, wherein the collagenase composition comprises collagenase I product and collagenase II product combined in a mass ratio of between about 0.6:1.4 collagenase Ito collagenase II and about 1.4:0.6 collagenase Ito collagenase II, and wherein the composition is essentially free of neutral protease. Further, the disclosure provides a more stable and safer pharmaceutical formulation.

Additional embodiments of the present compositions and methods and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment or aspect. Additional aspects and embodiments are set forth in the following description and claims, particularly when considered in conjunction with the accompanying examples and drawings.

BRIEF DESCRIPTION OF THE DRAWINGS

The foregoing features of embodiments will be more readily understood by reference to the following detailed description, taken with reference to the accompanying drawings, in which.

Lane 1: Molecular Weight Marker
Lane 2: Collagenase II
Lane 3: Fraction #1—94.9% purity (1.5 μg/lane)
Lane 4: Fraction #2—98.1% purity (1.5 μg/lane)
Lane 5: Fraction #3—98.4% purity (1.5 μg/lane)
Lane 6: Fraction #4—97.3% purity (1.5 μg/lane)
Lane 7: Fraction #5—96.3% purity (1.5 μg/lane)
Lane 8: Fraction #6—89.9% purity (1.5 μg/lane)
Lane 9: Blank
Lane 10: Collagenase I
Lane 11: Fraction #16 of collagenase I peak (1.5 μg/lane)

Figure 23:
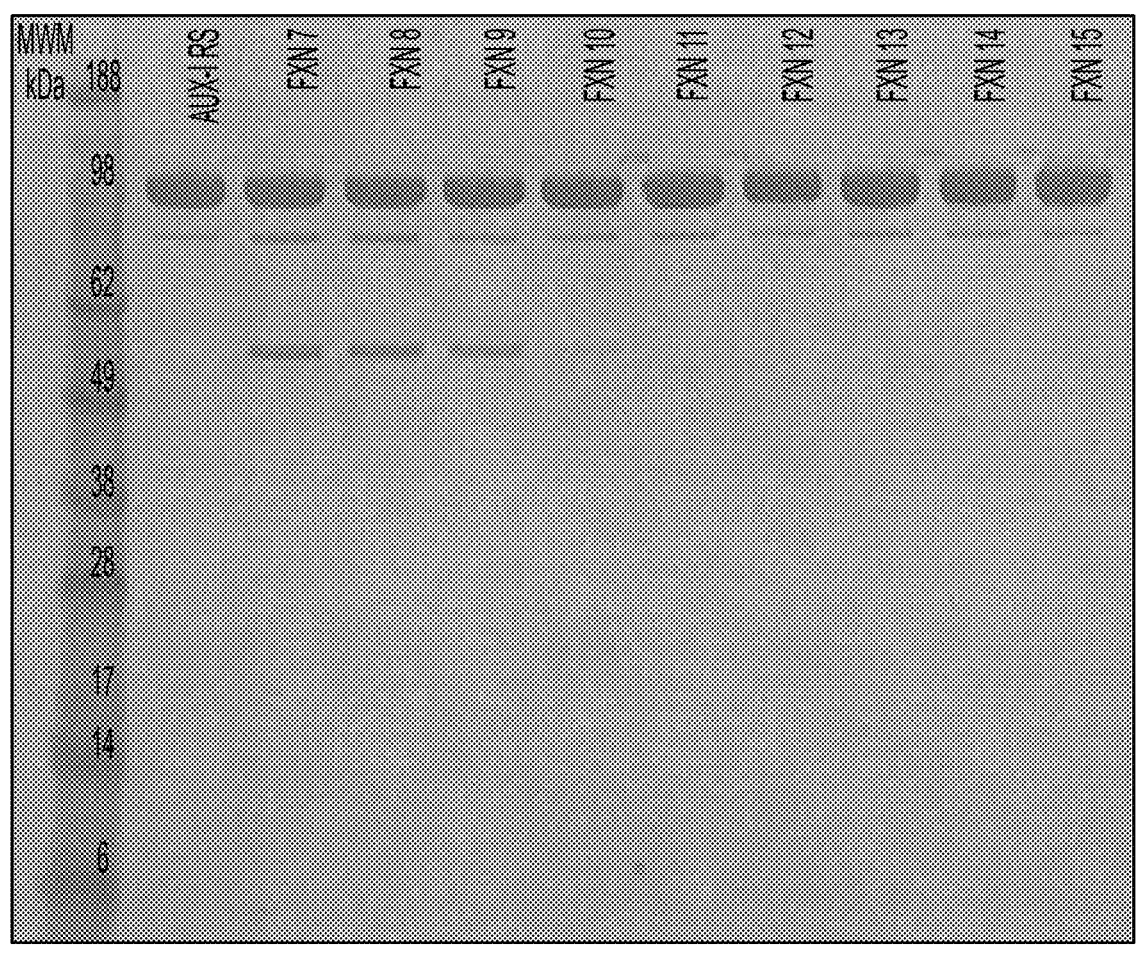

FIG. 23 is a SDS-PAGE Coomassie-stained gel showing impurities in AUX-I fractions after an IEX column during a control run in a zinc spiking study (Run DEV-25C). The AUX-I peak from the IEX column was collected in ten (10) fractions. This gel shows the typical purity of the AUX-I fractions and the typical pattern of product-related impurities.

Figure 24:
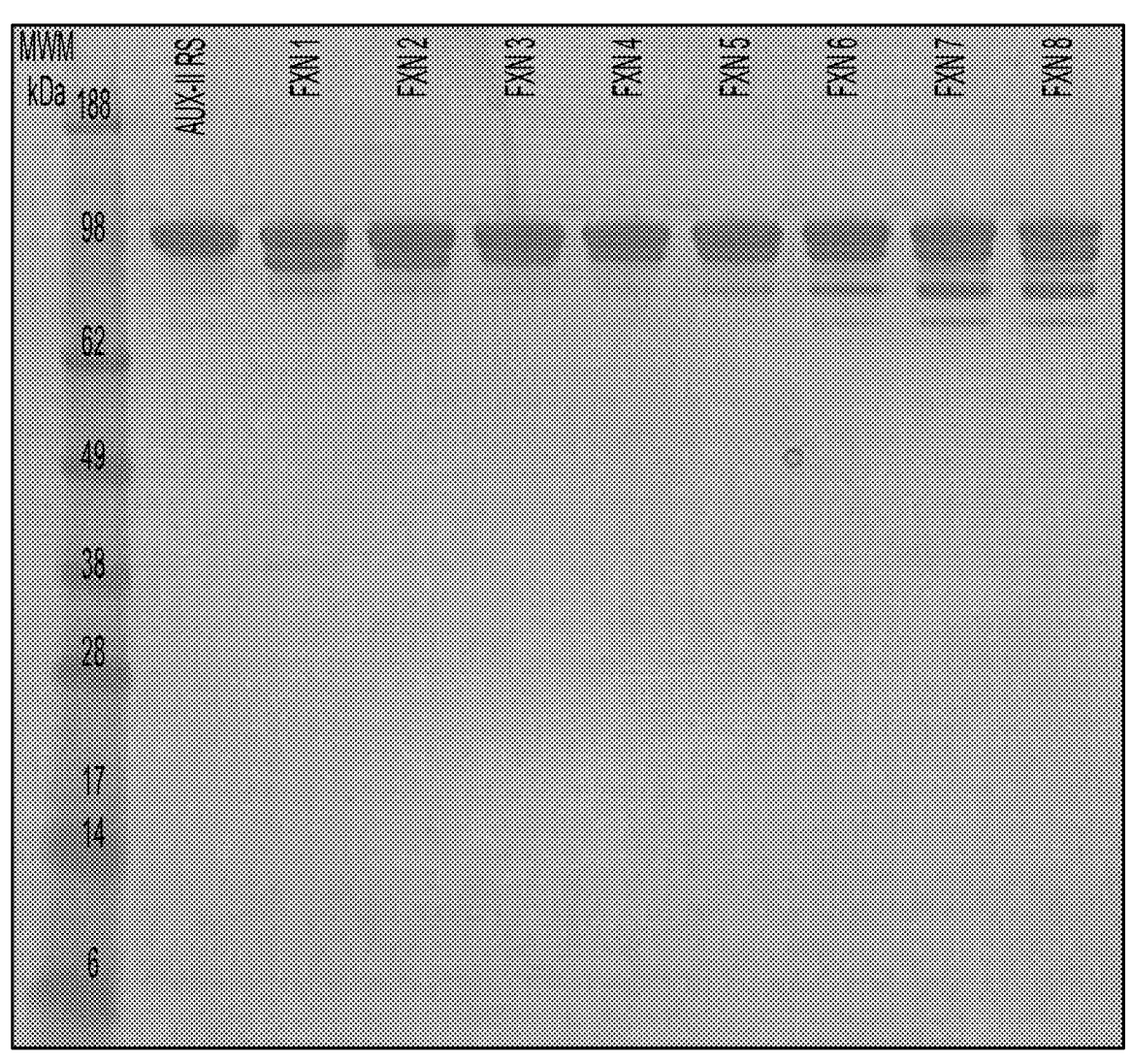

Lane 1: Molecular Weight Marker
Lane 2: Collagenase I
Lane 3: Fraction #7—87.7% purity
Lane 4: Fraction #8—86.5% purity
Lane 5: Fraction #9—92.0% purity
Lane 6: Fraction #10—95.8% purity
Lane 7: Fraction #11—97.8% purity
Lane 8: Fraction #12—97.1% purity
Lane 9: Fraction #13—97.0% purity
Lane 10: Fraction #14—96.8% purity
Lane 11: Fraction #15—96.5% purity FIG. 24 is a SDS-PAGE Coomassie-stained gel showing impurities in AUX-II fractions after an IEX column from a zinc spiking study wherein the zinc was spiked to 84 ppm (Run DEV-25B). The AUX-II peak from the IEX column was collected in eight (8) fractions. This gel shows the degradation pattern caused by the presence of zinc, with an increase in the number and intensity of impurities and a decrease in the purity of AUX-II fractions. In this gel, none of the AUX-II fractions met the purity criterion for pooling.

Lane 1: Molecular Weight Marker
Lane 2: Collagenase II
Lane 3: Fraction #1—66.4% purity (1.5 μg/lane)
Lane 4: Fraction #2—75.5% purity (1.5 μg/lane)
Lane 5: Fraction #3—79.5% purity (1.5 μg/lane)
Lane 6: Fraction #4—76.7% purity (1.5 μg/lane)
Lane 7: Fraction #5—72.1% purity (1.5 μg/lane)
Lane 8: Fraction #6—63.9% purity (1.5 μg/lane)
Lane 9: Fraction #7—52.9% purity (1.5 μg/lane)
Lane 10: Fraction #8—45.0% purity (1.5 μg/lane)

Figure 25:
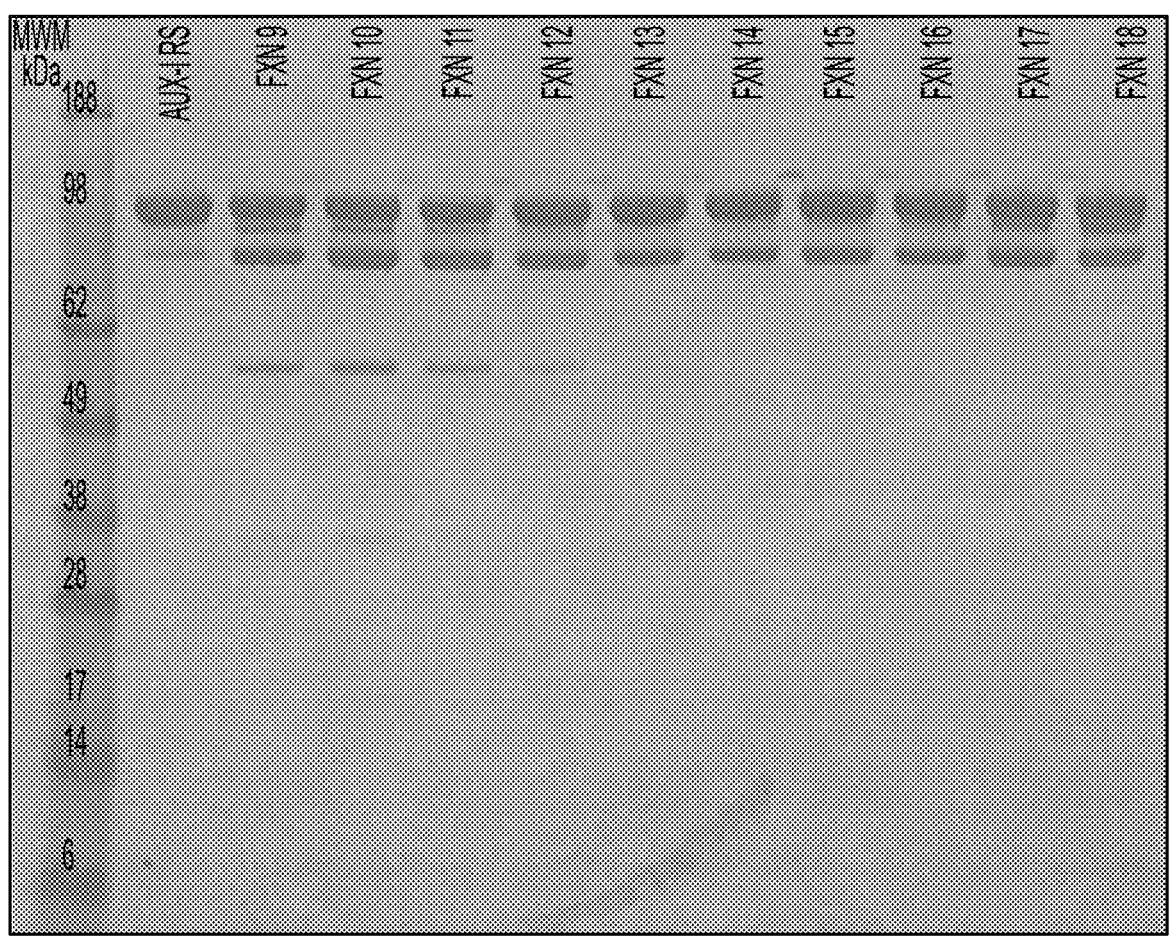

FIG. 25 is a SDS-PAGE Coomassie-stained gel showing impurities in AUX-I fractions after an IEX column from a zinc spiking study wherein the zinc was spiked to 84 ppm (Run DEV-25B). The AUX-I peak from the IEX column was collected in ten (10) fractions. This gel shows the degradation pattern caused by the presence of zinc, with an increase in the number and intensity of impurities and a decrease in the purity of AUX-I fractions. In this gel, none of the AUX-I fractions met the purity criterion for pooling.

Lane 1: Molecular Weight Marker
Lane 2: Collagenase I
Lane 3: Fraction #9—54.9% purity (1.5 μg/lane)
Lane 4: Fraction #10—50.9% purity (1.5 μg/lane)
Lane 5: Fraction #11—56.2% purity (1.5 μg/lane)
Lane 6: Fraction #12—65.2% purity (1.5 μg/lane)
Lane 7: Fraction #13—70.4% purity (1.5 μg/lane)
Lane 8: Fraction #14—70.0% purity (1.5 μg/lane)
Lane 9: Fraction #15—67.5% purity (1.5 μg/lane)
Lane 10: Fraction #16—62.4% purity (1.5 μg/lane)
Lane 11: Fraction #17—58.8% purity (1.5 μg/lane)
Lane 12: Fraction #18—52.6% purity (1.5 μg/lane)

Figure 26:
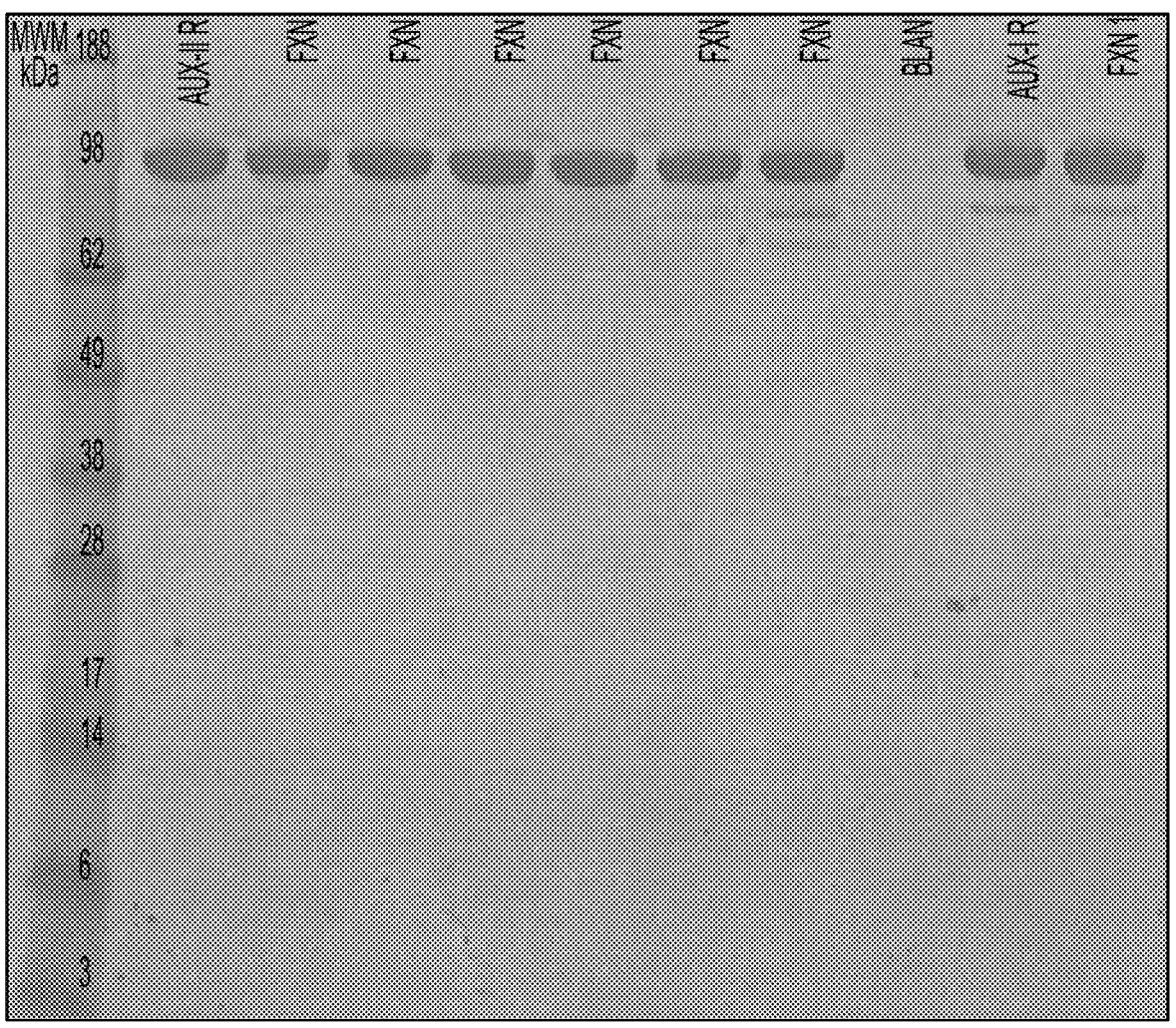

FIG. 26 is a SDS-PAGE Coomassie-stained gel showing impurities in AUX-II fractions after an IEX column from a control run in a nickel spiking study (Run DEV-25A). The AUX-II peak from the IEX column was collected in six (6) fractions. This gel shows the typical purity of the AUX-I fractions and the typical pattern of product-related impurities.

Lane 1: Molecular Weight Marker
Lane 2: Collagenase II
Lane 3: Fraction #1—95.9% purity (1.5 μg/lane)
Lane 4: Fraction #2—97.1% purity (1.5 μg/lane)
Lane 5: Fraction #3—99.1% purity (1.5 μg/lane)
Lane 6: Fraction #4—98.2% purity (1.5 μg/lane)
Lane 7: Fraction #5—96.9% purity (1.5 μg/lane)
Lane 8: Fraction #6—92.3% purity (1.5 μg/lane)
Lane 9: Blank
Lane 10: Collagenase I
Lane 11: Fraction #16 from collagenase I peak (1.5 μg/lane)

Figure 27:
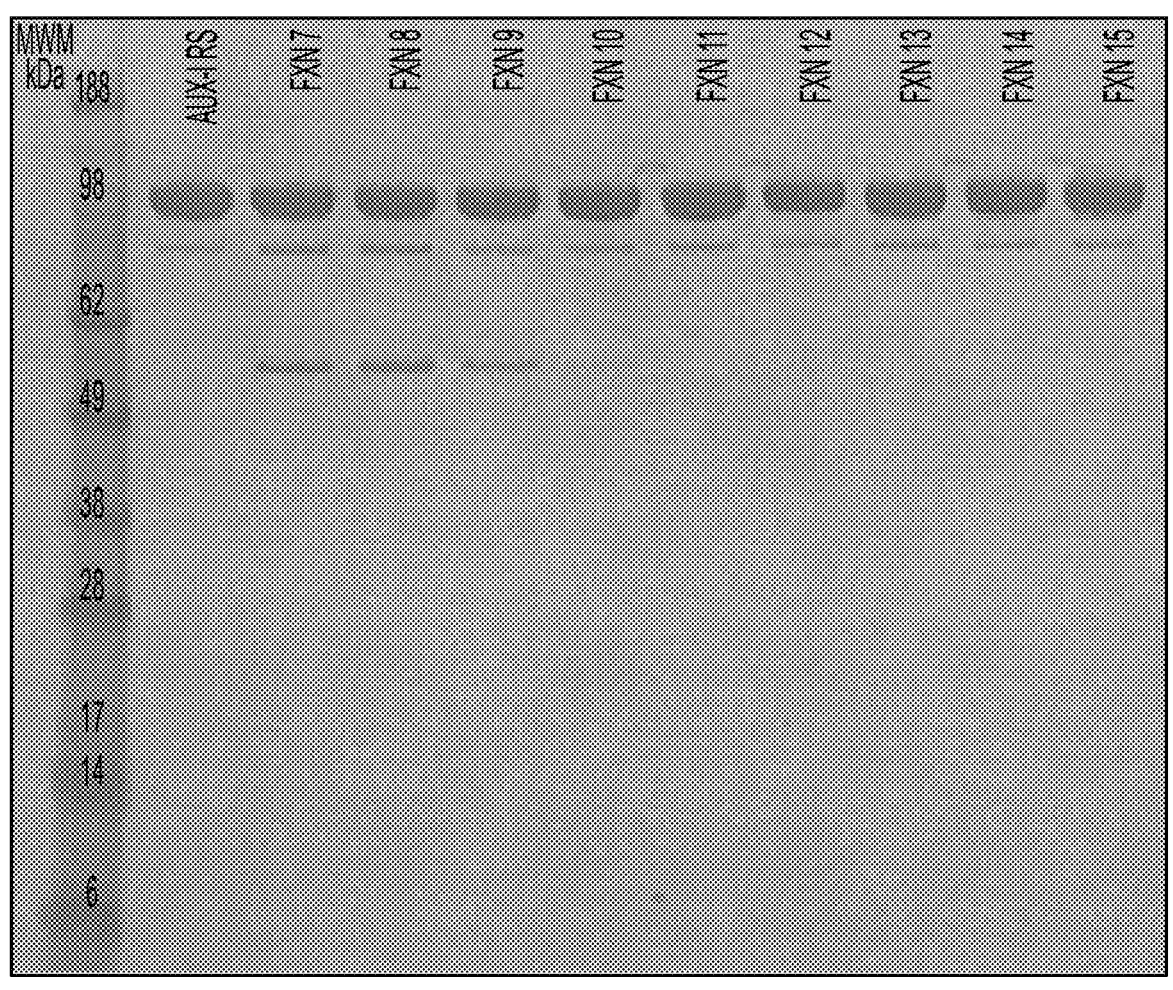

FIG. 27 is a SDS-PAGE Coomassie-stained gel showing impurities in AUX-I fractions after an IEX column from a control run in a nickel spiking study (Run DEV-25A). The AUX-I peak from the IEX column was collected in ten (10) fractions. This gel shows the typical purity of the AUX-II fractions and the typical pattern of product-related impurities.

Lane 1: Molecular Weight Marker
Lane 2: Collagenase I
Lane 3: Fraction #7—85.6% purity (1.5 μg/lane)
Lane 4: Fraction #8—85.2% purity (1.5 μg/lane)
Lane 5: Fraction #9—90.7% purity (1.5 μg/lane)
Lane 6: Fraction #10—95.5% purity (1.5 μg/lane)
Lane 7: Fraction #11—96.6% purity (1.5 μg/lane)
Lane 8: Fraction #12—97.0% purity (1.5 μg/lane)
Lane 9: Fraction #13—96.6% purity (1.5 μg/lane)
Lane 10: Fraction #14—96.8% purity (1.5 μg/lane)
Lane 11: Fraction #15—96.8% purity (1.5 μg/lane)

Figure 28:
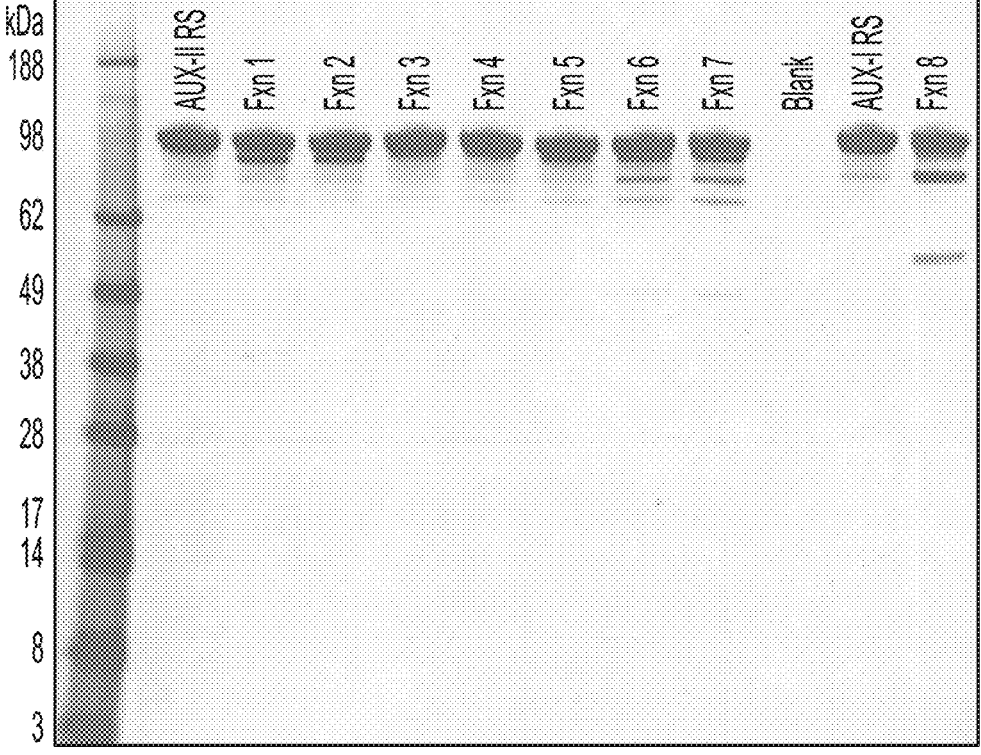

FIG. 28 is a SDS-PAGE Coomassie-stained gel showing impurities in AUX-II fractions after an IEX column from a nickel spiking study wherein the nickel was spiked to 1.2 ppm (Run DEV-25D). The AUX-II peak from the IEX column was collected in seven (7) fractions. This gel shows the degradation pattern caused by the presence of nickel, with an increase in the number and intensity of impurities and a decrease in the purity of AUX-II fractions. In this gel, none of the AUX-II fractions met the pooling criterion for purity.

Lane 1: Molecular Weight Marker
Lane 2: Collagenase II

Lane 3: Fraction #1—74.8% purity (1.5 µg/lane)
Lane 4: Fraction #2—81.8% purity (1.5 µg/lane)
Lane 5: Fraction #3—84.6% purity (1.5 µg/lane)
Lane 6: Fraction #4—85.6% purity (1.5 µg/lane)
Lane 7: Fraction #5—83.0% purity (1.5 µg/lane)
Lane 8: Fraction #6—72.3% purity (1.5 µg/lane)
Lane 9: Fraction #7—64.9% purity (1.5 µg/lane)
Lane 10: Blank
Lane 11: Collagenase I
Lane 12: Fraction #8 from collagenase I peak—62.7% purity (1.5 µg/lane)

Figure 29:
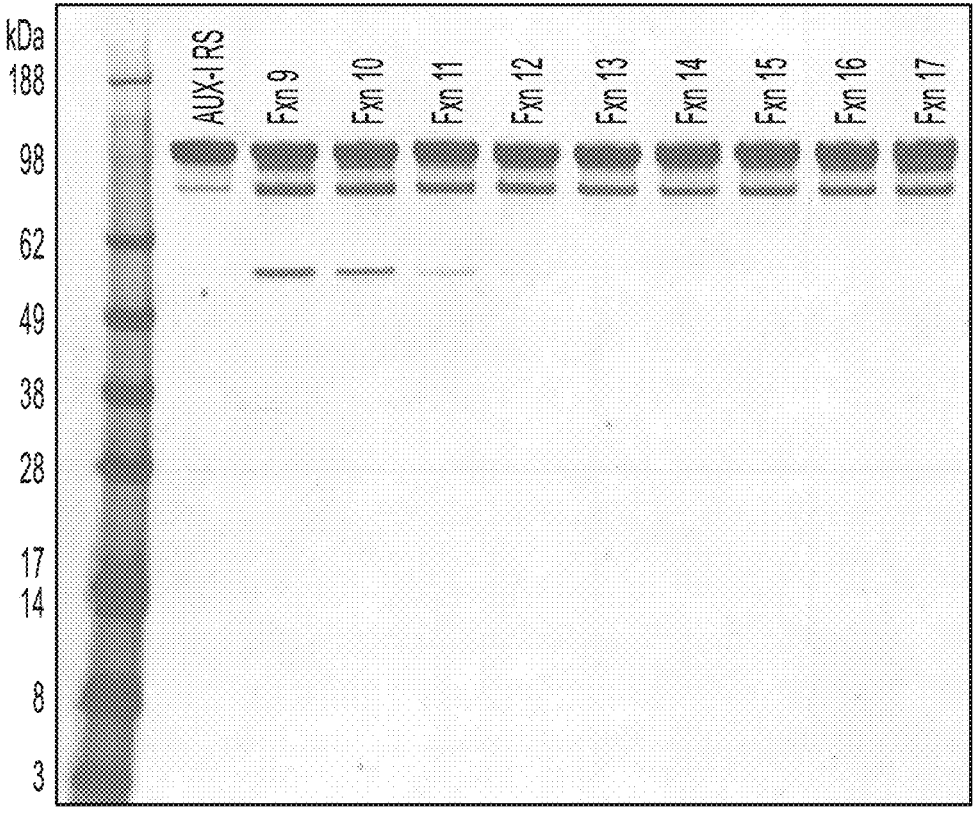

FIG. 29 a SDS-PAGE Coomassie-stained gel showing impurities in AUX-I fractions after an IEX column from a nickel spiking study wherein the nickel was spiked to 1.2 ppm (Run DEV-25D). The AUX-I peak from the IEX column was collected in ten (10) fractions. This gel shows the degradation pattern caused by the presence of nickel, with an increase in the number and intensity of impurities and a decrease in the purity of AUX-I fractions. In this gel, none of the AUX-I fractions met the pooling criterion for purity.

Lane 1: Molecular Weight Marker
Lane 2: Collagenase I
Lane 3: Fraction #9—60.3% purity (1.5 µg/lane)
Lane 4: Fraction #10—67.6% purity (1.5 µg/lane)
Lane 5: Fraction #11—81.6% purity (1.5 µg/lane)
Lane 6: Fraction #12—84.7% purity (1.5 µg/lane)
Lane 7: Fraction #13—84.1% purity (1.5 µg/lane)
Lane 8: Fraction #14—82.6% purity (1.5 µg/lane)
Lane 9: Fraction #15—82.0% purity (1.5 µg/lane)
Lane 10: Fraction #16—72.4% purity (1.5 µg/lane)
Lane 11: Fraction #17—68.6% purity (1.5 µg/lane)

Figure 30:
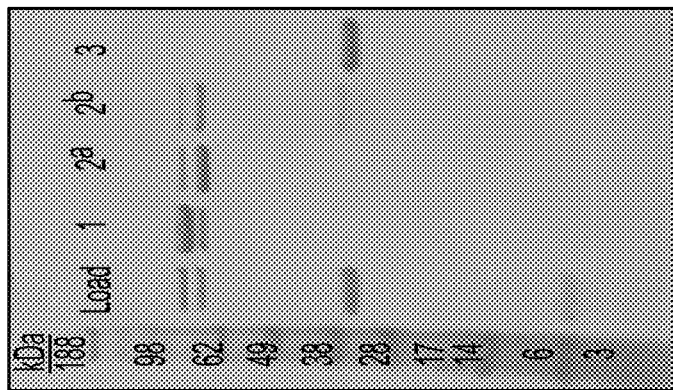

FIG. 30 is a Q-Sepharose High Performance (Q-HP) chromatogram and SDS-PAGE with Coomassie staining gel image. The load and merged AUX I and AUX II pooled fractions are shown. The Q-HP chromatogram represents the purification of the neutral protease from the HIC chromatography step's water waste stream, using an IEX chromatography column. The gel image depicts the IEX load and the fractions collected across the purification. Neutral protease elutes at the end of the gradient and is observed in fraction 3. The N-terminus of all impurities were determined by Edman degradation and liquid chromatography-mass spectrometry (LC-MS) using purified product fragments. Thermolysin was used as a model protease to determine if the cleavage termini matched a thermolysin cleavage site in the protein analytical program Peptide Cutter at expasy.org. In all cases the cleavage termini were hits for thermolysin cleavage. The purified neutral protease was sequenced by Edman degradation and LC-MS to identify the current process neutral protease N-terminus. This was also used for degradation studies to confirm that the process isolated neutral protease is functional (active).

FIG. 31 is the deduced genomic sequence of *C. histolyticum* (CCH) neutral protease (δ-toxin, CHL_2576) (SEQ ID NO: 3). The underlined sequence identifies the N-terminus of the mature neutral protease from *C. histolyticum* strain 004 as identified by Edman degradation testing. The bold sequence identifies the section of the mature neutral protease from *C. histolyticum* as detected by Lys-C/Trypsin LC-mass spec.

Figure 32:
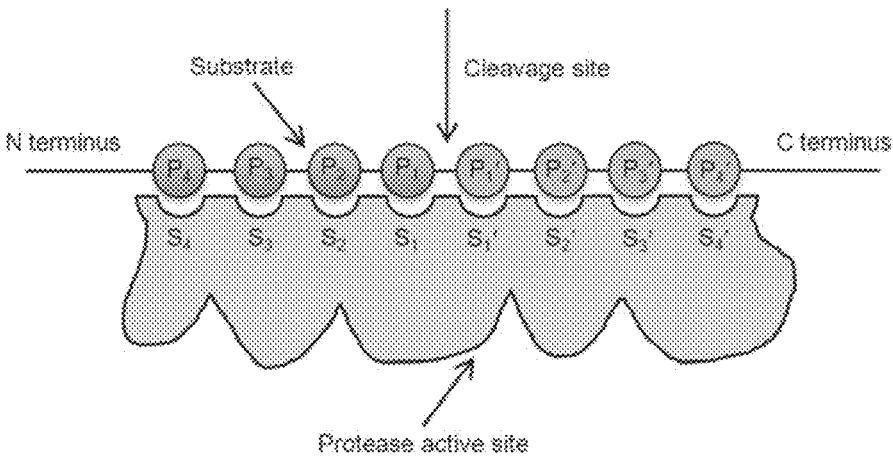

FIG. 32 describes the Schechter and Berger protease subsite nomenclature.

FIG. 33 is a sequence alignment of ,npr A (SEQ ID NO: 2) and collagenase *C. histolyticum* (abbreviated CCH) neutral protease (CLH_2576) (SEQ ID NO: 3), showing complete homology between the two enzymes.

Figure 34:
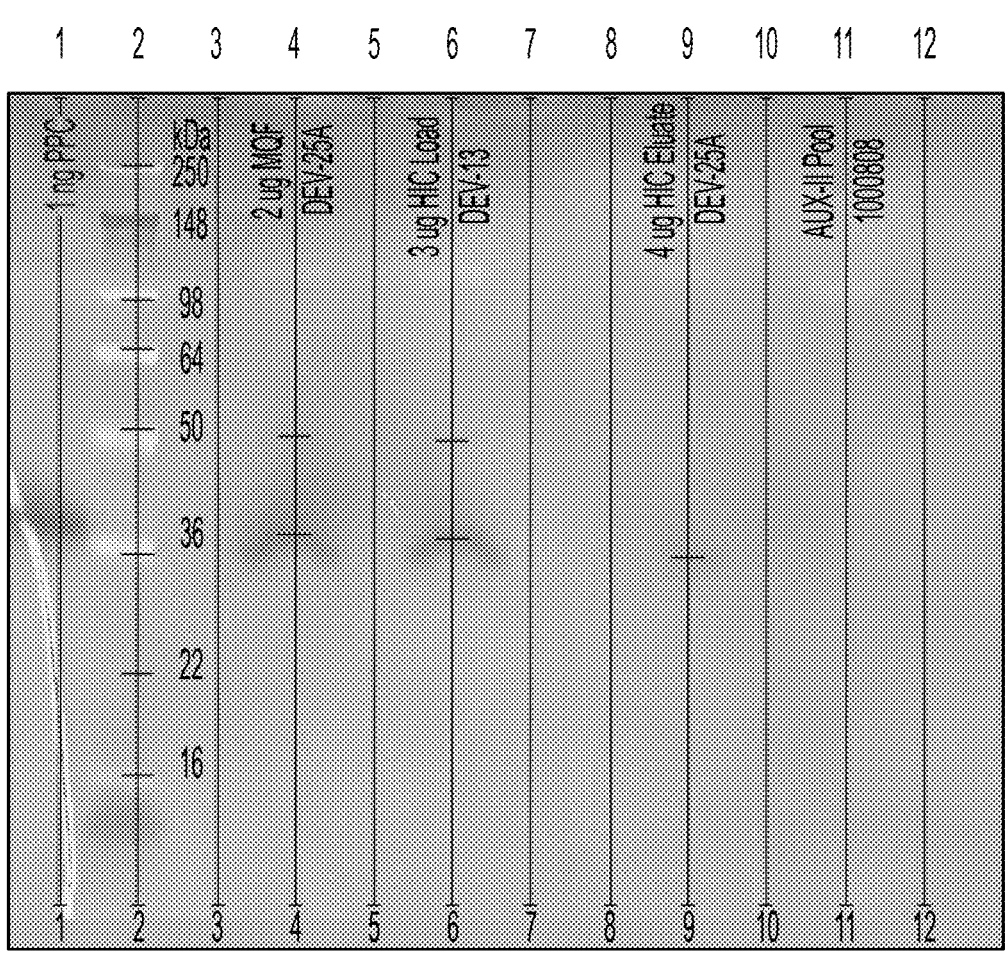

FIG. 34 is a 12% Tris-Glycine Novex® casein Zymography PAGE image of *C. histolyticum* (CCH) in-process product streams: Mustang-Q Filtrate (MQF), HIC Load, HIC Eluate, and AUX-II Pool from Lot 100808. The gel used is a 12% Tris-Glycine Novex® Zymogram casein gel. The manufacturing process that generated Lot 100808 generated high levels of impurities and used the old method of process control. The neutral protease activity is observed in this image in the MQF, HIC Load, and HIC Eluate, but not in the AUX-II Pool. The low signal observed in the HIC Eluate sample indicates the primary clearance of neutral protease occurs at the HIC step.

Figure 35:
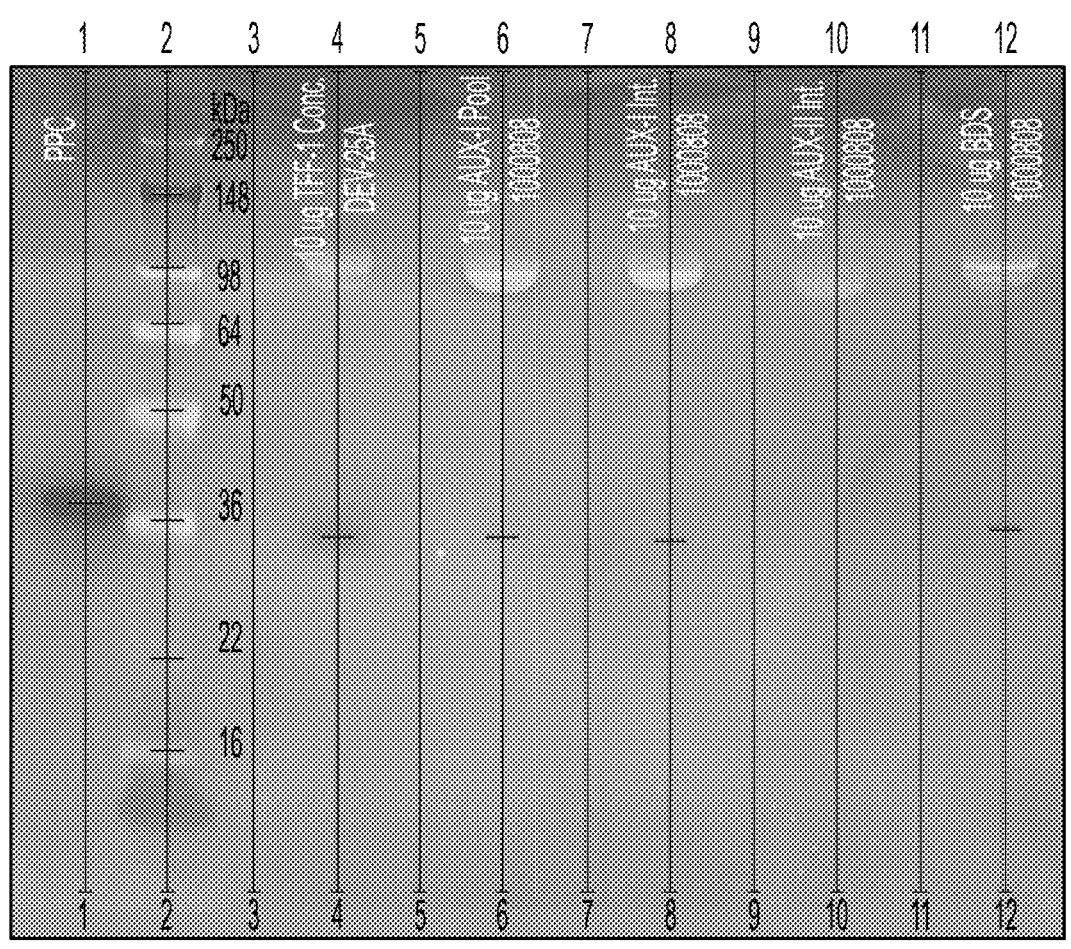

Lane 1: +Control (thermolysin), 1 ng
Lane 2: Molecular Weight Reference
Lane 3: Blank
Lane 4: MQF Dev-25A, 2
Lane 5: Blank
Lane 6: HIC Load Dev-13, 3
Lane 7: Blank
Lane 8: Blank
Lane 9: HIC Eluate Dev-25A, 4
Lane 10: Blank
Lane 11: Aux II Pool 1000808, 10
Lane 12: Blank FIG. 35 is a 12% Tris-Glycine Novex® casein Zymography PAGE image of *C. histolyticum* (CCH) in-process product streams: the first tangential flow filter (TFF-1) concentrate, AUX-I Pool, AUX-I Intermediate, AUX-II Intermediate, drug product from a lot impacted by the HIC buffers with high zinc and nickel content. The gel used is 12% Tris-Glycine Novex® Zymogram casein gel. In this case, neutral protease was observed in the TFF-1 concentrate, and in low levels of the AUX-I and drug product, but not in the AUX-II. These data demonstrate neutral protease separation from the product across the IEX step, eluting with the AUX-I.

Figure 36:
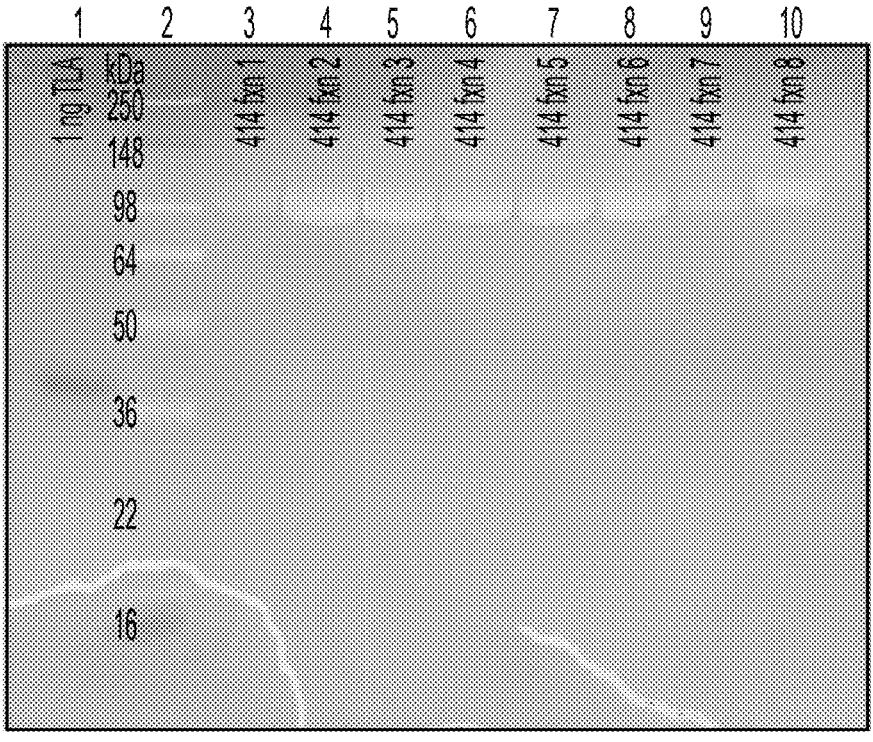

Lane 1: +Control (Thermolysin), 1 ng
Lane 2: Molecular Weight Reference
Lane 3: Blank
Lane 4: TFF-1 Conc. 10000808, 10 µg
Lane 5: Blank
Lane 6: AUX-I Pool 10000808, 10 µg
Lane 7: Blank
Lane 8: AUX-I Int. 10000808, 10 µg
Lane 9: Blank
Lane 10: AUX-II Int. 10000808, 10 µg
Lane 11: Blank
Lane 12: Drug substance 10000808, 10 µg FIG. 36 is a 12% Tris-Glycine Novex® casein Zymography PAGE image of collagenase *C. histolyticum* (CCH) IEX fraction retains of lot 1000414 AUX-II fractions. The gel used is 12% Tris-Glycine Novex® Zymogram casein gel. These fractions were from a manufacturing lot produced prior to the discovery of active neutral protease in the process. Neutral protease was not detected in any of the AUX-II fractions.

Figure 37:
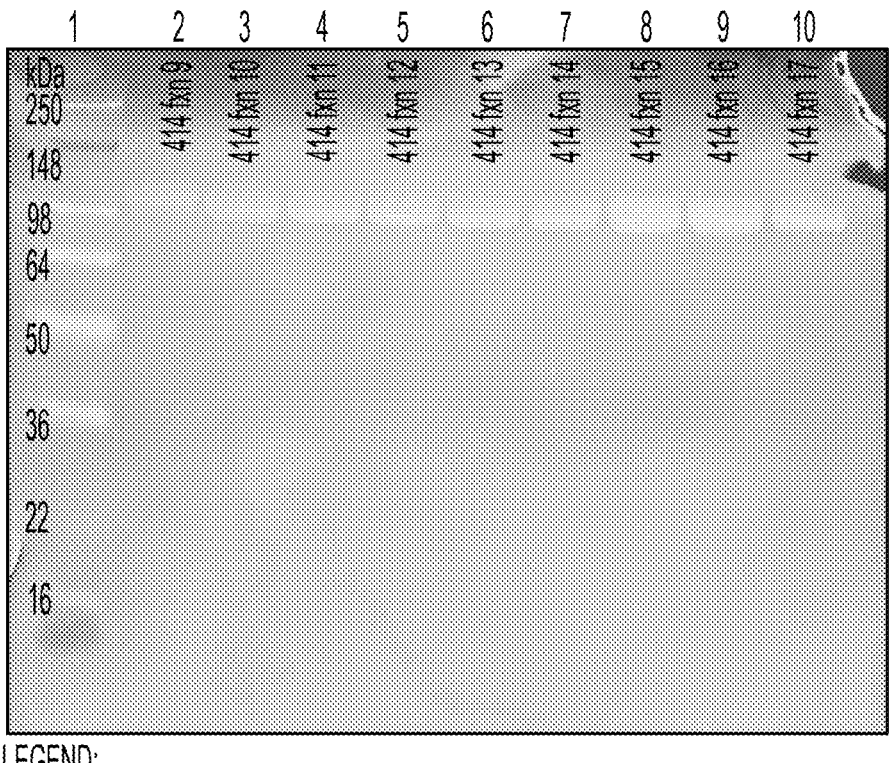

Lane 1: +Control (thermolysin), 1 ng
Lane 2: Molecular Weight Reference
Lane 3: AUX-II Fxn 1 1000414, 6.4 µg
Lane 4: AUX-II Fxn 2 1000414, 14.4 µg
Lane 5: AUX-II Fxn 3 1000414, 10 µg
Lane 6: AUX-II Fxn 4 1000414, 10 µg
Lane 7: AUX-II Fxn 5 1000414, 10 µg
Lane 8: AUX-II Fxn 6 1000414, 11.2 µg
Lane 9: AUX-II Fxn 7 1000414, 6.2 µg
Lane 10: AUX-II Fxn 8 1000414, 5.8 µg FIG. 37 is a 12% Tris-Glycine Novex® casein Zymography PAGE image of collagenase *C. histolyticum* (CCH) IEX fraction retains of Lot 1000414 AUX-I fractions. The gel used is 12% Tris-Glycine Novex® Zymogram casein gel. These fractions were from a manufacturing lot produced prior to the discovery of active neutral protease in the process. Neutral protease was not detected in any of the AUX-I fractions using this method.

Figure 16:
FIG. 16 shows the frequency of impurity occurrence by fraction and the mean and range of relative percent quantity of impurity by fraction for the AUX-II 96 kD impurity.
Figure 17:
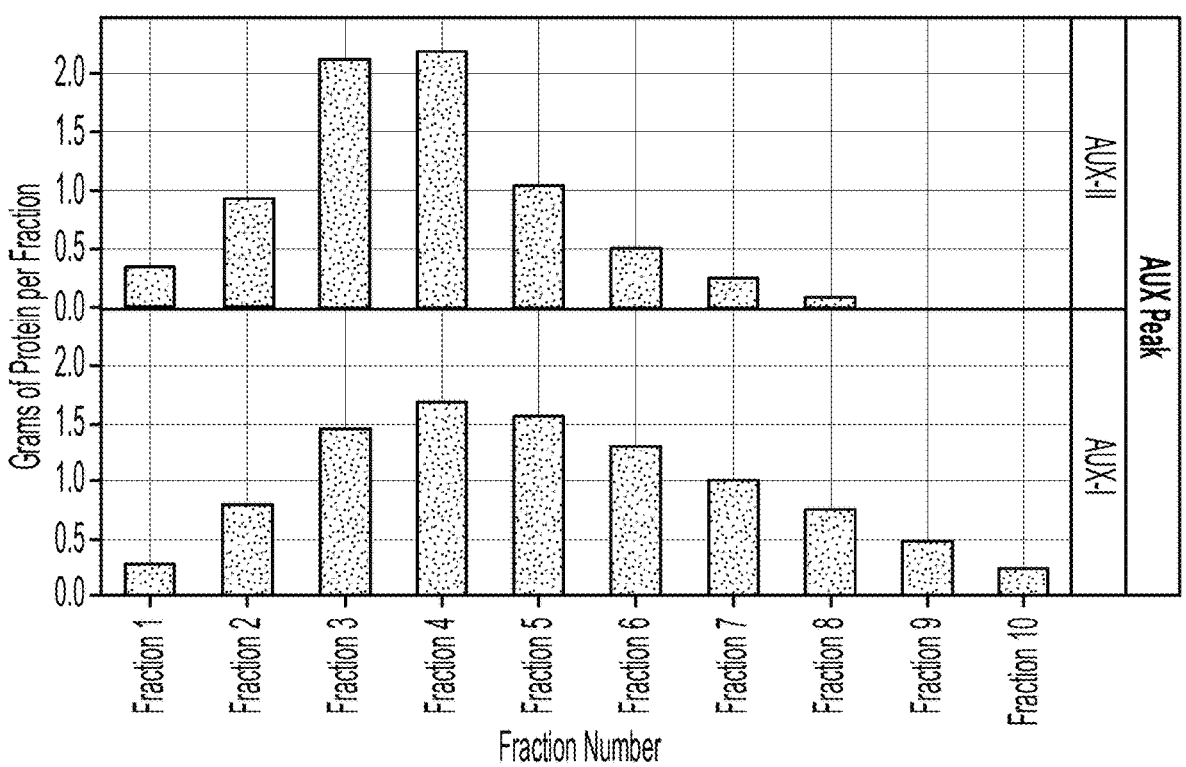
FIG. 17 illustrates a typical grams of protein per IEX fraction.
Figure 38:
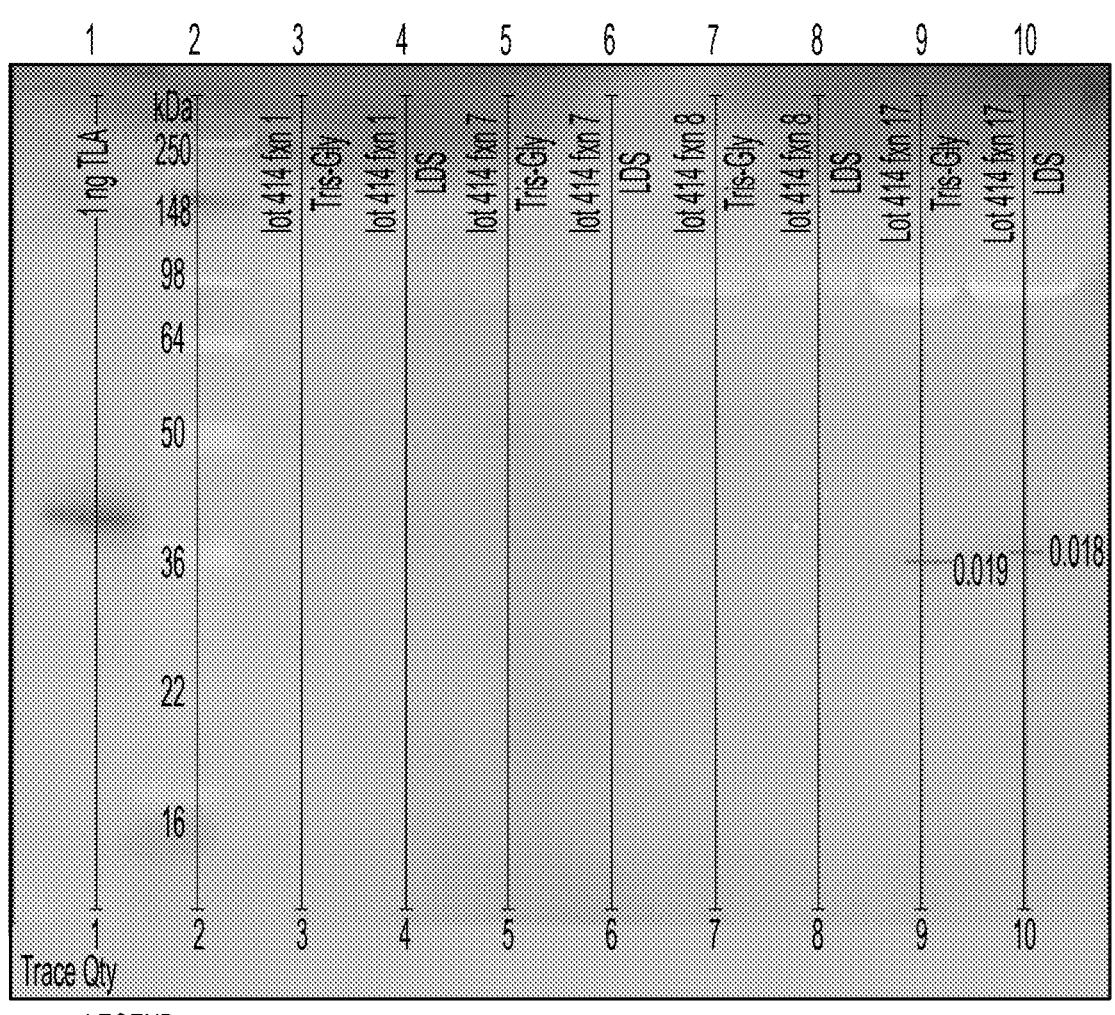

Lane 1: Molecular Weight Reference
Lane 2: AUX-I Fxn 9 1000414, 8.8 µg
Lane 3: AUX-I Fxn 10 1000414, 10 µg
Lane 4: AUX-I Fxn 11 1000414, 10 µg
Lane 5: AUX-I Fxn 12 1000414, 10 µg
Lane 6: AUX-I Fxn 13 1000414, 10 µg
Lane 7: AUX-I Fxn 14 1000414, 10 µg
Lane 8: AUX-I Fxn 15 1000414, 10 µg
Lane 9: AUX-I Fxn 16 1000414, 14 µg
Lane 10: AUX-I Fxn 17 1000414, 10 µg FIG. 38 is a 12% Tris-Glycine Novex® casein Zymography PAGE image of collagenase *C. histolyticum* (CCH) IEX fraction retains of Lot 1000414 AUX-II fractions 1, 7 and AUX-I fractions 8, 17. The gel used is 12% Tris-Glycine Novex® Zymogram casein gel. The manufacturing process that generated Lot 1000414 resulted in low levels of impurities and used the old method of process control. On this gel, the fractions were run at higher concentrations than in the original gels (FIGS. 16 and 17). Neutral protease was only detected in the last fraction of the AUX-I peak (fraction 17), demonstrating its positional nature in eluting at the end of the peak.

Lane 1: +Control (thermolysin), 1 ng
Lane 2: Molecular Weight Reference
Lane 3: AUX-II Fxn 1 1000414 Tris-Gly, 10 µg
Lane 4: AUX-II Fxn 1 1000414 LDS, 10 µg
Lane 5: AUX-II Fxn 7 1000414 Tris-Gly, 9.3 µg
Lane 6: AUX-II Fxn 7 1000414 LDS, 9.3 µg
Lane 7: AUX-I Fxn 8 1000414 Tris-Gly, 6.5 µg
Lane 8: AUX-I Fxn 8 1000414 LDS, 6.5 µg
Lane 9: AUX-I Fxn 17 1000414 Tris-Gly, 11 µg
Lane 10: AUX-I Fxn 17 1000414 LDS, 11 µg Tris-Gly and LDS are two buffer systems for SDS-PAGE. This gel was run to evaluate if one system was superior to the other. No differences noted.

Figure 39:
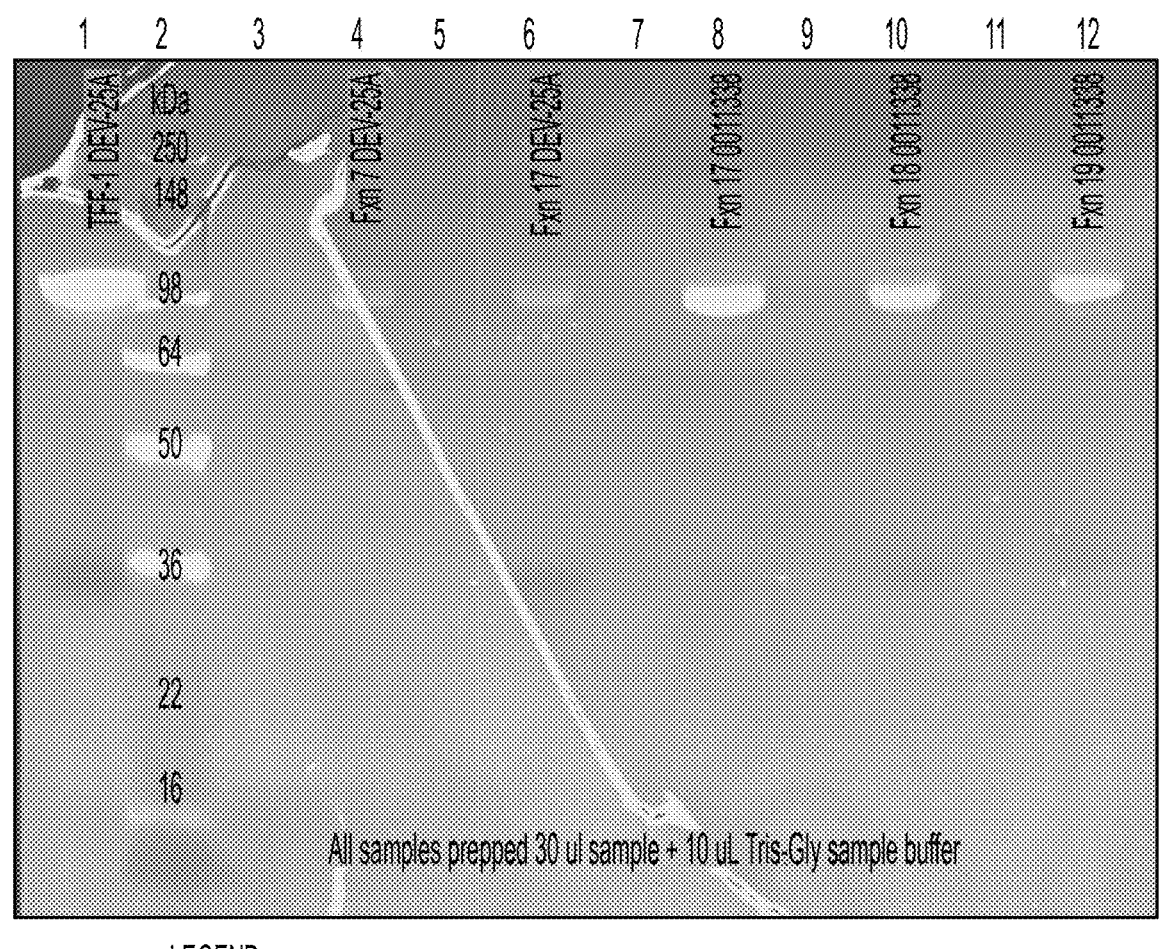

FIG. 39 is a 12% Tris-Glycine Novex® casein Zymography PAGE image of collagenase *C. histolyticum* (CCH) IEX fraction retains of Lot 001138 AUX-I tail fractions 17, 18, 19. The gel used is 12% Tris-Glycine Novex® Zymogram casein gel. This gel depicts rejected fractions from the end of the AUX-I peak. Each of the three rejected fractions contained detectable neutral protease. Fractions 17 and 18 passed the in process pooling criterion but were rejected based on the 1:1 yield target pooling strategy. This demonstrates the process controls that remove residual neutral protease from the AUX-I and drug product.

Figure 40:
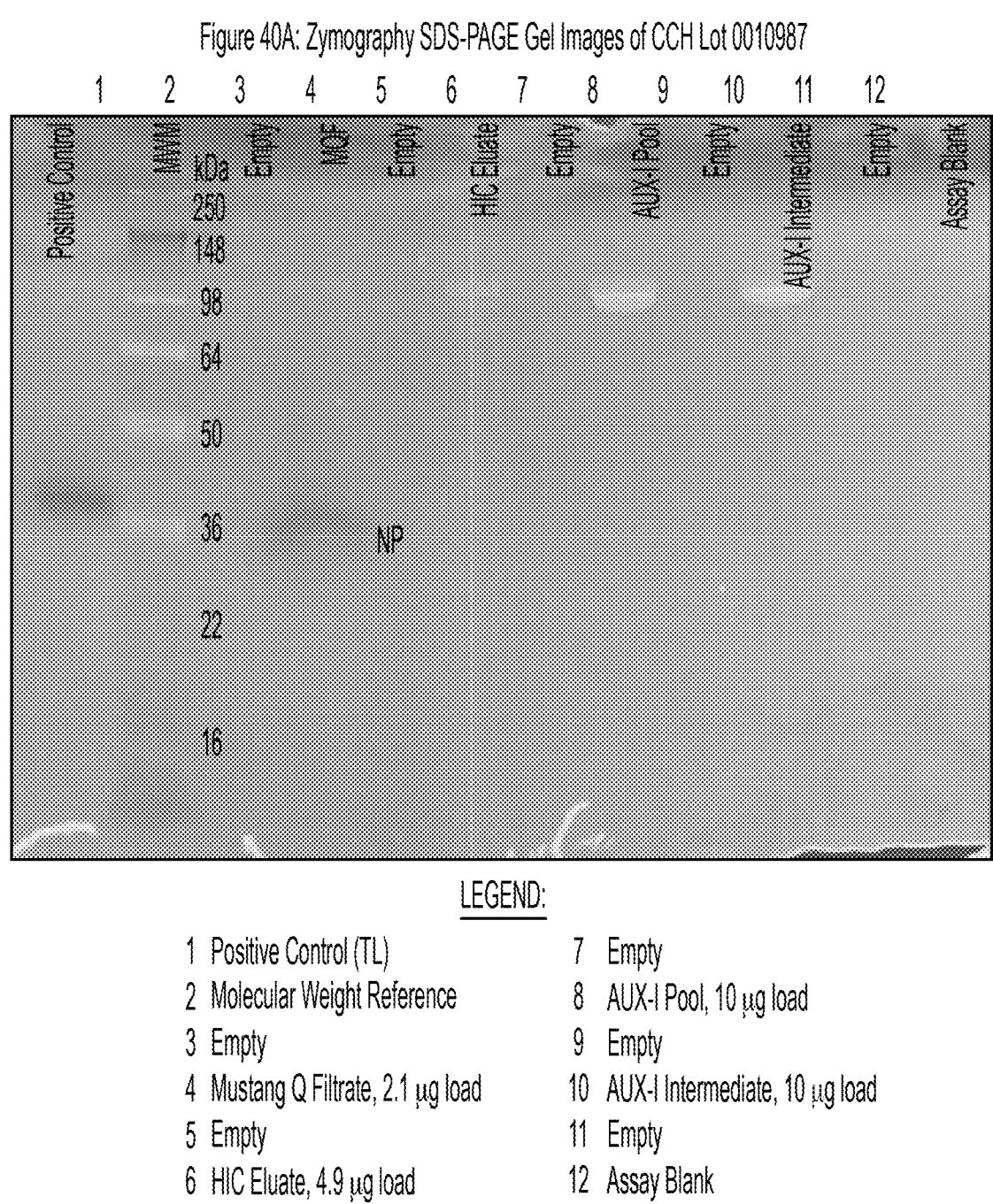

Lane 1: TFF-1 Conc. Dev-25A, 34 µg
Lane 2: Molecular Weight Reference
Lane 3: Blank
Lane 4: AUX-1 Fxn 7 Dev-25A, 4.5 µg
Lane 5: Blank
Lane 6: AUX-I Fxn 17 Dev-25A, 5 µg
Lane 7: Blank
Lane 8: AUX-I Fxn 17 001138, 14.8 µg
Lane 9: Blank
Lane 10: AUX-I Fxn 18 001138, 10.3 µg
Lane 11: Blank
Lane 12: AUX-I Fxn 19 001138, 8.1 µg FIG. 40A and FIG. 40B are 12% Tris-Glycine Novex® casein Zymography SDS-PAGE gel images of collagenase *C. histolyticum* (CCH) manufacturing process Lot 0010987. The gel used is 12% Tris-Glycine Novex® Zymogram casein gel. This gel depicts rejected fractions from the end of the AUX-I peak. Each of the three rejected fractions contained detectable neutral protease. Fractions 17 and 18 passed the in process pooling criterion but were rejected based on the 1:1 yield target pooling strategy. This demonstrates the process controls that remove residual neutral protease from the AUX-I and drug product. FIG. 40A shows the state of purification for AUX-1 throughout the process. FIG. 40B shows the state of purification for AUX-II throughout the process.

FIG. 40A
Lane 1: Positive Control (TL)
Lane 2: Molecular Weight Reference
Lane 3: Empty
Lane 4: Mustang Q Filtrate, 2.1 µg load
Lane 5: Empty
Lane 6: HIC Eluate, 4.9 µg load
Lane 7: Empty
Lane 8: AUX-I Pool, 10 µg load
Lane 9: Empty
Lane 10: AUX-I Intermediate, 10 µg load
Lane 11: Empty
Lane 12: Assay Blank
FIG. 40B
Lane 1: Positive Control (TL)
Lane 2: Molecular Weight Reference
Lane 3: Empty
Lane 4: TFF-1 Concentration, 10 µg load
Lane 5: Empty
Lane 6: AUX-II Pool, 10 µg load
Lane 7: Empty
Lane 8: AUX-II Intermediate, 10 µg load
Lane 9: Empty
Lane 10: Bulk Drug Substance (drug product), 10 µg load
Lane 11: Empty
Lane 12: Assay Blank FIG. 41 depicts collections of collagenase I fractions and collagenase II and forward processing them based on meeting the purity criteria.

Figure 42:
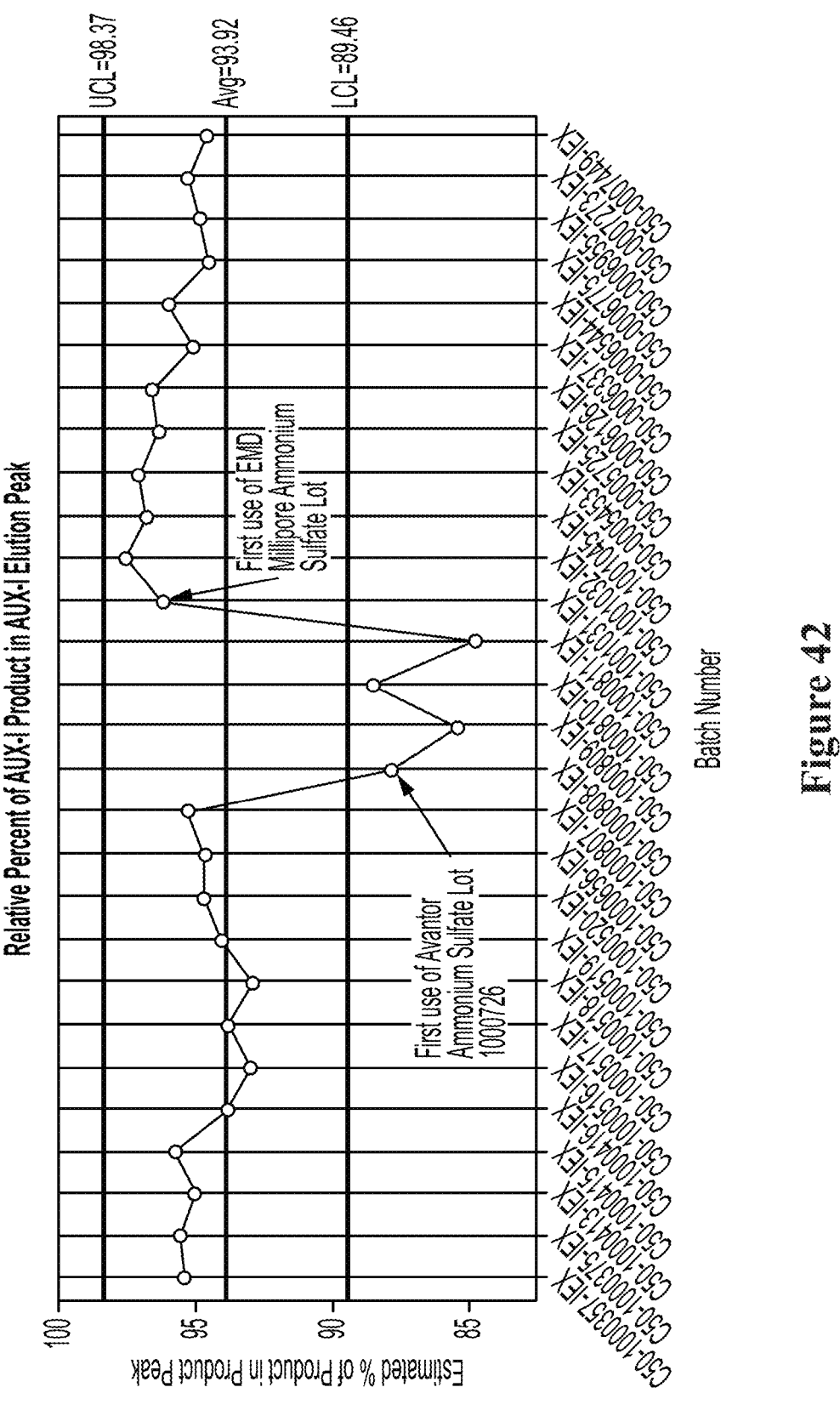

FIG. 42 provides the percent purity of the AUX-I product relative to the quantity of the total protein in each AUX elution peak.

Figure 43:
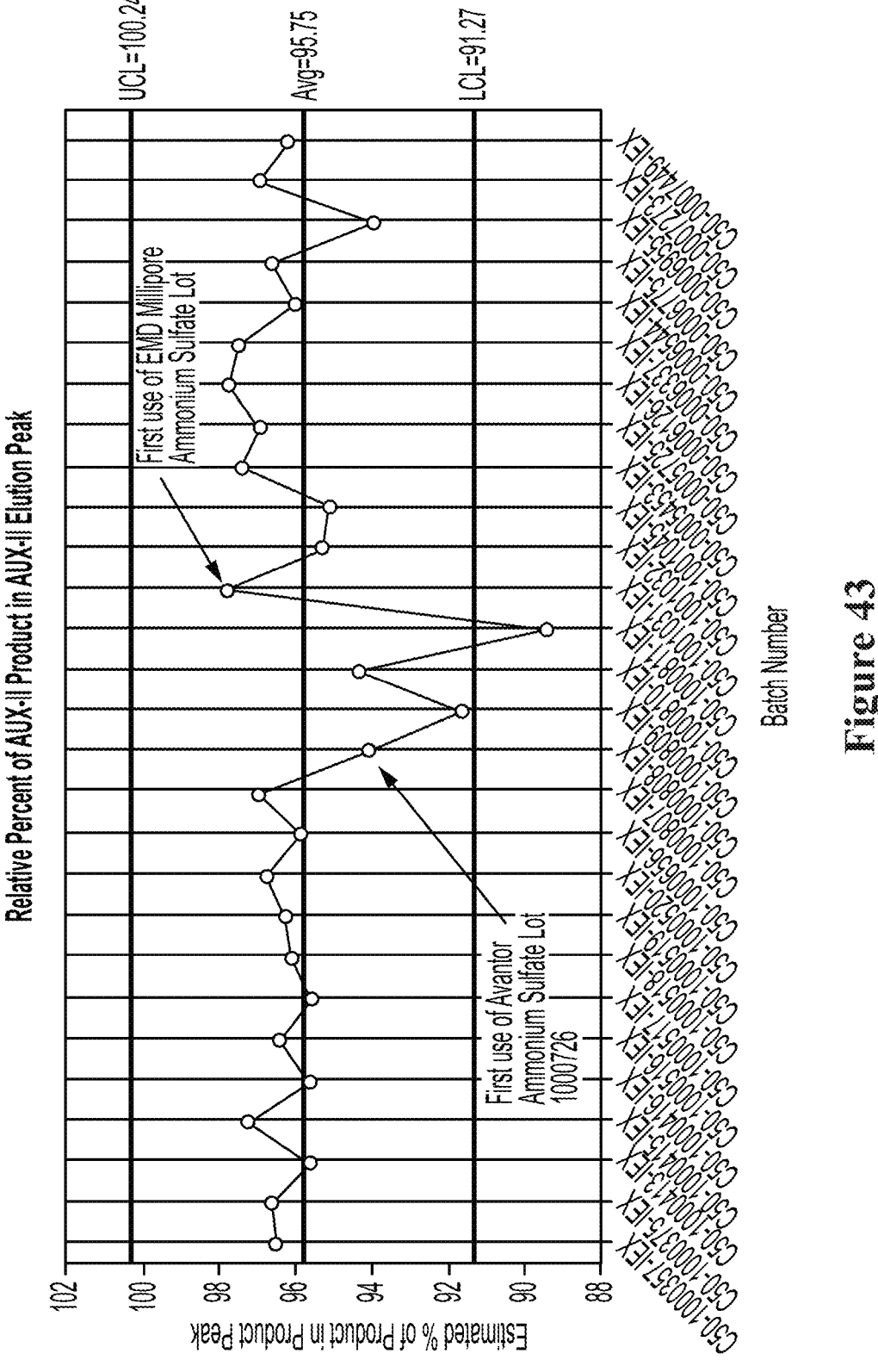

FIG. 43 provides the percent purity of the AUX-II product relative to the quantity of the total protein in each AUX elution peak.

Figure 44:
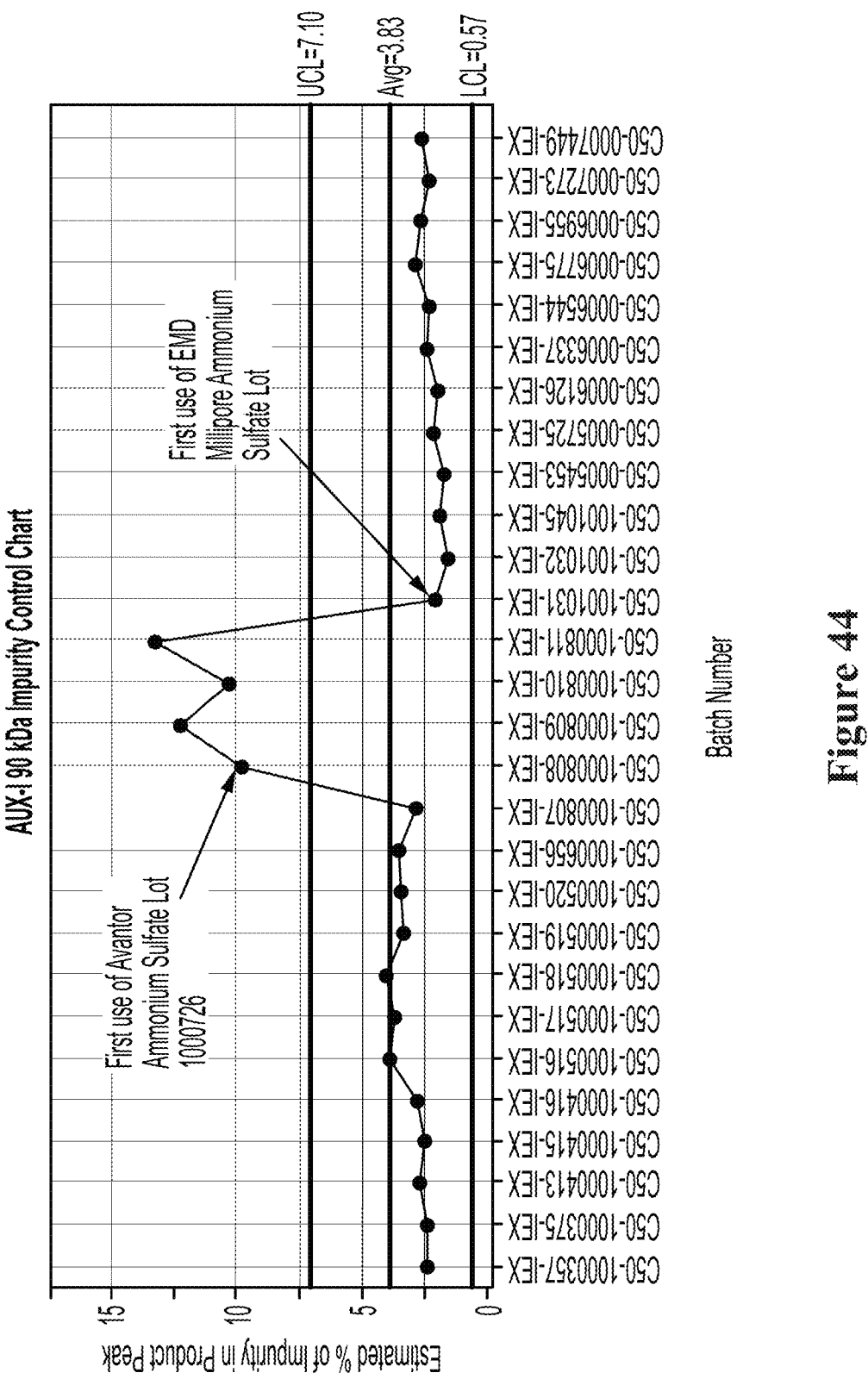

FIG. 44 represents the control chart of the AUX-I 90 kDa Impurity. The decrease in percent purity levels of the AUX-I elution peaks seen in FIG. 42 is primarily due to elevated levels of the AUX-I 90 kDa impurities.

Figure 45:
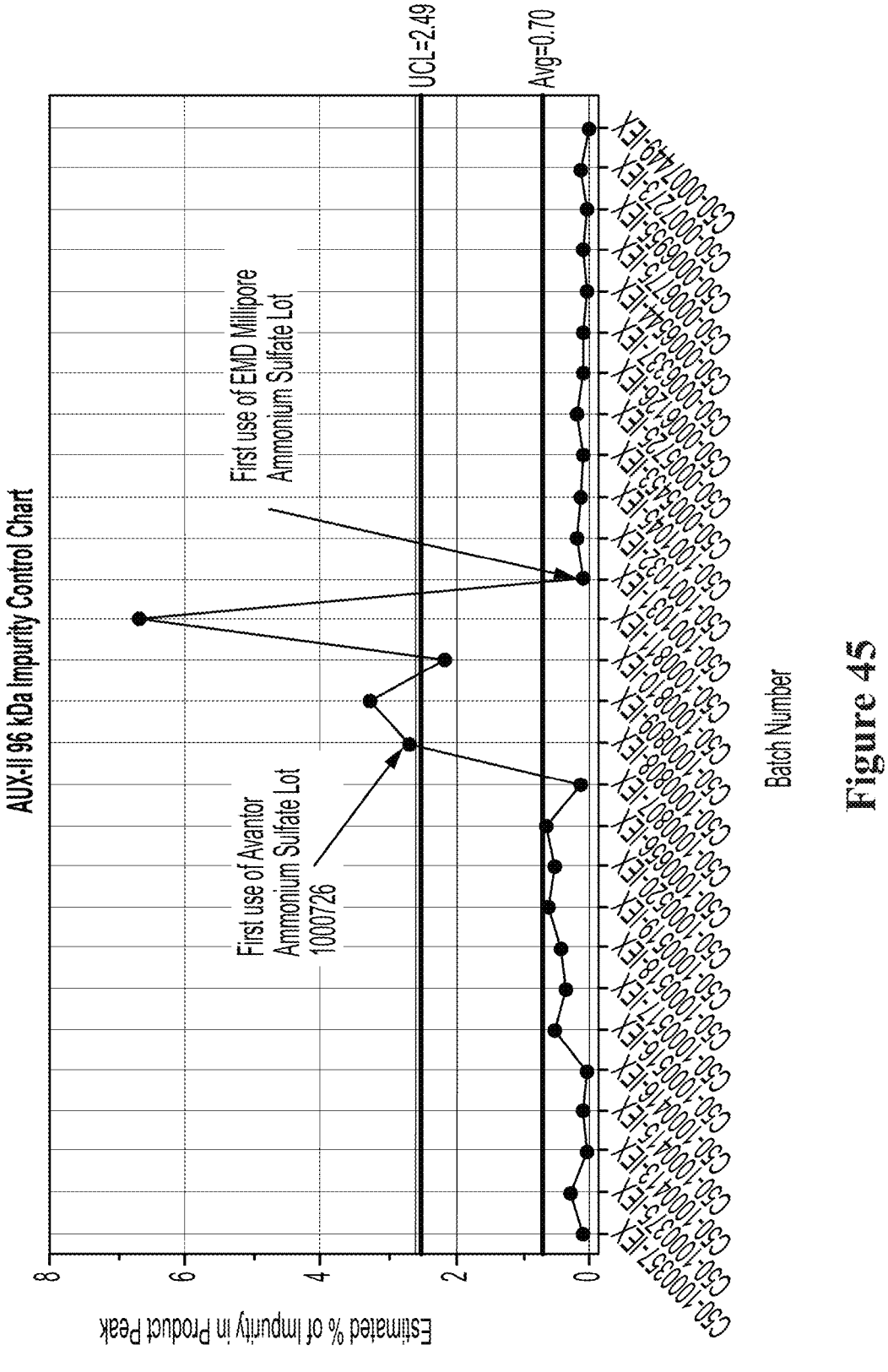

FIG. 45 represents the control chart of the AUX-II 96 kDa Impurity. The decrease in percent purity levels of the AUX-II elution peaks seen in FIG. 43 is primarily due to elevated levels of the AUX-II 96 kDa impurities.

FIG. 46A, FIG. 46B, FIG. 46C, and FIG. 46D provide the estimated percent in product peak for the various AUX peaks and bands. The data provided by these figures was used in the statistical analysis for the assessment of IEX fraction impurities after the implementation of corrective and preventive actions associated with deviation 3797.

DETAILED DESCRIPTION OF THE SPECIFIC EMBODIMENTS

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art. All publications, patents and patent applications cited herein, whether supra or infra, are hereby incorporated by reference in their entirety.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, and each separate value is incorporated into the specification as if it were individually recited herein.

As used herein, "collagenase" is meant to include one or more proteins exhibiting collagenase activity in a standard collagenase assay, for example a collagenase I and/or a collagenase II. The collagenase composition may comprise at least one of two microbial collagenases, sometimes called AUX I and AUX II. The terms "Collagenase I," "ABC I," "AUX I," "AUX-I," "collagenase AUX I," and "collagenase ABC I" mean the same enzyme with the same amino acid sequence and can be used interchangeably. Similarly, the terms "Collagenase II," "ABC II," "AUX II," "AUX-II," "collagenase AUX II," and "collagenase ABC II" refer to the same enzyme and can also be used interchangeably. These collagenases are secreted by bacterial cells. In certain aspects, collagenase is isolated and purified from *C. histolyticum* culture supernatant by chromatographic methods. In other aspects, collagenase is isolated and purified recombinantly, and/or obtained from a variety of sources including mammalian, fungal, and bacterial sources. Both collagenases are special proteases and share the same EC number (E.C 3.4.24.3). In other aspects, the collagenase composition comprises collagenase I or collagenase II. In other embodiments, the collagenase composition comprises both collagenase I and collagenase II.

A "collagen mediated condition" as used herein means any disease or ailment that involves collagen. Examples of collagen mediated-conditions that may be treated by the compositions and methods described herein include, but are not limited to: Dupuytren's disease; Peyronie's disease; frozen shoulder (adhesive capsulitis), keloids; hypertrophic scars; depressed scars such as those resulting from inflammatory acne; post-surgical adhesions; acne vulgaris; lipomas, and disfiguring conditions such as wrinkling, cellulite and neoplastic fibrosis.

The phrase "collagenase I product" means collagenase I that has been purified from a fermentation, wherein the elution of collagenase I from a step in the purification has been collected in fractions, and any number of those fractions have been pooled together.

The phrase "collagenase II product" means collagenase II that has been purified from a fermentation, wherein the elution of collagenase II from a step in the purification has been collected in fractions, and any number of those fractions have been pooled together.

The phrase "derived from" *Clostridium histolyticum* means collagenase originating from *C. histolyticum*. It encompasses both collagenase obtained from fermentations of *C. histolyticum* and fermentations using other organisms having recombinant collagenases.

It is understood that the terms "drug substance," "drug product" or "collagenase composition" can be used interchangeably and refers to collagenase I, collagenase II, or both collagenase I and collagenase II compositions before any optional lyophilization occurs.

"Essentially free of neutral protease" as used herein means below the detectable limit of the particular detection assay employed (e.g., SDS PAGE, Zymography, HPLC etc.).

"Forward processed" as used herein means fractions of highly purified collagenase I or II used in pooling to create final collagenase I drug substance or collagenase II drug substance.

"Highly purified" or "high purity" or "highly pure" collagenase I or II, or combination of collagenase I and II as used herein means collagenase that is at least 95% pure by area, or at least 96% pure by area, or at least 97% pure by area, or at least 98% pure by area, or at least 99% pure by area, or about 100% pure by area, as determined by reverse-phase HPLC (RP-HPLC). To further clarify, this includes all numerical values for purity between at least 95% by area and about 100% by area as determined by RP-HPLC.

"Most abundant impurity" as used herein means the collagenase fragment having the highest presence in a given step (e.g., after IEX) as measured by SDS-PAGE gel with or without densitometry, or as measured by another acceptable method. Collagenase fragments may be found throughout the purification process and may be any size, but most frequently are found at molecular weights of about 33 kDa, 45 kDa, 55 kDa, 80 kDa, or 90 kDa for collagenase I fragments, and about 25 kDa, 38 kDa, 50 kDa, 60 kDa, 80 kDa, 90 kDa, 92 kDa, 92 kDa, or 96 kDa for collagenase II fragments.

"Neutral protease elimination" or "neutral protease elimination step" as used herein means the removal or rejection of fractions collected during manufacturing after the collagenase filtrate is passed through a separation column or filter.

"Optional" or "optionally" means that the subsequently described element, component or circumstance may or may not occur, so that the description includes instances where the element, component, or circumstance occurs and instances where it does not.

As used herein, the term "pharmaceutically acceptable carrier" or "excipient" means a non-toxic, inert solid, semi-solid or liquid filler, diluent, encapsulating material or formulation auxiliary. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, perfuming agents, preservatives and antioxidants can also be present in the composition, according to the judgment of the formulator.

"Purified fraction" as used herein means the undegraded collagenase I has at least about 90% purity as measured by SDS-PAGE gel densitometry, and the most abundant degraded collagenase I or II impurity is at no more than 7.5%. For collagenase II fractions from a collagenase manufacturing process step to qualify as a "purified fraction," undegraded collagenase II has at least about 90% purity as measured by SDS-PAGE gel densitometry, and the most abundant degraded collagenase I or II impurity is at no more than 7.5%. For example, a purified collagenase I fraction may have undegraded AUX-I of at least about 90% or about 91.2% as measured by SDS-PAGE gel densitometry and the most abundant degraded AUX-I or AUX-II impurity is at no more than about 5% or about 5.8% as measured by SDS-PAGE gel densitometry. As a second example, for an AUX-II fraction to qualify as a purified fraction, the fraction may have at least about 90% or about 91.2% purity of undegraded AUX-II as measured by SDS-PAGE gel densitometry, and the most abundant degraded AUX-I or AUX-II impurity at no more than about 5% or about 5.8% purity as measured by SDS-PAGE gel densitometry.

The terms "subject" or "patient" is used interchangeably herein and refers to a human or other mammal.

Collagenase can be generated by a variety of fermentation methods known to those skilled in the art. Crude collagenase obtained from C. histolyticum has previously been purified by a variety of methods including dye ligand affinity chromatography, heparin affinity chromatography, ammonium sulfate precipitation, hydroxylapatite chromatography, size exclusion chromatography, ion exchange chromatography, and metal chelation chromatography. Crude and partially purified collagenase is commercially available from many sources including Sigma Aldrich (SIAL-Millipore) and Advance Biofactures Corp., Lynbrook, N.Y. Methods of fermentation and purification of crude collagenase obtained from C. histolyticum are also described in U.S. Pat. No. 7,811,560.

As detailed below, the present invention provides improved methods to manufacture of collagenase products by (a) controlling for the metal content during purification;

and (b) reducing or eliminating neutral protease from the final collagenase products, e.g., collagenase I and collagenase II drug substances. The present disclosure has general applicability to the manufacture and use of collagenases regardless of source. It is not intended to be limited to collagenase I and II derived from C. histolyticum.

Improved Manufacture of Collagenase

In a general aspect of the inventive method of manufacturing highly pure collagenase (e.g., collagenase I and II drug substances), the method comprises the steps of: (1) fermenting a bacteria that secretes at least collagenase(s) and neutral protease into the liquid fermentation media; (2) purifying the collagenase from the media (optionally including treatment with a high salt composition); (3) separating collagenase I and collagenase II from each other; (4) reducing or eliminating neutral protease from one or both of the collagenase I and collagenase II portions so they are essentially free of neutral protease; and (5) generating a highly pure collagenase drug substance post-removal of neutral protease. Optionally, pharmaceutically acceptable excipients are added to such drug substance to form a pharmaceutical formulation as described elsewhere herein.

Fermentation to Create Collagenases Such as Collagenase I and Collagenase II

The present disclosure encompasses the fermentation of any bacteria that secretes collagenase into fermentation media. Examples of such fermentations include those from *Actinomadura madurae, Actinobacillus actinomycetemcomitans, Bacillus cereus, Clostridium histolyticum, Clostridium perfringens, Streptococcus mutans, Staphylococcus* spp., *Vibrio alginolyticus,* and *Vibrio vulnificus.* This list is not exhaustive and other bacterial organisms that secrete collagenases can be used that are known to those skilled in the art. See, e.g., U.S. Pat. No. 7,811,560. The proteins secreted by *C. histolyticum* include type I and type II collagenases, and various toxins (e.g., neutral protease, clostripain, aerolysin-like hemolysin, and oxygen labile hemolysin).

Fermentation media may be any media into which collagenases are secreted. The fermentation media may include a carbon-source, a nitrogen-source, salts, micronutrients and water. Carbon-sources are not limited, but may include sugars or other carbohydrates. Nitrogen sources are not limited, but may include meals such as soy meal, or may include extracts such as yeast extract, or may include pre-digested polypeptides, such as peptones or tryptones. Peptones may be derived from animals, such as bovine-derived media or porcine-derived media. Peptones may be derived from sources other than animals, such as vegetable-derived or other plant-derived.

Purification of Collagenase I and Collagenase II

Common purification techniques include, but are not limited to, filters, chromatography, and precipitations. Certain aspects of the purification of collagenase I and II from *C. histolyticum* can be performed as is known in the art. See, e.g., U.S. Pat. No. 7,811,560.

The collagenase purification process may further include at least one of the following steps: (1) controlling for zinc and/or nickel concentrations in at least the first anion exchange step, the HIC step, and the first buffer exchange step; (2) discarding the latter fractions of AUX-I from either anion exchange step; (3) after separating collagenase I from collagenase II, pooling peak fractions of collagenase I only until the amount of collagenase I pooled from peak fractions is approximately equal to the amount of collagenase II from the manufacturing process, and (4) setting purity criteria for the pooling step of collagenase I, collagenase II, or both collagenase I and collagenase II. The employment of these steps produces a collagenase I product essentially free of neutral protease. Likewise, collagenase II product is essentially free of neutral protease.

Filtering the collagenases and toxins from the media may be accomplished in a number of ways, such as through the use of a depth filter, centrifugation, microfiltration, tangential flow filtration, diatomaceous earth filter beds, and vacuum filtration. In one embodiment, filtering is performed using a depth filter followed by a 0.2 micron sterilization grade filter.

In one embodiment, the purification process may include harvesting collagenase from fermented *C. histolyticum* (e.g., a porcine-derived media such as proteose peptone) through a depth filter (e.g., a Millipore Millistak HC POD), followed by anion exchange filtration (e.g., a Mustang Q filter), followed by filtration (e.g., a 0.45 □ filter) and adjustment of the filtrate by exposing it to a high salt composition (e.g., ammonium sulfate) in a concentration of about 0.8 M-1.2 M, followed by a hydrophobic interaction chromatography column (e.g., phenyl SFF low-sub), followed by buffer-exchange (e.g., tangential flow filtration or dialysis), followed by ion exchange chromatography (e.g., with a Q Sepharose HP anion exchange column), followed by buffer-exchange (e.g., tangential flow filtration or dialysis). Further, leupeptin may be added in the hydrophobic interaction chromatography step and maintained through the ion exchange step.

A high salt composition is one that allows for separation of proteins based on solubility. Salts from the Hofmeister series (lyotropic series) may be used. In some embodiments, the composition is a solution selected from the group consisting of ammonium sulfate, sodium chloride, potassium chloride, sodium sulfate or mixtures thereof. The high salt compositions can be used at various concentrations. For example, ammonium sulfate may be used at a concentration ranging from about 0.8 M to about 1.2 M, or about 0.9 M to about 1.1 M, or about 1M.

It is advantageous that the high salt composition be free of metal contaminants, or has low metal content. In some embodiments, the high salt composition meets one or more of the following specifications:

| Metal | Specification |
| --- | --- |
| Nickel | ≤0.1 ppm |
| Zinc | ≤1 ppm |
| Aluminum | ≤0.75 ppm |
| Arsenic | ≤0.2 ppm |
| Calcium | ≤10 ppm |
| Cadmium | ≤1 ppm |
| Chromium | ≤0.75 ppm |
| Copper | ≤1 ppm |
| Iron | ≤2 ppm |
| Magnesium | ≤5 ppm |
| Lead | ≤2 ppm |

In other embodiments, the high salt composition may have zinc present in an amount less than about 85 ppm, or 80 ppm, or 75 ppm, or 70 ppm, or 65 ppm, or 60 ppm, or 55 ppm, or 50 ppm, or 45 ppm, or 40 ppm, or 35 ppm, or 30 ppm, or 25 ppm, or 20 ppm, or 15 ppm, or 10 ppm, or 9 ppm, or 8 ppm, or 7 ppm, or 6 ppm, or 5 ppm, or 4 ppm, or 3 ppm, or 2 ppm, or 1 ppm. Nickel may be present in the high salt composition in an amount less than about 1.5 ppm, or 1.4 ppm, or 1.3 ppm, or 1.2 ppm, or 1.1 ppm, or 1.0 ppm, or 0.9 ppm, or 0.8 ppm, or 0.7 ppm, or 0.6 ppm, or 0.5 ppm, or 0.4 ppm, or 0.3 ppm, or 0.2 ppm, or 0.1 ppm.

Metal content of raw materials may be controlled by sourcing ultra pure raw materials from qualified vendors. In one aspect, nickel concentrations are less than about 1.2 ppm, or zinc concentrations are less than about 84.4 ppm, or nickel concentrations are less than about 1.2 ppm and zinc concentrations are less than about 84.4 ppm. In other aspects, nickel concentrations, zinc concentrations, or both nickel and zinc concentrations are below about 0.1 ppm.

In one embodiment, collagenase I and collagenase II derived from *C. histolyticum* are isolated and purified, and the purification process controls for metal levels. In a further embodiment, collagenase I and collagenase II derived from *C. histolyticum* are isolated and purified, and the purification process controls for levels of nickel, zinc, aluminum, arsenic, calcium, cadmium, chromium, copper, iron, magnesium, lead, or a combination thereof In a further embodiment, the disclosure is directed to a method for isolation and purification of collagenase I and collagenase II derived from *C. histolyticum*, and the purification process controls for nickel and/or zinc levels.

In one embodiment of the invention, the nickel concentration during the manufacturing process for collagenase I and/or II and formation of the drug product is less than about 100 ppm, or less than about 75 ppm, or less than about 50 ppm, or less than about 40 ppm, or less than about 30 ppm, or less than about 20 ppm, or less than about 10 ppm, or less than about 5 ppm, or less than about 3.0 ppm, or less than about 2.9 ppm, or less than about 2.8 ppm, or less than about 2.7 ppm, or less than about 2.6 ppm, or less than about 2.5 ppm, or less than about 2.4 ppm, or less than about 2.3 ppm, or less than about 2.2 ppm, or less than about 2.1 ppm, or less than about 2.0 ppm, or less than about 1.9 ppm, or less than about 1.8 ppm, or less than about 1.7 ppm, or less than about 1.6 ppm, or less than about 1.5 ppm, or less than about 1.4 ppm, or less than about 1.3 ppm, or less than about 1.2 ppm, or less than about 1.1 ppm, or less than about 1.0 ppm, or less than about 0.9 ppm, or less than about 0.8 ppm, or less than about 0.7 ppm, or less than about 0.6 ppm, or less than about 0.5 ppm, or less than about 0.4 ppm, or less than about 0.3 ppm, or less than about 0.2 ppm, or less than about 0.1 ppm, or less than about 0.09 ppm, or less than about 0.08 ppm, or less than about 0.07 ppm, or less than about 0.06 ppm, or less than about 0.05 ppm, or less than about 0.04 ppm, or less than about 0.03 ppm, or less than about 0.02 ppm, or less than about 0.01 ppm.

In another embodiment of the invention, the zinc concentration during the manufacturing process for collagenase I and/or II and formation of the drug product is less than about 1000 ppm, or less than about 950 ppm, or less than about 900 ppm, or less than about 850 ppm, or less than about 800 ppm, or less than about 750 ppm, or less than about 700 ppm, or less than about 650 ppm, or less than about 600 ppm, or less than about 550 ppm, or less than about 500 ppm, or less than about 450 ppm, or less than about 400 ppm, or less than about 350 ppm, or less than about 300 ppm, or less than about 250 ppm, or less than about 200 ppm, or less than about 150 ppm, or less than about 125 ppm, or less than about 100 ppm, or less than about 95 ppm, or less than about 90 ppm, or less than about 85 ppm, or less than about 84 ppm, or less than about 80 ppm, or less than about 75 ppm, or less than about 70 ppm, or less than about 65 ppm, or less than about 60 ppm, or less than about 55 ppm, or less than about 50 ppm, or less than about 45 ppm, or less than about 40 ppm, or less than about 35 ppm, or less than about 30 ppm, or less than about 25 ppm, or less than about 20 ppm, or less than about 15 ppm, or less than about 10 ppm, or less than about 9 ppm, or less than about 8 ppm, or less than about 7 ppm, or less than about 6 ppm, or less than about 5 ppm, or less than about 4 ppm, or less than about 3 ppm, or less than about 2 ppm, or less than about 1 ppm, or less than about 0.9 ppm, or less than about 0.8 ppm, or less than about 0.7 ppm, or less than about 0.6 ppm, or less than about 0.5 ppm, or less than about 0.4 ppm, or less than about 0.3 ppm, or less than about 0.2 ppm, or less than about 0.1 ppm.

Separating Collagenase I and Collagenase II

Collagenase I and II can be separated by any technique known to those skilled in the art. For example, Collagenase I and II can be separated from each other using ion-exchange chromatography. One type of ion-exchange chromatography may be an anion-exchange column, such as a Q-Sepharose column.

Reduction or Elimination of Neutral Protease

In a general aspect, the step eliminating neutral protease occurs after the collagenases are separated from each other, if multiple collagenases are present. The collagenases are separated using ion exchange chromatography during the elution step. Collagenase elution generally occurs in peaks, where collagenase I is in one peak and collagenase II is in a second peak. Each peak may be collected as fractions over the time of each the elution peak.

Reducing or eliminating neutral protease from the collagenase I and collagenase II products may be achieved by one or more of the following elimination steps: (a) excluding any fraction that has less than about 90% collagenase I or II content and more than about 5% content of any single impurity as measured by SDS PAGE gel or HPLC; (b) excluding any fraction that has a detectable level of neutral protease as measured by SDS PAGE gel or Zymography; or (c) excluding any fraction that is calculated to contain an excess level of neutral protease. Each is described below and may be employed individually or in combination.

The fractions are not limited in size, but exemplary industrial size fractions may be less than about 200 mL, or 300 mL, or 400 mL, or 500 mL, or 600 mL, or 700 mL, or 800 mL, or 900 mL, or 1000 mL, or 1100 mL, or 1200 mL, or 1300 mL, or 1400 mL, or 1500 mL, or 1600 mL, or 1700 mL, or 1800 mL, or more.

The amount of collagenase per fraction is not limited, but exemplary industrial size fractions may include protein concentrations anywhere from between about 0.1 g/L to about 5 g/L or more, such as about 0.2 g/L, or 0.5 g/L, or 0.8 g/L, or 1.1 g/L, or 1.4 g/L, or 1.7 g/L or 2.0 g/L or 2.3 g/L, or 2.6 g/L, or 2.9 g/L, or 3.2 g/L, or 3.5 g/L, or 3.8 g/L, or 4.1 g/L, or 4.4 g/L, or 4.7 g/L, or 5.0 g/L, or 6 g/L, or 7 g/L, or 8 g/L, or 9 g/L or 10 g/L, or more.

A percent purity of collagenase may be determined for each fraction, using any method known to those skilled in the art. One exemplary method is a purity measurement using SDS-PAGE or SDS-PAGE and densitometry. Densitometry software may be any software that converts a SDS-PAGE band on a gel to an intensity amount. One example of such software is Quantity One®. SDS-PAGE gels may have any number of lanes, common numbers of lanes include 10 lanes or 15 lanes. Well sizes for each lane may vary; common well sizes hold between 15 and 50 microliters. Generally, any amount of protein that fits in the well can be loaded, but typical amounts sufficient for resolution of the product of interest is anywhere from about 0.5 to about 5 micrograms of protein.

Assaying for the presence of neutral protease in the fractions may also be performed. Any method for determining the presence of neutral protease in the fractions may be used that is known to those skilled in the art. Exemplary methods include SDS-PAGE or SDS-PAGE with densitometry as just described. Other exemplary methods include casein Zymography or casein Zymography with densitometry. Casein Zymography is an SDS-PAGE gel, typically with bovine milk casein embedded in the gel that neutral protease can act on, but collagenase cannot. Accordingly, bands in the Zymography gel containing neutral protease appear as a different color than the bands containing collagenase or other impurities. Generally, the limit of detection (LOD) for a Zymography assay relevant to the present disclosure is about 0.5 ng of protein using densitometry software and about 0.2-0.3 ng visually. However, depending on the exact method used, smaller amounts may be detected.

Generally, when testing for impurities, higher amounts of protein are loaded into the wells than are used for resolving the primary product(s) of interest. The impurity may be detected using the same amount of protein as used for the primary product of interest, but may require loading at least about 2 or 3 or 4 or 5 or 6 or 7 or 8 or 9 or 10 or 12 or 15 or 20 or more times the amount loaded in the wells to resolve or detect the primary product of interest. This is particularly true as the product of interest's purity increases. Generally, the amount of protein loaded into the well to detect neutral protease that is relevant to the present disclosure is between about 1 microgram to about 100 micrograms, such as about 5 micrograms, 8 micrograms, or 10 micrograms, or 12 micrograms, or 15 micrograms, or 20 micrograms, or 30 micrograms, or 50 micrograms, or 75 micrograms, or more.

In certain aspects, the present disclosure provides three different ways to reduce or eliminate neutral protease:

1. Elimination Strategy 1

According to this strategy, fractions that do not meet a selected specification for purity are set aside and excluded from further forward processing. Each fraction is assayed using SDS-PAGE or SDS-PAGE with densitometry, and each band in a lane on the gel corresponds to a percent of total protein loaded into the well above the lane. The bands may correspond to collagenase I or collagenase II, or may correspond to impurities in the form of fragments of collagenase or other proteins (such as neutral protease). Acceptable levels of collagenase I or collagenase II for the pooling step to create collagenase I product or collagenase II product, respectively, are at least 80% by area as measured by SDS-PAGE.

In other embodiments, an acceptable level of collagenase I for the pooling step to create collagenase I product is at least about 81%, or 82%, or 83%, or 84%, or 85%, or 86%, or 87%, or 88%, or 88.5%, or 89.0%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100% by area as measured by SDS-PAGE.

In one embodiment, an acceptable level of collagenase II for the pooling step to create collagenase II product is at least about 81%, or 82%, or 83%, or 84%, or 85%, or 86%, or 87%, or 88%, or 88.5%, or 89.0%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100% by area as measured by SDS-PAGE.

In one embodiment, an acceptable level of the most abundant impurity for the collagenase I drug substance (after purification and separation from collagenase II but before it is mixed with collagenase II) is less than about 20%, or 19%, or 18%, or 17%, or 16%, or 15%, or 14%, or 13%, or 12%, or 11%, or 10%, or 9%, or 8%, or 7%, or 6%, or 5%, or 4%, or 3%, or 2%, or 1%, or 0.75%, or 0.5%, or 0.25%, or 0.1%

(w/w) of the collagenase I drug substance as measured by SDS-PAGE. The amount of the most abundant impurity may also be measured by SDS-PAGE with densitometry.

In another embodiment, an acceptable level of the most abundant impurity for the collagenase II drug substance (after purification and separation from collagenase I but before it is mixed with collagenase I) is less than about 20%, or 19%, or 18%, or 17%, or 16%, or 15%, or 14%, or 13%, or 12%, or 11%, or 10%, or 9%, or 8%, or 7%, or 6%, or 5%, or 4%, or 3%, or 2%, or 1%, or 0.75%, or 0.5%, or 0.25%, or 0.1% (w/w) of the drug substance as measured by SDS-PAGE. The amount of the most abundant impurity may also be measured by SDS-PAGE with densitometry.

Further, an acceptable level of the most abundant impurity for the mixed collagenase I and collagenase II drug substance is less than about 5%, or 4%, or 3%, or 2%, or 1%, or 0.75%, or 0.5%, or 0.25%, or 0.1% (w/w) of the drug substance as measured by SDS-PAGE. The amount of the most abundant impurity may also be measured by SDS-PAGE with densitometry.

In addition, in certain embodiments, once the selected fractions are pooled into a collagenase I or collagenase II product, the overall purity of such pooled fractions is at least about 95%, or 96%, or 97%, or 98%, or 99%, or 100% as measured by RP-HPLC. In other embodiments, the overall purity for such pooled fractions are between about 80% and 100% as measured by RP-HPLC.

2. Elimination Strategy 2

According to this strategy, a fraction is rejected from further processing (forward processing) if it has detectable levels of neutral protease as measured by SDS-PAGE, SDS-PAGE with densitometry, casein Zymography, casein Zymography with densitometry, or a combination thereof. The concentration of protein in each fraction is determined by any method known to those skilled in the art. Each well of the gel can be loaded with any amount of protein. In some embodiments, the amount of protein loaded is between about 0.1 micrograms and about 100 micrograms, such as about 90, 80, 70, 60, 50, 40, 30, 25, 20, 19, 18, 17, 16, 15, 14, 13, 12, 11, 10, 9, 8, 7, 6, 5, 4, 3, 2, or 1 micrograms. Any fraction containing detectable levels of neutral protease on the gel is rejected from being pooled.

3. Elimination Strategy 3

According to this strategy, collagenase I fractions are pooled based on the position of the fraction relative to the elution peak and the estimated amount of collagenase II pooled. In other words, the elution peak of collagenase II is used as an identifier for which collagenase I fractions can be pooled.

The fractions of collagenase I pooled can be from any fraction(s) of the collagenase I elution peak. When multiple fractions are pooled, the fractions may be consecutive fractions or non-consecutive fractions. In some embodiments, fractions are pooled starting from the elution peak maximum of the collagenase I fractions and moving towards the tails evenly on both sides of the peak. In other embodiments, fractions are pooled starting from the first fraction that meets specified purity criteria for collagenase I purity or most abundant impurity, or both, and then moving towards the collagenase I elution peak maximum. In some embodiments, fractions are collected starting from any fraction not containing detectable levels of neutral protease (as measured by any technique known to those skilled in the art) and moving towards the beginning of the collagenase I elution peak.

The amount of collagenase I pooled may be different than the amount of collagenase II estimated (total collagenase II elution peak, pooled collagenase II amount, or otherwise). In some embodiments, the estimated amount of collagenase II may be about twice the amount of estimated collagenase I, or about one and a half times the amount of estimated collagenase I, or about three times the amount of estimated collagenase I. Any specific ratio will work, such as about 1:1.2 collagenase I to collagenase II, or about 1:1.1, or 1:1.3, or 1:1.4, or more of collagenase I to collagenase II.

For example, the strategy comprises: (a) calculating an approximate amount of collagenase II eluted contained in fractions passing the purity requirements stated above, and (b) discarding tail fractions from the collagenase I elution peak beyond the approximate amount of collagenase II that creates an approximate 1:1 mass ratio of collagenase I to the collagenase II amount calculated in (a), wherein the pooling of collagenase I fractions starts from about the first passing fraction of the collagenase I elution peak tails and moves towards the final collagenase I fraction. Collagenase compositions produced by this method are essentially free of neutral protease.

In another embodiment, the disclosure is directed to a process of manufacturing collagenase I and collagenase II derived from *C. histolyticum*, the process comprising the steps of (a) separating collagenase I from collagenase II using chromatography, (b) collecting elution fractions from step (a) for collagenase I and collagenase II separately, (c) discarding any fraction that has collagenase I or collagenase II less than about 91.8% the total amount of protein in the fraction as measured by SDS-PAGE with densitometry analysis, any single impurity being greater than about 5.8% of the total amount of protein in the fraction as measured by SDS-PAGE with densitometry analysis, and (d) calculating an approximate amount of collagenase II eluted contained in fractions passing the purity requirements of (c), and discarding tail fractions from the collagenase I elution peak beyond the approximate amount of collagenase II that creates an approximate 1:1 mass ratio of collagenase I to the collagenase II amount calculated in (d), wherein the discarding of tail collagenase I fractions starts from about the tails of the collagenase I elution peak and moves towards the peak maximum. Collagenase compositions produced by this method are essentially free of neutral protease.

Post-Removal of Neutral Protease, Finalization of Drug Product and Formulation

The collagenase I drug substance, after the neutral protease elimination step and before it is mixed with collagenase II, may have less than about 50 ng neutral protease per mg of collagenase I drug substance as measured by casein Zymography with or without densitometry. Alternatively, it may have less than about 40 ng, or 30 ng, or 20 ng, or 10 ng, or 5 ng, or 1 ng or less neutral protease per mg of collagenase I drug substance as measured by casein Zymography with or without densitometry.

In another aspect, the collagenase II drug substance, after the neutral protease elimination step and before it is mixed with collagenase I, may have less than about 50 ng neutral protease per mg of collagenase II drug substance as measured by casein Zymography with or without densitometry. Alternatively, it may have less than about 40 ng, or 30 ng, or 20 ng, or 10 ng, or 5 ng, or 1 ng or less neutral protease per mg of collagenase II drug substance as measured by casein Zymography with or without densitometry.

Further, the final, mixed collagenase I and collagenase II drug substance may have less than about 50 ng neutral protease per mg of collagenase I and II drug substance as measured by casein Zymography with or without densitometry. Alternatively, it may have less than about 40 ng, or 35 ng or 30 ng, or 25 ng, or 20 ng, or 15 ng, or 10 ng, or 5 ng, or 4 ng, or 3 ng, or 2 ng, or 1 ng or less neutral protease per mg of collagenase I and II drug substance as measured by casein Zymography with or without densitometry.

In other embodiments, the collagenase drug substance has less than about 1000 ng, or 750 ng, or 500 ng, or 250 ng, or 100 ng, or 75 ng, or 50 ng, or 40 ng, or 35 ng or 30 ng, or 25 ng, or 20 ng, or 15 ng, or 10 ng, or 5 ng, or 4 ng, or 3 ng, or 2 ng, or 1 ng or less neutral protease per mg of collagenase as measured by casein Zymography with or without densitometry.

In one example, the amount of neutral protease present is determined by comparing the measured amount of neutral protease in a well having about 5 micrograms to about 20 micrograms of collagenase. For instance, samples for a Zymography test method are prepared at 0.5 ug AUX-I per uL sample and loaded at 20 uL onto the SDS-PAGE gel. This yields a 10 ug AUX-I load on the gel. The Zymography test method has a limit of detection of 0.5 ng neutral protease. Therefore the limit of detection is 0.5 ng NP per 10 ug AUX-I.

$$\frac{0.5 \text{ ng } NP}{10 \text{ ug } AUX-I} \times \frac{1000 \text{ pg}}{1 \text{ ng}} =$$

$$\frac{500 \text{ pg}}{10 \text{ ug}} = \frac{50 \text{ pg}}{1 \text{ ug}} \times \frac{1000 \text{ ug}}{1 \text{ mg}} = \frac{5.0 \times 10^4 \text{ pg}}{1 \text{ mg}} \times \frac{1 \text{ ng}}{1000 \text{ pg}} = \frac{50 \text{ ng } NP}{1 \text{ mg } AUX-I}$$

In another embodiment, the disclosure is directed to a collagenase composition derived from *C. histolyticum*, wherein the collagenase composition comprises a collagenase I product and a collagenase II product, wherein the collagenase product is at least 95% pure by area as measured by reverse phase high pressure liquid chromatography (RP-HPLC), and wherein the collagenase I product is essentially free of neutral protease.

In some embodiments, the collagenase composition or pharmaceutical formulation has a mass ratio of approximately 1 to 1 of collagenase Ito collagenase II. However, other mass ratios of collagenase Ito collagenase II are contemplated. The mass ratios may range anywhere from about 1:10 to about 10:1 of collagenase Ito collagenase II. Preferably, the mass ratio is between about 1:3 to about 3:1 of collagenase Ito collagenase II. More preferably, the mass ratio is between about 0.9:1 to about 1:1.4 of collagenase Ito collagenase II. For example, the mass ratio may be about 1:1, or 1:1.5, or 1.5:1, or 2.4:1, 1:2.1, or 1:1.3, or 1:1.4 or 1.4:1 or 1.3:1 of collagenase Ito collagenase II. In one aspect, the mass ratio of collagenase Ito collagenase II is about 1:1. In one embodiment, the collagenase concentrate has an extinction coefficient of 1.528.

Further, the present invention provides a collagenase composition comprising collagenase I and collagenase II derived from *C. histolyticum*, wherein the collagenase I and collagenase II have a mass ratio between about 0.9:1 to about 1:1.4 collagenase Ito collagenase II (e.g., about 1:1), and wherein the collagenase composition has a purity of at least 90% by area as measured by RP-HPLC, or a purity of at least about 95% by area as measured by RP-HPLC, or at least 97% by area as measured by RP-HPLC, or a purity of at least 98% by area as measured by RP-HPLC, or a purity of at least 99% by area as measured by RP-HPLC.

The pharmaceutical formulations of the present invention comprise a therapeutically effective amount of a collagenase composition of the present invention formulated together with one or more pharmaceutically acceptable carriers or excipients.

In another embodiment, the concentrations of zinc and/or nickel are controlled during the manufacturing process of collagenase, collagenase I, collagenase II, or both collagenase I and collagenase II, and formation of the drug product resulting in process repeatability of about 88%, 89%, 90%, 91%, 92%, 93%, 94%, 95%, 96%, 97%, 98%, 99%, or 100% for a collagenase product, or collagenase I product or collagenase II product purity of at least about 95%, at least about 96%, at least about 97%, at least about 98%, at least about 99%, or 100% by area, as measured by RP-HPLC (reverse phase high pressure liquid chromatography).

In one embodiment, the disclosure is directed to a method for isolation and purification of collagenase I and collagenase II derived from *C. histolyticum*, wherein nickel level and zinc level are controlled during the collagenase purification process resulting in an improved process repeatability of greater than about 95% pure collagenase I or collagenase II.

In one example, the purification process includes harvesting collagenase from fermented *C. histolyticum* (such as from porcine-derived media (preferably, proteose peptone)) media through a filter (for example, a Millipore Millistak HC POD), followed by adjusting the Mustang Q filtrate to 1 M using ammonium sulfate concentration (for example, at an ammonium sulfate at 60% saturation) to promote binding of collagenases to HIC column, then resuspending or dissolving precipitated collagenase in ammonium sulfate, followed by anion ion-exchange chromatography (for example, using a Mustang Q column), followed by filtration (for example, a 0.45 □ filter), followed by buffer-exchange (for example, dialysis or tangential flow filtration) then running the filtrate over a hydrophobic interaction chromatography column (for example, Q-sepharose), followed by addition of leupeptin, followed by buffer exchange.

In another example, the purification process includes harvesting collagenase from fermented *C. histolyticum* (for example, fermented in a vegetable-derived media) through a depth filter (for example, a Millipore Millistak HC POD), followed by anion exchange chromatography (such as Mustang Q filtration), followed by addition of salt (preferably ammonium sulfate) to a concentration of about 0.8 M to about 1.2 M (for example, to about 1 M ammonium sulfate), followed by a hydrophobic interaction chromatography column (for example, phenyl sepharose), followed by buffer exchange (for example, using TFF and removing ammonium sulfate), followed by anion exchange chromatography (for example, using a Q-sepharose column), followed by collecting fractions of the filtrate from the anion exchange chromatography for AUX-I and AUX-II separately, then pooling fractions of AUX-I together and pooling fractions of AUX-II together. Leupeptin may be added to the purification process at the hydrophobic interaction chromatography step, the first buffer exchange step, and the second anion exchange chromatography steps.

One example of a purification process according to the invention includes harvesting collagenase from fermented *C. histolyticum* through a filter (for example, a Millipore Millistak HC POD), followed by filtration through at least one 0.2 micron filter, followed by anion exchange chromatography (such as Mustang Q filtration), wherein the effluent is adjusted to have between about 0.8 M to about 1.2 M ammonium sulfate concentration, followed by an hydrophobic interaction (HIC) column (for example, phenyl sepharose), followed by buffer exchange (for example, using TFF and removing the ammonium sulfate), followed by anion exchange chromatography (for example, Q-sepharose), followed by collecting fractions of the eluate from the anion exchange chromatography for AUX-I and AUX-II separately, then pooling fractions of AUX-I together and pooling fractions of AUX-II together, followed by buffer exchange into pharmaceutical formulation buffers (for example, into 10 mM Tris, 60 mM sucrose at pH 8 using tangential flow filtration). Leupeptin is optionally added to the purification process at the hydrophobic interaction chromatography step, the first buffer exchange step, and the second anion exchange chromatography step.

In certain embodiments of the present invention, the collagenase purification procedure comprises the steps of: a) filtering the crude harvest using ion exchange chromatography; preferably with an anion-exchange capsule filter (such as MUSTANG Q); b) adding ammonium sulfate; preferably to a final concentration of about 1M; c) filtering the crude harvest; preferably through a 0.45 μm filter; d) subjecting the filtrate through hydrophobic interaction chromatography (HIC); preferably a phenyl sepharose 6FF (low sub) column; e) adding leupeptin to the eluate; preferably to a final concentration of about 0.2 mM to post HIC eluted product; f) removing the ammonium sulfate and maintaining the leupeptin; preferably using buffer exchange by tangential flow filtration (TFF); g) filtering the mixture of step (f); preferably through a 0.45 μm filter; h) separating collagenase I and collagenase II using ion exchange chromatography; preferably using a Q-Sepharose High Performance (Q HP) column; and i) performing a neutral protease elimination step. Optionally, additional steps may be performed including j) performing buffer exchange of collagenase I and II separately after step (i); preferably by preparing TFF concentration and formulation for collagenase I and collagenase II separately, wherein TFF is a tangential flow filter with 10 and/or 30 K MWCO (molecular weight cut-off) PES or RC-polyethersulfone or regenerated cellulose filter membranes (TFF provides a means to retain and concentrate select protein and exchange the protein from one buffer solution into another); and k) filtering separately the buffer exchanged collagenase I and II, preferably through 0.2 μm filtration systems.

One embodiment of the invention includes a method for manufacturing collagenase, collagenase I, collagenase II, or both collagenase I and collagenase II, wherein the concentrations of zinc and/or nickel are controlled for in the process such that the concentration of nickel during the manufacturing process is less than about 0.2 ppm and/or the concentration of zinc during the manufacturing process is less than about 1 ppm and these metal concentrations result in greater than about 90% process repeatability and achieving purity of greater than about 95% by area as measured by RP-HPLC for collagenase, collagenase I, collagenase II, or both collagenase I and collagenase II. Another embodiment of the invention includes the monitoring of zinc and nickel levels in the collagenase, collagenase I, collagenase II, or collagenase I and collagenase II manufacturing process, wherein the concentration of nickel during the manufacturing process is maintained at less than about 0.2 ppm and/or the concentration of zinc during the manufacturing process is maintained less than about 1 ppm such that these concentrations of metals result in greater than about 95% process repeatability of greater than about 95% pure collagenase composition.

The disclosure further includes a method for manufacturing collagenase, collagenase I, collagenase II, or both collagenase I and collagenase II, wherein the concentrations of zinc and/or nickel are monitored and/or controlled for in the process such that the concentration of nickel during the manufacturing process is less than about 0.2 ppm and/or the concentration of zinc during the manufacturing process is less than about 1 ppm and these metal concentrations result in greater than about 90% process repeatability achieving greater than about 95% pure collagenase, collagenase I, or collagenase II, or both collagenase I and collagenase II. Another embodiment of the invention includes the monitoring of zinc and nickel levels in the collagenase, collagenase I, collagenase II, or both collagenase I and collagenase II manufacturing process, wherein the concentration of nickel during the manufacturing process is maintained at less than about 0.2 ppm and/or the concentration of zinc during the manufacturing process is maintained less than about 1 ppm such that these concentrations of metals result in greater than about 95% process repeatability and a purity of greater than about 95% by area as measured by RP-HPLC for collagenase, collagenase I, collagenase II, or both collagenase I and collagenase II.

A further embodiment of the invention includes a method for manufacturing collagenase, collagenase I, collagenase II, or both collagenase I and collagenase II wherein the concentrations of zinc and/or nickel are monitored and/or controlled for in the process such that the concentration of nickel during the manufacturing process is less than about 0.5 ppm and/or the concentration of zinc during the manufacturing process is less than about 10 ppm and these metal concentrations result in greater than about 90% process repeatability achieving purity greater than about 95% by area as measured by RP-HPLC for collagenase, collagenase I, collagenase II, or both collagenase I and collagenase II. Yet another embodiment of the invention includes a method for manufacturing collagenase, collagenase I, collagenase II, or both collagenase I and collagenase II wherein the concentrations of zinc and/or nickel are monitored and/or controlled for in the process such that the concentration of nickel during the manufacturing process is less than about 0.5 ppm and/or the concentration of zinc during the manufacturing process is less than about 10 ppm and these metal concentrations result in a greater than about 95% process repeatability achieving a purity greater than about 95% by area as measured by RP-HPLC for collagenase, collagenase I, collagenase II, or both collagenase I and collagenase II.

A further embodiment of the invention includes a method for manufacturing collagenase, collagenase I, collagenase II, or both collagenase I and collagenase II, wherein the concentrations of zinc and/or nickel are controlled for in the process such that the concentration of nickel during the manufacturing process is less than about 0.5 ppm and/or the concentration of zinc during the manufacturing process is less than about 10 ppm and these metal concentrations result in greater than about 95% process repeatability achieving a purity of greater than about 95% by area as measured by RP-HPLC collagenase composition.

Yet another embodiment of the invention includes a method for manufacturing collagenase, collagenase I, collagenase II, or both collagenase I and collagenase II wherein the concentrations of zinc and/or nickel are controlled for in the process such that the concentration of nickel during the manufacturing process is less than about 0.5 ppm and/or the concentration of zinc during the manufacturing process is less than about 10 ppm and these metal concentrations result in greater than about 95% process repeatability achieving a purity of greater than about 95% by area as measured by RP-HPLC for collagenase, collagenase I, collagenase II, or both collagenase I and collagenase II.

There is further disclosed a method for manufacturing collagenase, collagenase I, collagenase II, or both collagenase I and collagenase II wherein the concentrations of zinc and/or nickel are controlled for in the process such that the concentration of nickel during the manufacturing process is less than about 0.5 ppm and/or the concentration of zinc during the manufacturing process is less than about 10 ppm and these metal concentrations result in greater than about 90% process repeatability achieving a purity greater than about 97% by area as measured by RP-HPLC for collagenase, collagenase I, collagenase II, or both collagenase I and collagenase II.

The disclosure further contemplates a method for manufacturing collagenase, collagenase I, collagenase II, or both collagenase I and collagenase II wherein the concentrations of zinc and/or nickel are controlled for in the process such that the concentration of nickel during the manufacturing process is less than about 0.5 ppm and/or the concentration of zinc during the manufacturing process is less than about 10 ppm and these metal concentrations result in greater than about 95% process repeatability achieving a purity of greater than about 97% by area as measured by RP-HPLC for collagenase, collagenase I, collagenase II, or both collagenase I and collagenase II.

In another embodiment, the disclosure is directed to a process of manufacturing collagenase I and collagenase II derived from *C. histolyticum*, the process comprising the steps of (a) separating collagenase I from collagenase II using chromatography, (b) collecting elution fractions from step (a) for collagenase I and collagenase II separately, (c) assaying each fraction for neutral protease using SDS-PAGE, SDS-PAGE and densitometry, or Zymography, (d) discarding any fraction that has collagenase I or collagenase II less than about 91.8% the total amount of protein in the fraction as measured by SDS-PAGE with densitometry analysis, any single impurity being greater than about 5.8% of the total amount of protein in the fraction as measured by SDS-PAGE with densitometry analysis, or that as shows a detectable level of neutral protease as tested in (c), and (e) pooling only passing fractions of collagenase I for collagenase I product and pooling only passing fractions of collagenase II for collagenase II product, and wherein the pooled collagenase I product or collagenase II product is pure to at least 95% by area as measured by RP-HPLC. Collagenase compositions produced by this method are essentially free of neutral protease.

In another embodiment, the disclosure is directed to a process of manufacturing collagenase I and collagenase II derived from *C. histolyticum*, the process comprising the steps of (a) separating collagenase I from collagenase II using chromatography, (b) collecting elution fractions from step (a) for collagenase I and collagenase II separately, (c) discarding any fraction that has collagenase I or collagenase II less than about 91.8% the total amount of protein in the fraction as measured by SDS-PAGE with densitometry analysis, any single impurity being greater than about 5.8% of the total amount of protein in the fraction as measured by SDS-PAGE with densitometry analysis, and (d) calculating an approximate amount of collagenase II eluted contained in fractions passing the purity requirements of (c), and discarding tail fractions from the collagenase I elution peak beyond the approximate amount of collagenase I that creates an approximate 1:1 mass ratio of collagenase I to the collagenase II amount calculated in (d), wherein the pooling of collagenase I fractions starts from about the first passing fraction of the collagenase I elution peak tails and moves towards the final collagenase I fraction. Collagenase compositions produced by this method are essentially free of neutral protease.

The disclosure is directed to a process of manufacturing collagenase I and collagenase II derived from *C. histolyticum*, the process comprising the steps of (a) separating collagenase I from collagenase II using chromatography, (b) collecting elution fractions from step (a) for collagenase I and collagenase II separately, (c) discarding any fraction that has collagenase I or collagenase II less than about 91.8% the total amount of protein in the fraction as measured by SDS-PAGE with densitometry analysis, any single impurity being greater than about 5.8% of the total amount of protein in the fraction as measured by SDS-PAGE with densitometry analysis, and (d) calculating an approximate amount of collagenase II eluted contained in fractions passing the purity requirements of (c), and discarding tail fractions from the collagenase I elution peak beyond the approximate amount of collagenase I that creates an approximate 1:1 mass ratio of collagenase I to the collagenase II amount calculated in (d), wherein the discarding of tail collagenase I fractions starts from about the tails of the collagenase I elution peak and moves towards the peak maximum. Collagenase compositions produced by this method are essentially free of neutral protease.

The disclosure is directed to process of manufacturing collagenase I and collagenase II derived from *C. histolyticum*, wherein (a) neutral protease is essentially eliminated from the collagenase I product during the manufacturing process, and (b) the concentration of nickel, zinc, aluminum, arsenic, calcium, cadmium, chromium, copper, iron, magnesium, lead, or a combination thereof is controlled during the manufacturing process.

In another embodiment, the disclosure is directed to a method for purifying collagenase I and collagenase II, comprising: (a) filtering a fermentation liquid from *C. histolyticum* through an anion exchange filter; (b) adding ammonium sulfate to the filtrate of step (a); (c) subjecting the filtrate of step (b) to a hydrophobic interaction chromatography column; (d) adding leupeptin to the eluate of step (c); (e) removing the ammonium sulfate from the mixture of step (d); (f) filtering the mixture of step (e); and (g) separating the collagenase I and II in the mixture of step (f) using ion-exchange chromatography, and wherein the concentration of nickel, zinc, aluminum, arsenic, calcium, cadmium, chromium, copper, iron, magnesium, lead, or a combination thereof is controlled during the purification processes.

In a further embodiment, the disclosure is directed to a method for purifying collagenase I and collagenase II, comprising: (a) filtering a fermentation liquid from *C. histolyticum* through an anion exchange filter; (b) adding ammonium sulfate to the filtrate of step (a); (c) subjecting the filtrate of step (b) to a hydrophobic interaction chromatography column; (d) adding leupeptin to the eluate of step (c); (e) removing the ammonium sulfate from the mixture of step (d); (f) filtering the mixture of step (e); and (g) separating the collagenase I and II in the mixture of step (f) using ion-exchange chromatography, wherein nickel level or zinc level is controlled during the purification process.

The disclosure is also directed to a method for purifying collagenase I and collagenase II, comprising: (a) filtering a fermentation liquid from *C. histolyticum* through an anion exchange filter; (b) adding ammonium sulfate to the filtrate step of step (a); (c) subjecting the filtrate of step (b) to a hydrophobic interaction chromatography column; (d) adding leupeptin to the eluate of step (c); (e) removing the ammonium sulfate from the mixture of step (d); (f) filtering the mixture of step (e); and (g) separating the collagenase I and II in the mixture of step (f) using ion-exchange chromatography, and (h) removing neutral protease from collagenase I or collagenase II from the elutions of step (g).

In addition, the disclosure is directed to a method for purifying collagenase I and collagenase II, comprising: (a) filtering a fermentation liquid from *C. histolyticum* through an anion exchange filter; (b) adding ammonium sulfate to the filtrate of step (a); (c) subjecting the filtrate of step (b) to a hydrophobic interaction chromatography column; (d) adding leupeptin to the eluate of step (c); (e) removing the ammonium sulfate from the mixture of step (d); (f) filtering the mixture of step (e); and (g) separating the collagenase I and II in the mixture of step (f) using ion-exchange chromatography, wherein nickel level and zinc level are controlled during the collagenase purification process.

In another embodiment, the disclosure is directed to a process for producing a drug product consisting of isolated and purified collagenase I and collagenase II derived from *C. histolyticum*, wherein the collagenase I and collagenase II have a mass ratio of about 1 to 1 and the drug product is at least 95% by area pure as determined by reverse phase high performance liquid chromatography, comprising the steps of: (a) fermenting *C. histolyticum*; (b) harvesting a crude fermentation comprising collagenase I and collagenase II; (c) purifying collagenase I and collagenase II from the crude harvest via filtration and column chromatography comprising the steps of: (i) filtering a fermentation liquid from *C. histolyticum* through an anion exchange filter; (ii) adding ammonium sulfate to the filtrate of step (i); (iii) subjecting the filtrate of step (ii) to a hydrophobic interaction chromatography column; (iv) adding leupeptin to the eluate of step (iii); (v) removing the ammonium sulfate from the mixture of step (iv); (vi) filtering the mixture of step (v); and (vii) separating the collagenase I and II in the mixture of step (vi) using ion-exchange chromatography; and (d) combining the collagenase I and collagenase II purified from step (c) at a ratio of about 1 to 1, wherein the concentration of nickel, zinc, aluminum, arsenic, calcium, cadmium, chromium, copper, iron, magnesium, lead, or a combination thereof is controlled during the manufacturing process.

Further, the disclosure is directed to a process for producing a drug product consisting of isolated and purified collagenase I and collagenase II derived from *C. histolyticum*, wherein the collagenase I and collagenase II have a mass ratio of about 1 to 1 and the drug product is at least 95% by area pure as determined by reverse phase high performance liquid chromatography, comprising the steps of: (a) fermenting *C. histolyticum*; (b) harvesting a crude fermentation comprising collagenase I and collagenase II; (c) purifying collagenase I and collagenase II from the crude harvest via filtration and column chromatography comprising the steps of: (i) filtering a fermentation liquid from *C. histolyticum* through an anion exchange filter; (ii) adding ammonium sulfate to the filtrate of step (i); (iii) subjecting the filtrate of step (ii) to a hydrophobic interaction chromatography column; (iv) adding leupeptin to the eluate of step (iii); (v) removing the ammonium sulfate from the mixture of step (iv); (vi) filtering the mixture of step (v); and (vii) separating the collagenase I and II in the mixture of step (vi) using ion-exchange chromatography; and (d) combining the collagenase I and collagenase II purified from step (c) at a ratio of about 1 to 1, wherein nickel level or zinc level, or zinc and nickel levels are controlled during the manufacturing process.

The disclosure is directed to a process for producing a drug product consisting of isolated and purified collagenase I and collagenase II derived from *C. histolyticum*, wherein the collagenase I and collagenase II have a mass ratio of about 1 to 1 and the drug product is at least 95% by area pure as determined by reverse phase high performance liquid chromatography, comprising the steps of: (a) fermenting *C. histolyticum*; (b) harvesting a crude fermentation comprising collagenase I and collagenase II; (c) purifying collagenase I and collagenase II from the crude harvest via filtration and column chromatography comprising the steps of: (i) filtering a fermentation liquid from *C. histolyticum* through an anion exchange filter; (ii) adding ammonium sulfate to the filtrate of step (i); (iii) subjecting the filtrate of step (ii) to a hydrophobic interaction chromatography column; (iv) adding leupeptin to the eluate of step (iii); (v) removing the ammonium sulfate from the mixture of step (iv); (vi) filtering the mixture of step (v); and (vii) separating the collagenase I and II in the mixture of step (vi) using ion-exchange chromatography; wherein the separating step further comprises (a) collecting elution fractions from (vii) for collagenase I and collagenase II separately, (b) assaying each fraction for neutral protease using SDS-PAGE or Zymography, (c) discarding any fraction that has collagenase I or collagenase II less than about 91.8% the total amount of protein in the fraction as measured by SDS-PAGE with densitometry analysis, any single impurity being greater than about 5.8% of the total amount of protein in the fraction as measured by SDS-PAGE with densitometry analysis, or that as shows a detectable level of neutral protease as tested in (b); and (d) pooling only passing fractions of collagenase I for collagenase I product and pooling only passing fractions of collagenase II for collagenase II product. Collagenase compositions produced by this method are essentially free of neutral protease.

EXAMPLES

The following examples are included to demonstrate certain embodiments of the present disclosure. Those of skill in the art should, however, in light of the present disclosure, appreciate that modifications can be made in the specific embodiments that are disclosed and still obtain a like or similar result without departing from the spirit and scope of the invention. Therefore all matter set forth is to be interpreted as illustrative and not in a limiting sense.

Example 1—Categorical Classification and Trending of IEX Fraction Impurities when Analyzed by the Optimized SDS-PAGE Method IEX fractions were tested from 13 different lots of manufactured collagenase I and collagenase II obtained from *C. histolyticum* as shown in Table 1. Each collagenase fraction collected from the IEX elute in each of the lots was run on an SDS-PAGE gel and analyzed using gel densitometry with a Bio-Rad densitometer and accompanying densitometry analysis software. For each fraction of each lot, the percent purity of undegraded collagenase I or II and the percent of each visible impurity (collagenase fragment or otherwise) was determined.

TABLE 1

| Lots Used to Determine Fraction Impurity Classifications for the Optimized SDS-PAGE Method | | |
|---|---|---|
| Manufacturing Site | Year of Manufacture | Lot Number |
| Site A | 2013 | L-PV 1 |
| | | L-PV 2 |
| | | L-PV 3 |

TABLE 1-continued

| Lots Used to Determine Fraction Impurity Classifications for the Optimized SDS-PAGE Method | | |
|---|---|---|
| Manufacturing Site | Year of Manufacture | Lot Number |
| Site B | 2013 | CD50-1000357 |
| | | CD50-1000375 |
| | | CD50-1000413 |
| | | CD50-1000415 |
| | 2014 | CD50-1000416 |
| | | CD50-1000516 |
| | | CD50-1000517 |
| | | CD50-1000518 |
| | | CD50-1000519 |
| | | CD50-1000520 |

Impurities are stratified into four primary categories (90 kD, 80 kD, 55 kD, and 40 kD) using the molecular weight value reported by the software and comparison of the vertical position of the impurity to the vertical position of the known molecular weight bands located in the molecular weight marker lane. Impurities that do not fit in a category were classified as "Other." The SDS-PAGE method utilizing gel densitometry is capable of resolving more impurity bands than with just the current SDS-PAGE method alone.

A. Quantitation of Major and Minor Bands in Collagenase *C. histolyticum* Ion-Exchange Chromatography Fractions by Sodium Dodecyl Sulfate—Polyacrylamide Gel Electrophoresis and Densitometry This method determines the purity and impurity of Collagenase *C. histolyticum* Ion-Exchange Chromatography Fractions using Sodium Dodecyl Sulfate—Polyacrylamide Gel Electrophoresis (SDS-PAGE) with 4-12% NuPAGE gels (MES buffer) and Colloidal Coomassie staining. This method uses a densitometric analysis of the gel to allow for relative quantitation of the major bands (percent AUX-I, AUX-II, or both) and minor bands of product-fragments or other impurities (percent minor bands).

Figure 1:
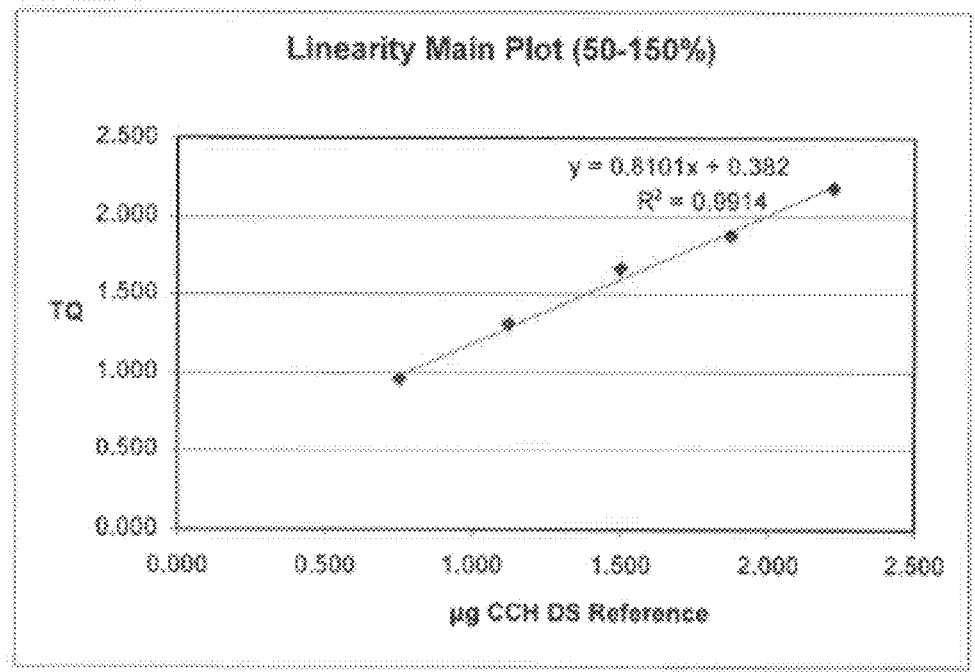
FIG. 1 is an example of a plot that shows the linearity of the response for the AUX-FAUX-II band. It is a plot of trace quantities of collagenase versus micrograms of a known reference standard over a minimum range of 1.125 micrograms to 1.875 micrograms and has an $R^2$ value greater than 98%.

Generally, the amount of collagenase loaded into a well of a gel for SDS-PAGE is linear to the intensity of the band seen with the densitometry software. For example, linearity of the response for the collagenase band can be demonstrated in a plot of collagenase vs. µg of a known reference standard over the of 1.123-1.875 µg (75%-125% of target) collagenase with an $R^2$ value>0.98. An example of a typical linearity plot is shown in FIG. 1.

A reference standard for the samples being analyzed should be used. For example, an AUX-I Intermediate Reference Standard can be used for analyzing elute fractions of AUX-I from the IEX step. The amount of reference standard and samples required to generate the final sample for gels (C2=0.15 mg protein/mL) are calculated the following formula: $C_1V_1=C_2V_2$ $C_1$=The initial concentration of the sample to be tested in mg/mL $V_1$=The volume required in µL of sample at the initial concentration $C_2$=1 mg/mL (The concentration of the final sample preparation)

$V_2$=The volume in µL of the final sample preparation

B. Impurity Categorical Classification i. Approach to Impurity Classification

Fraction impurities can be determined based on an analysis of the gel produced from analyzing samples of the fractions using SDS-PAGE with densitometry. Each gel is placed on a densitometer and the gel image is scanned using the densitometer (e.g., Bio-Rad densitometer) into densitometer software (e.g., Bio-Rad Quantity One software). An analyst ensures that the software has correctly identified the gel lanes and appropriate bands. The software generates an annotated image report, such as the representative images presented in FIG. 2.

Figure 2:
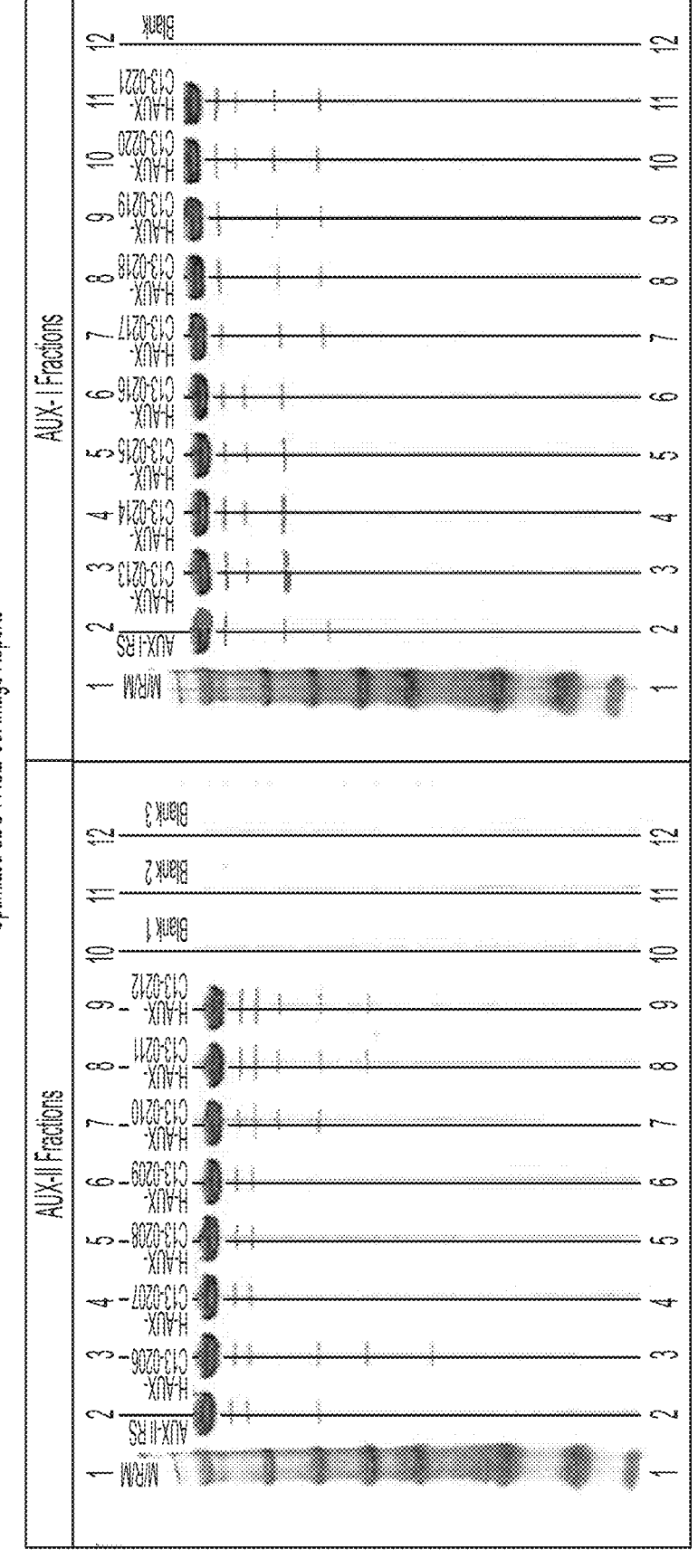
FIG. 2 is an example of the annotated image report generated by Bio-Rad Quantity One software. Lane 1 contains a molecular weight standard with bands of a known molecular weight. Lane 2 contains the appropriate AUX Intermediate reference standard. The remaining lanes contain a sample from each IEX fraction. The main product band is the top band of each lane and each additional lower band represents an impurity.
Figure 3:
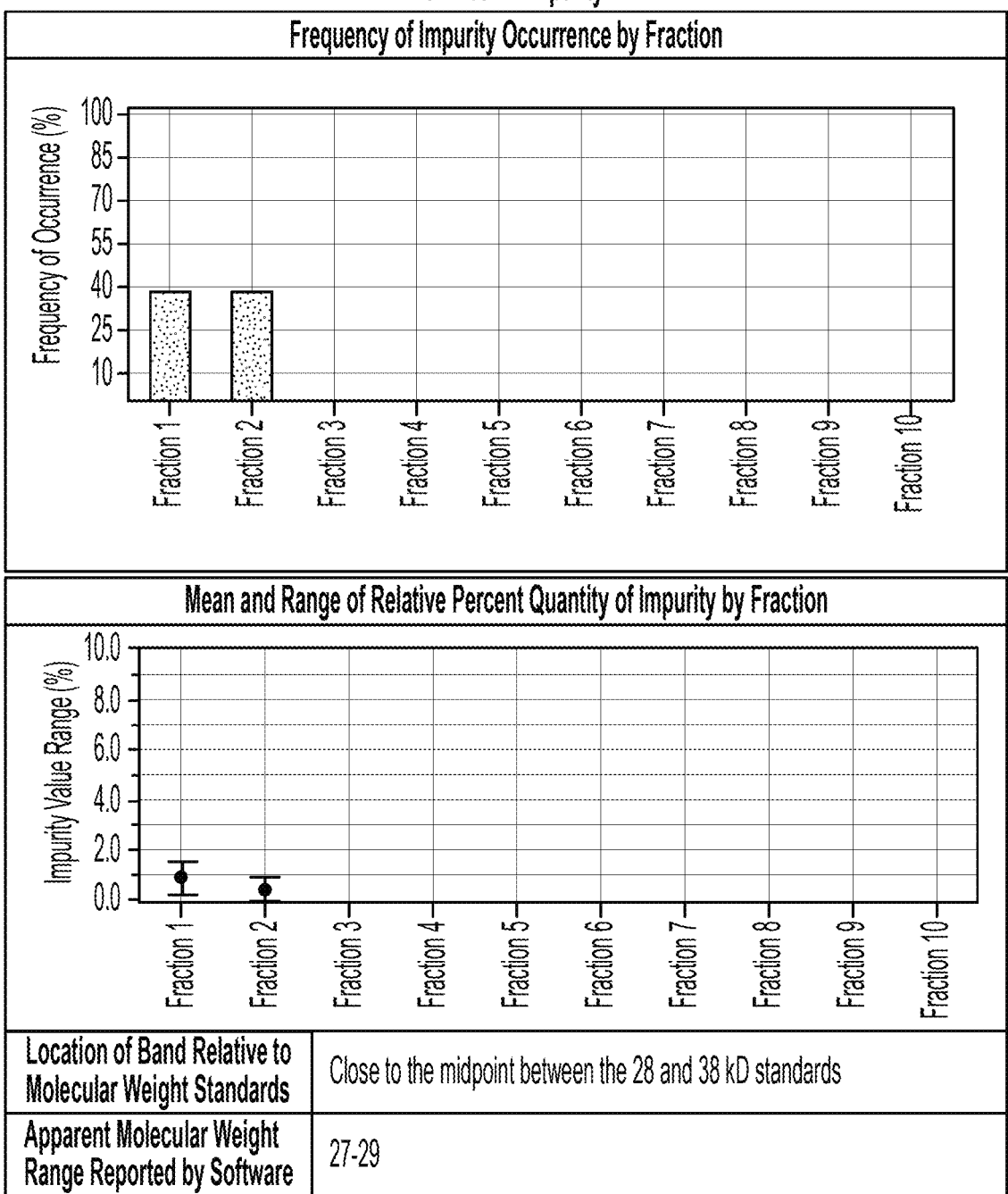
FIG. 3 shows the frequency of impurity occurrence by fraction and the mean and range of relative percent quantity of impurity by fraction for the AUX-I 33 kD impurity.
Figure 4:
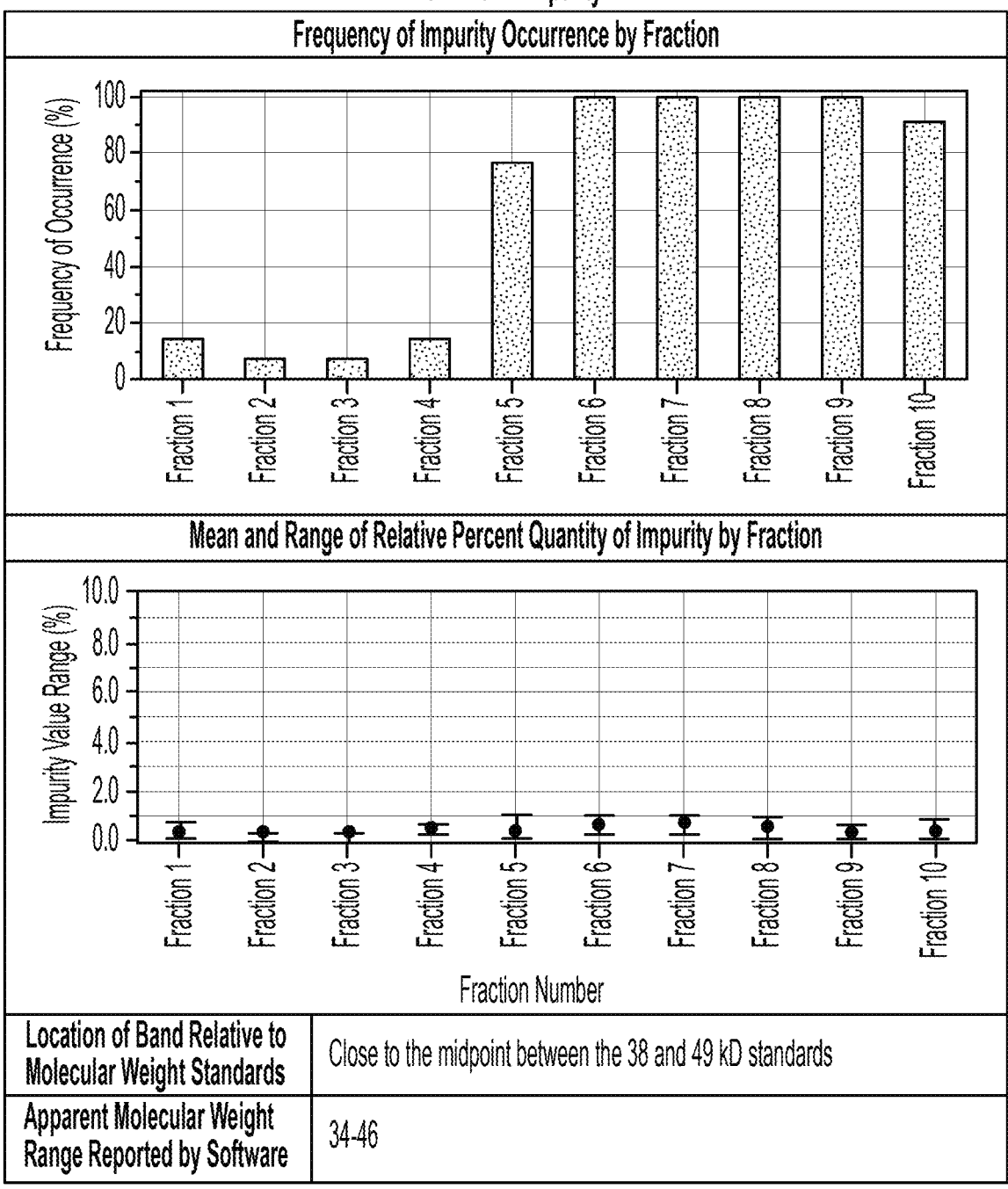
FIG. 4 shows the frequency of impurity occurrence by fraction and the mean and range of relative percent quantity of impurity by fraction for the AUX-I 45 kD impurity.
Figure 5:
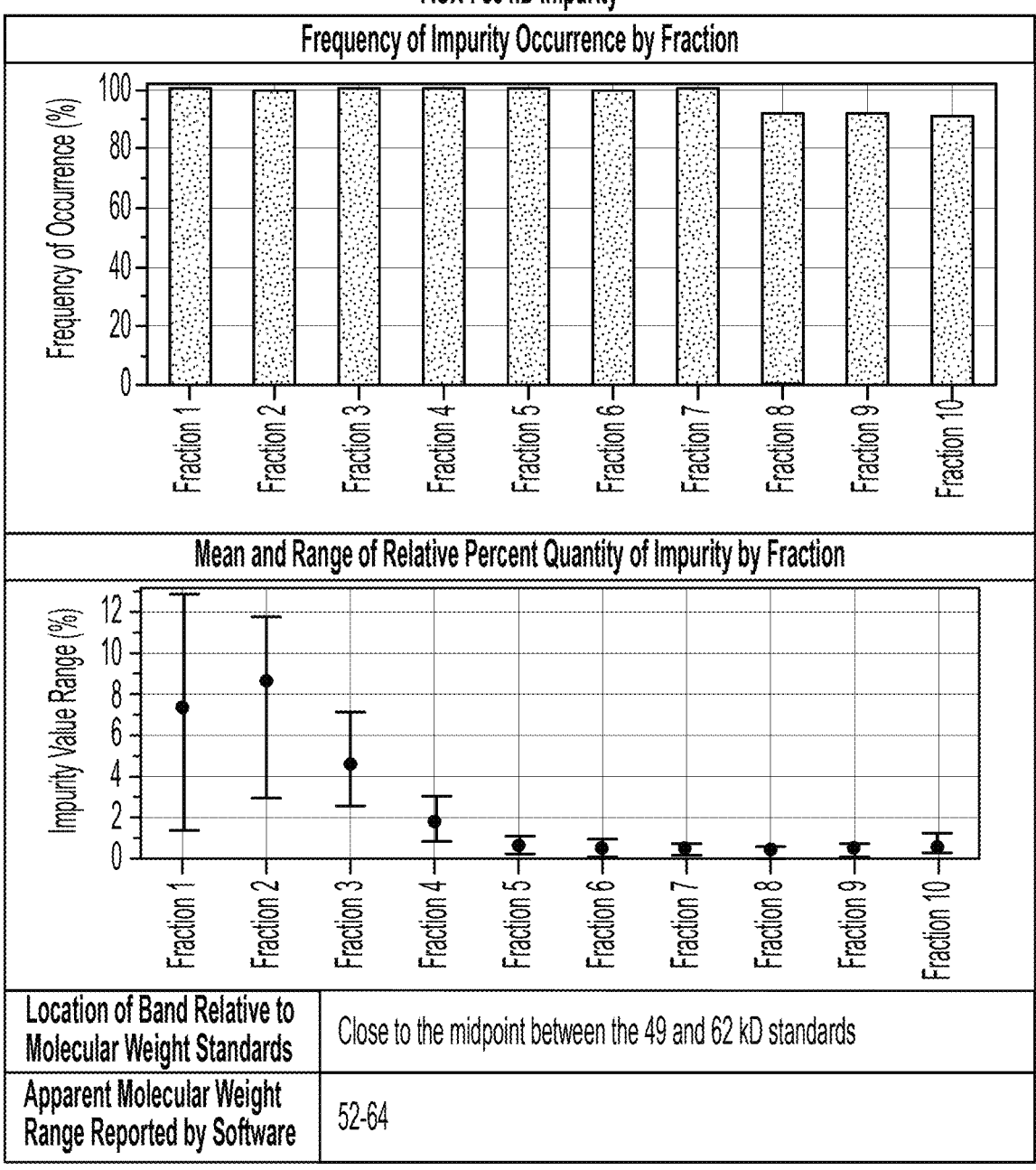
FIG. 5 shows the frequency of impurity occurrence by fraction and the mean and range of relative percent quantity of impurity by fraction for the AUX-I 55 kD impurity.
Figure 6:
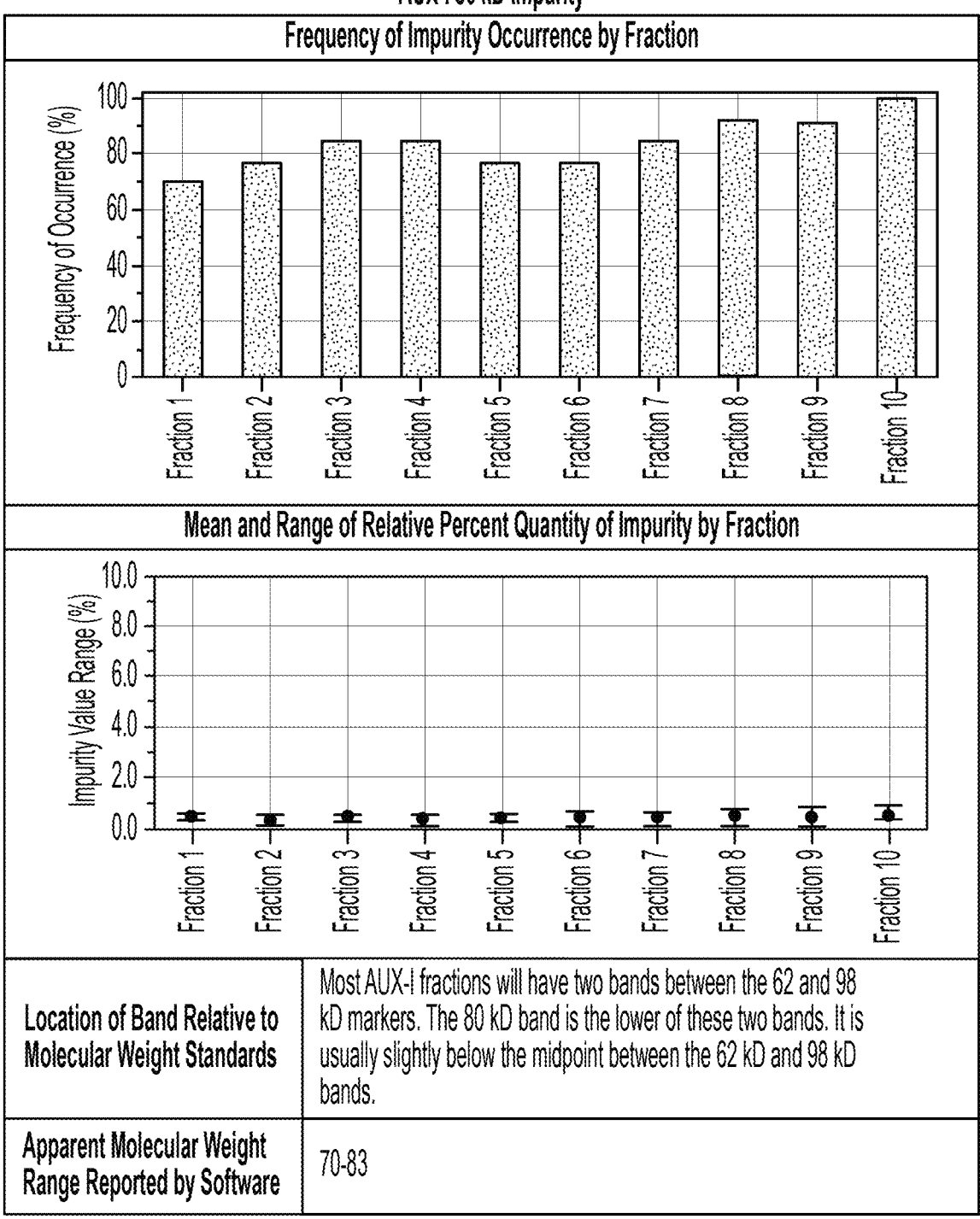
FIG. 6 shows the frequency of impurity occurrence by fraction and the mean and range of relative percent quantity of impurity by fraction for the AUX-I 80 kD impurity.
Figure 7:
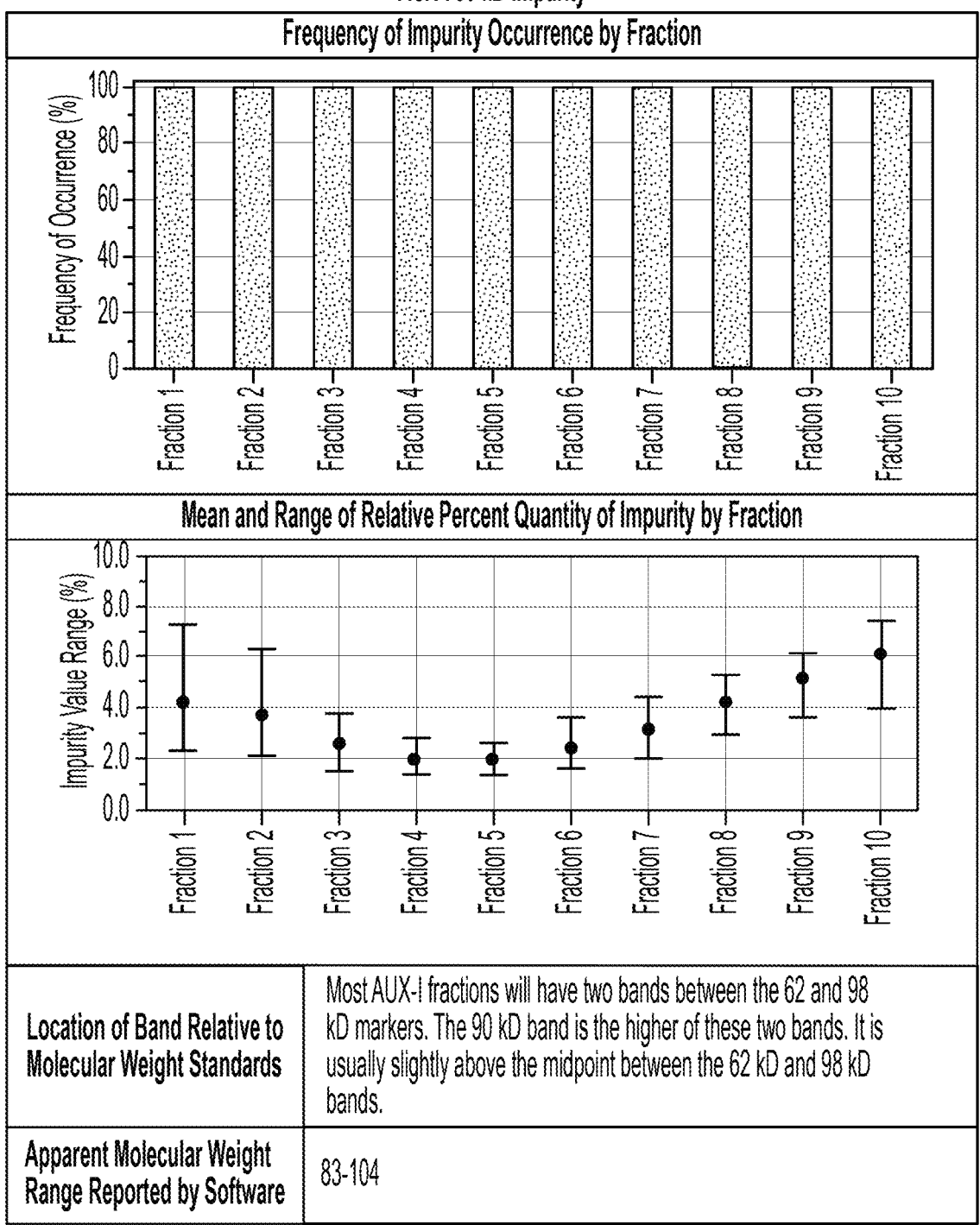
FIG. 7 shows the frequency of impurity occurrence by fraction and the mean and range of relative percent quantity of impurity by fraction for the AUX-I 90 kD impurity.
Figure 8:
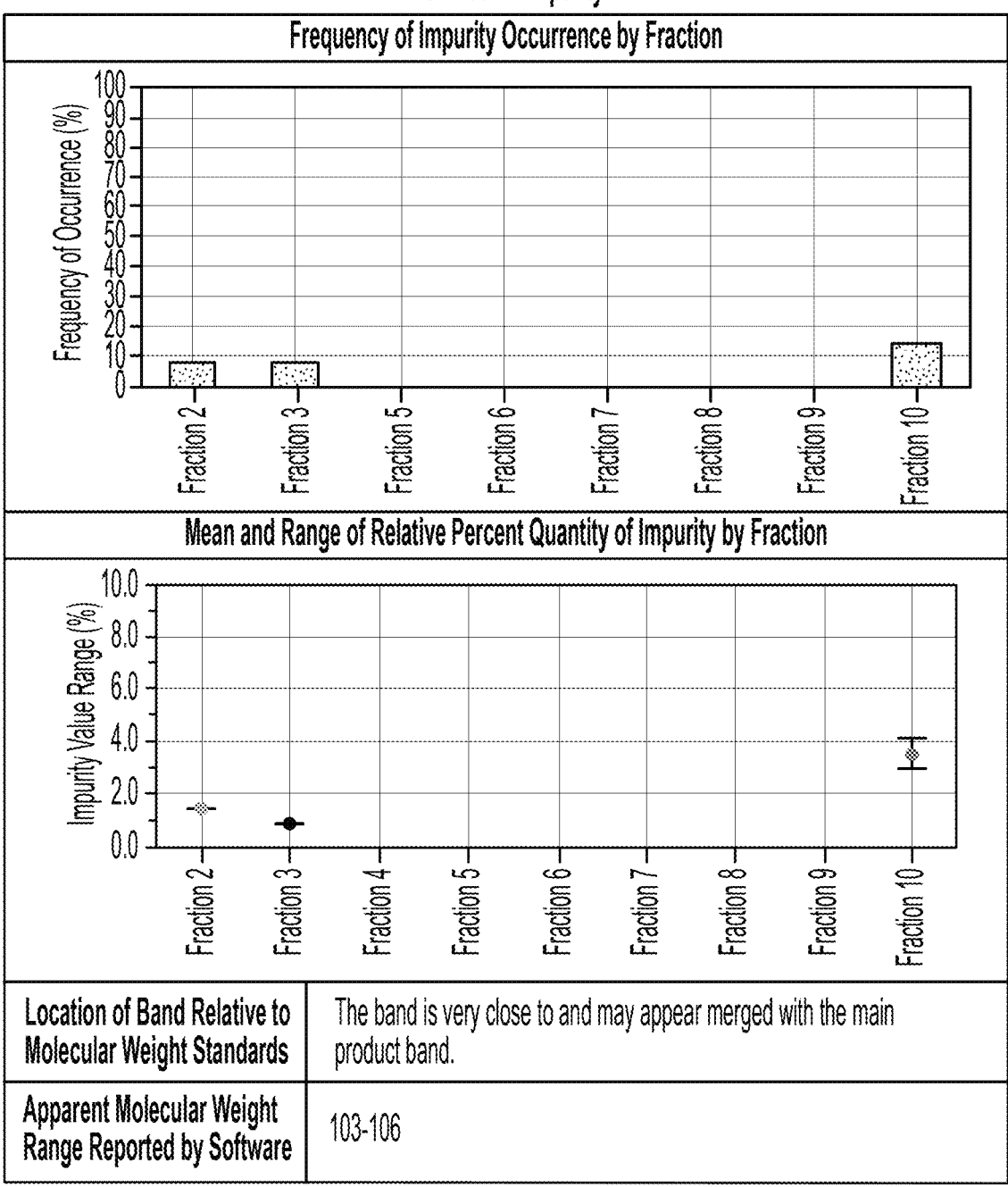
FIG. 8 shows the frequency of impurity occurrence by fraction and the mean and range of relative percent quantity of impurity by fraction for the AUX-I 96 kD impurity.
Figure 9:
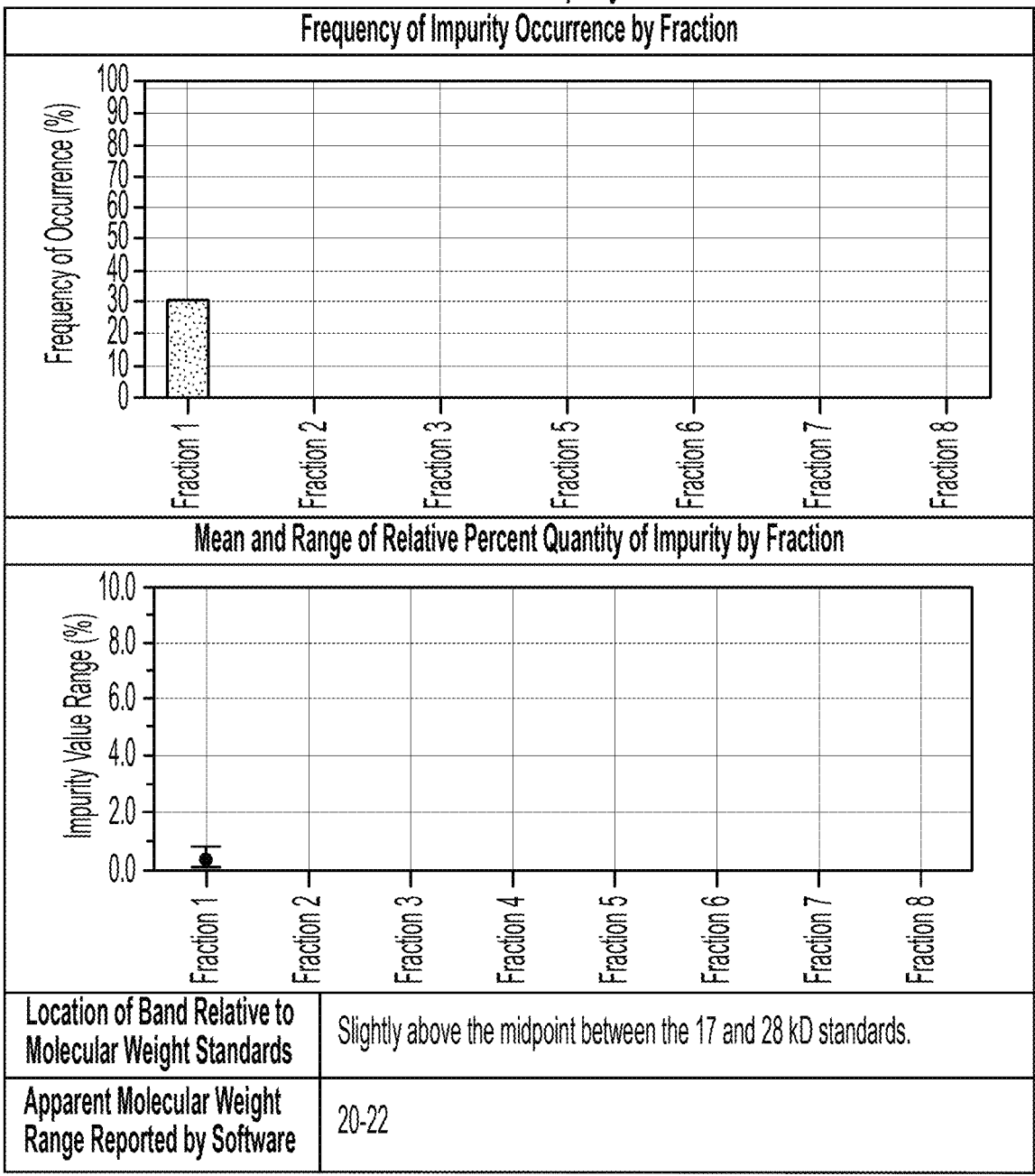
FIG. 9 shows the frequency of impurity occurrence by fraction and the mean and range of relative percent quantity of impurity by fraction for the AUX-II 25 kD impurity.
Figure 10:
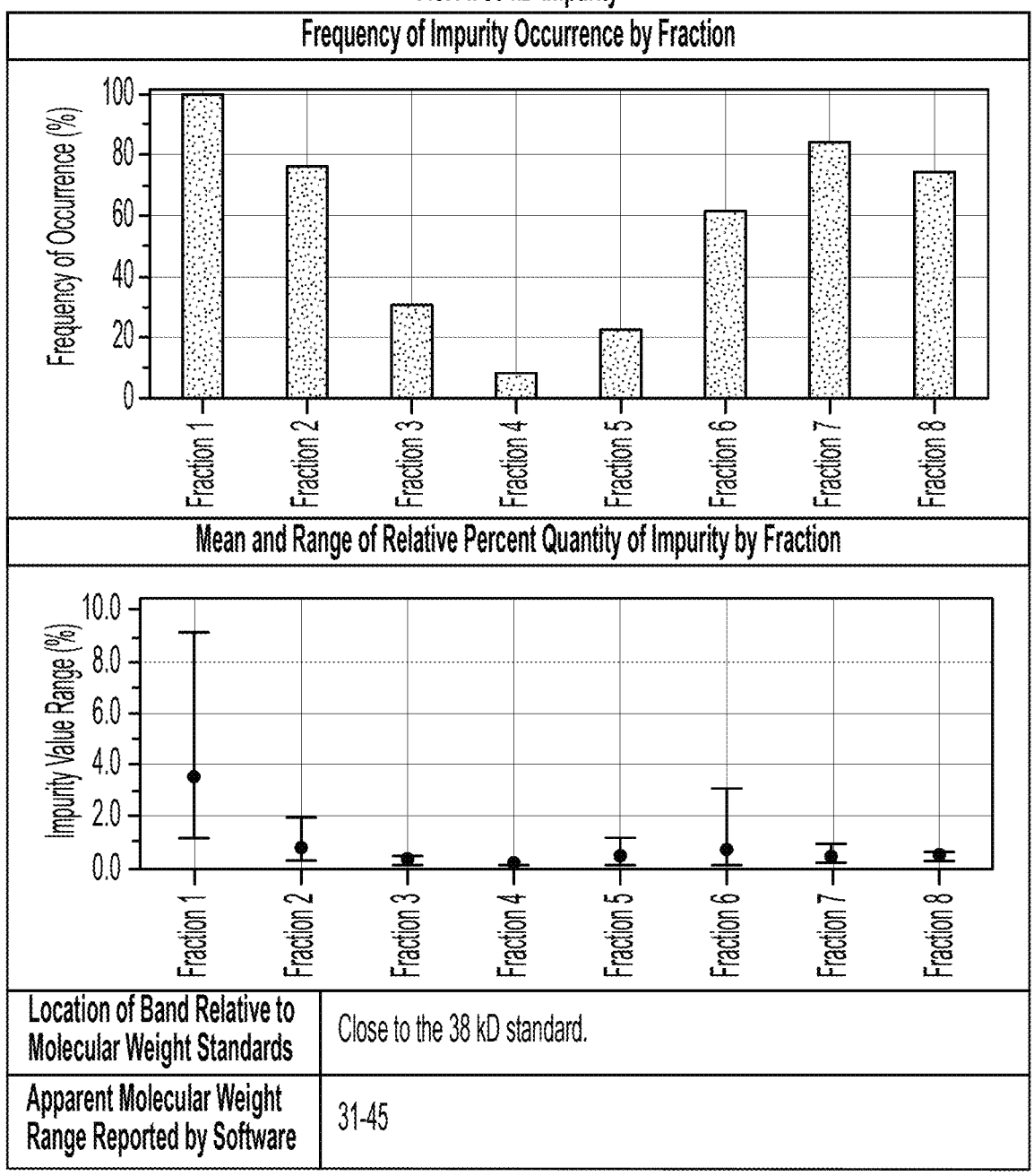
FIG. 10 shows the frequency of impurity occurrence by fraction and the mean and range of relative percent quantity of impurity by fraction for the AUX-II 38 kD impurity.
Figure 11:
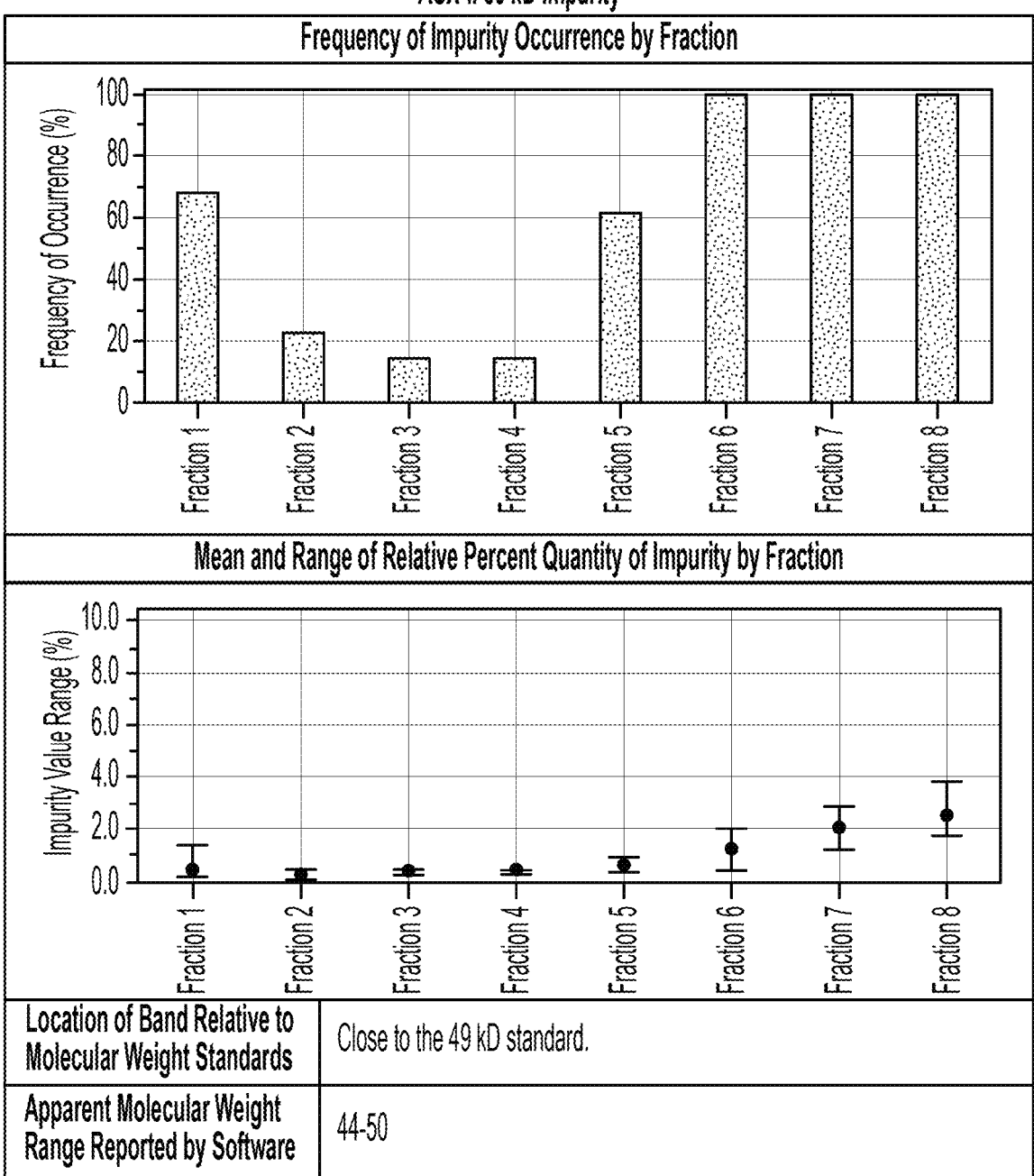
FIG. 11 shows the frequency of impurity occurrence by fraction and the mean and range of relative percent quantity of impurity by fraction for the AUX-II 50 kD impurity.
Figure 12:
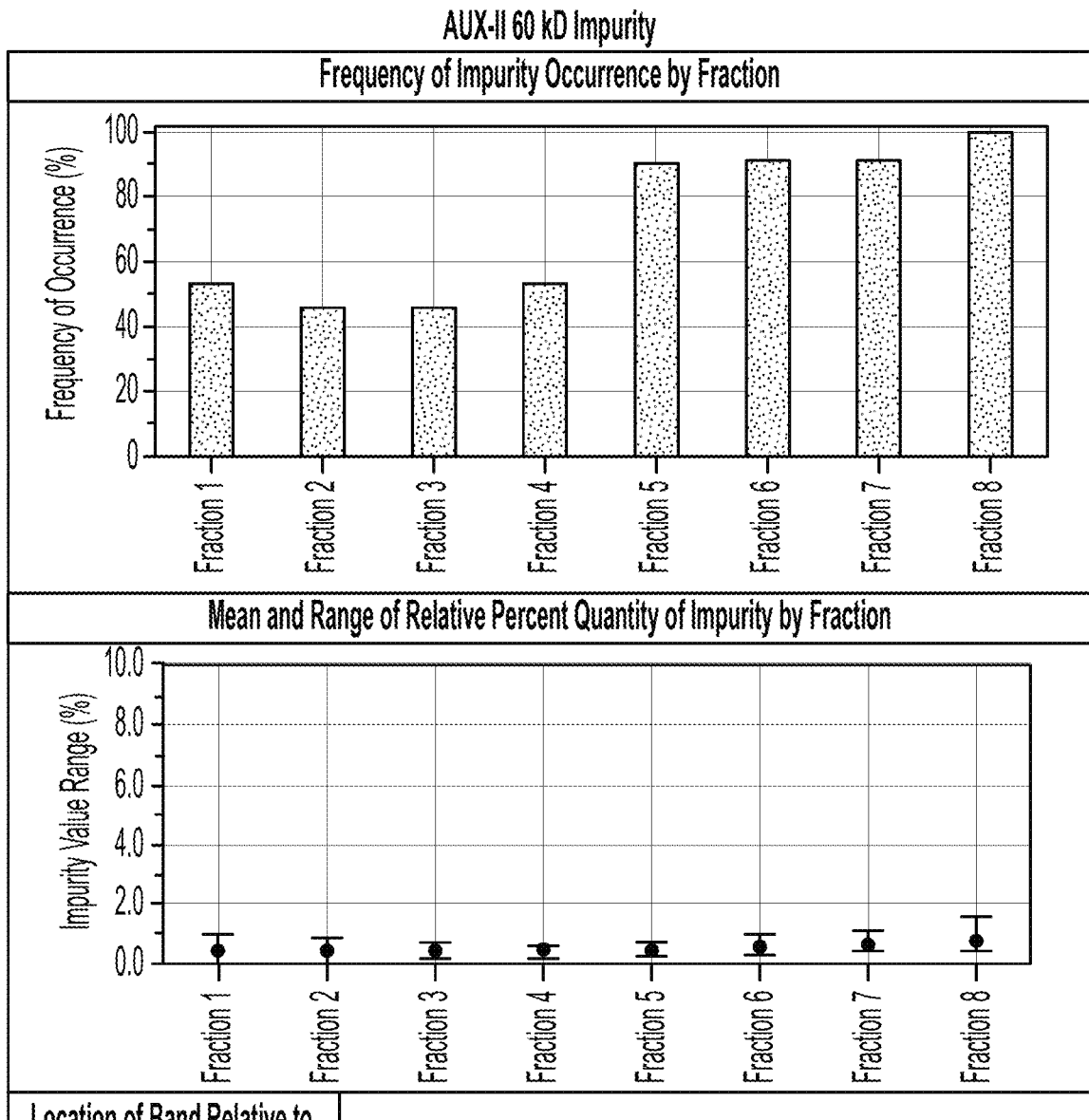
FIG. 12 shows the frequency of impurity occurrence by fraction and the mean and range of relative percent quantity of impurity by fraction for the AUX-II 60 kD impurity.
Figure 13:
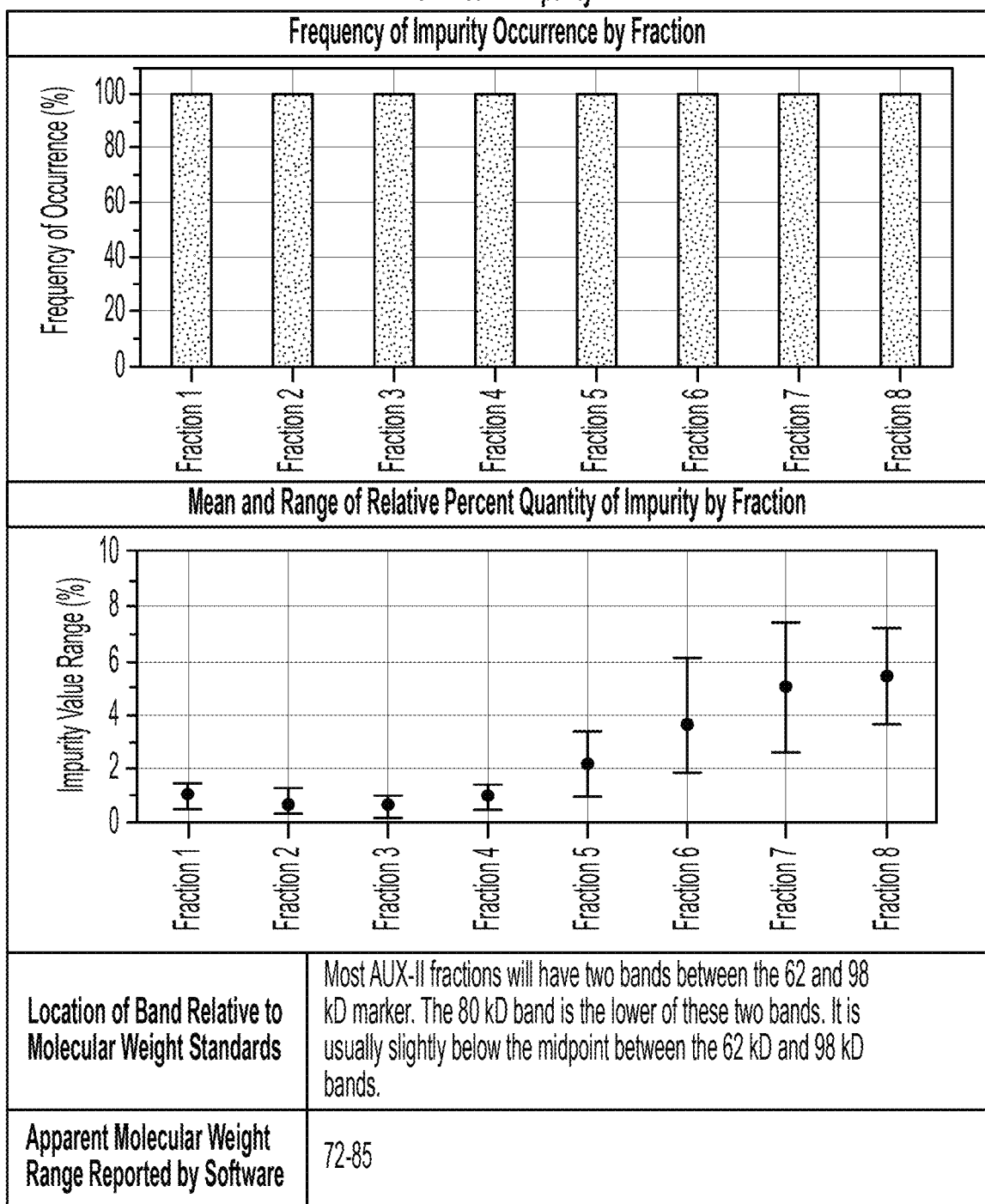
FIG. 13 shows the frequency of impurity occurrence by fraction and the mean and range of relative percent quantity of impurity by fraction for the AUX-II 80 kD impurity.
Figure 14:
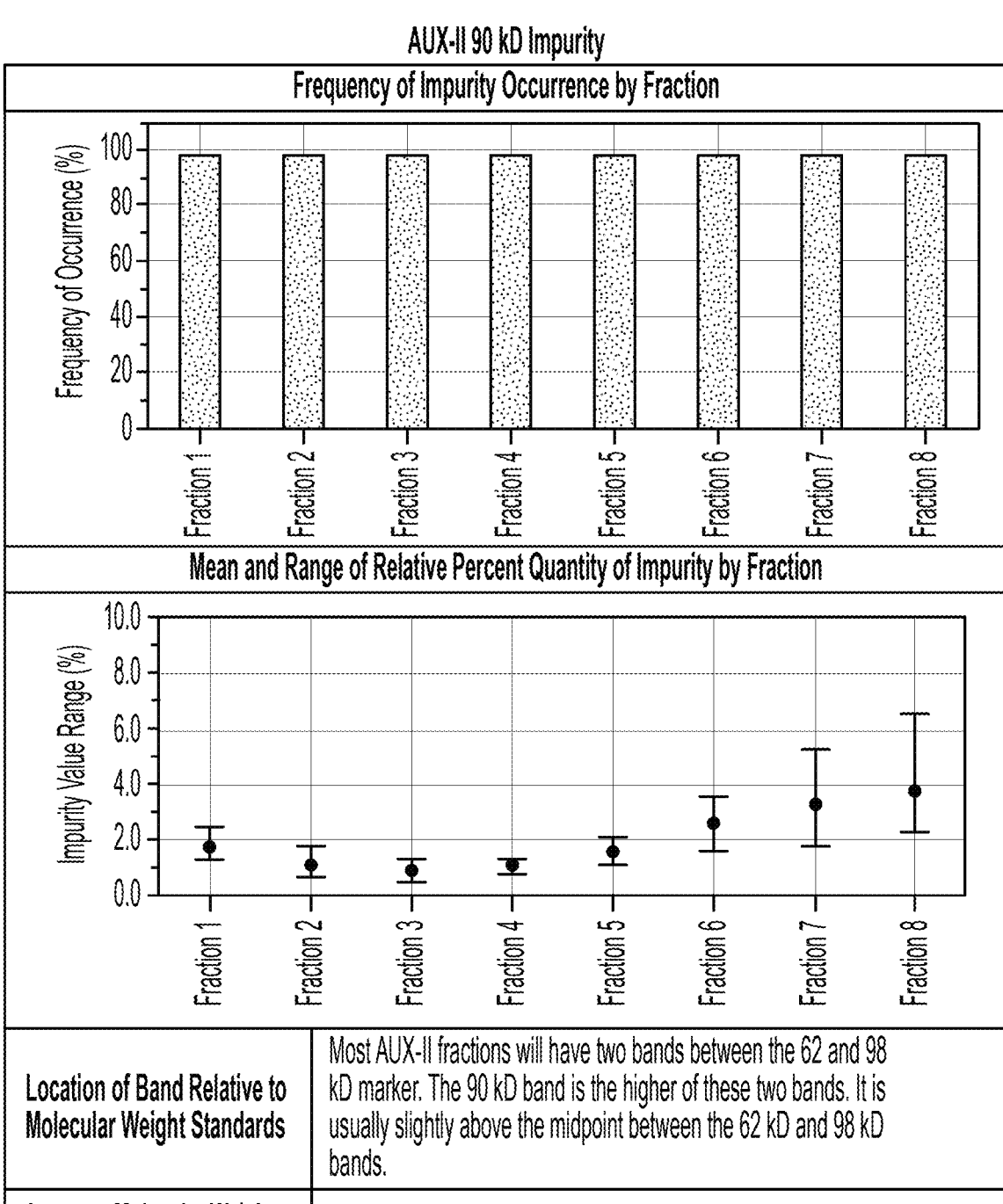
FIG. 14 shows the frequency of impurity occurrence by fraction and the mean and range of relative percent quantity of impurity by fraction for the AUX-II 90 kD impurity.
Figure 15:
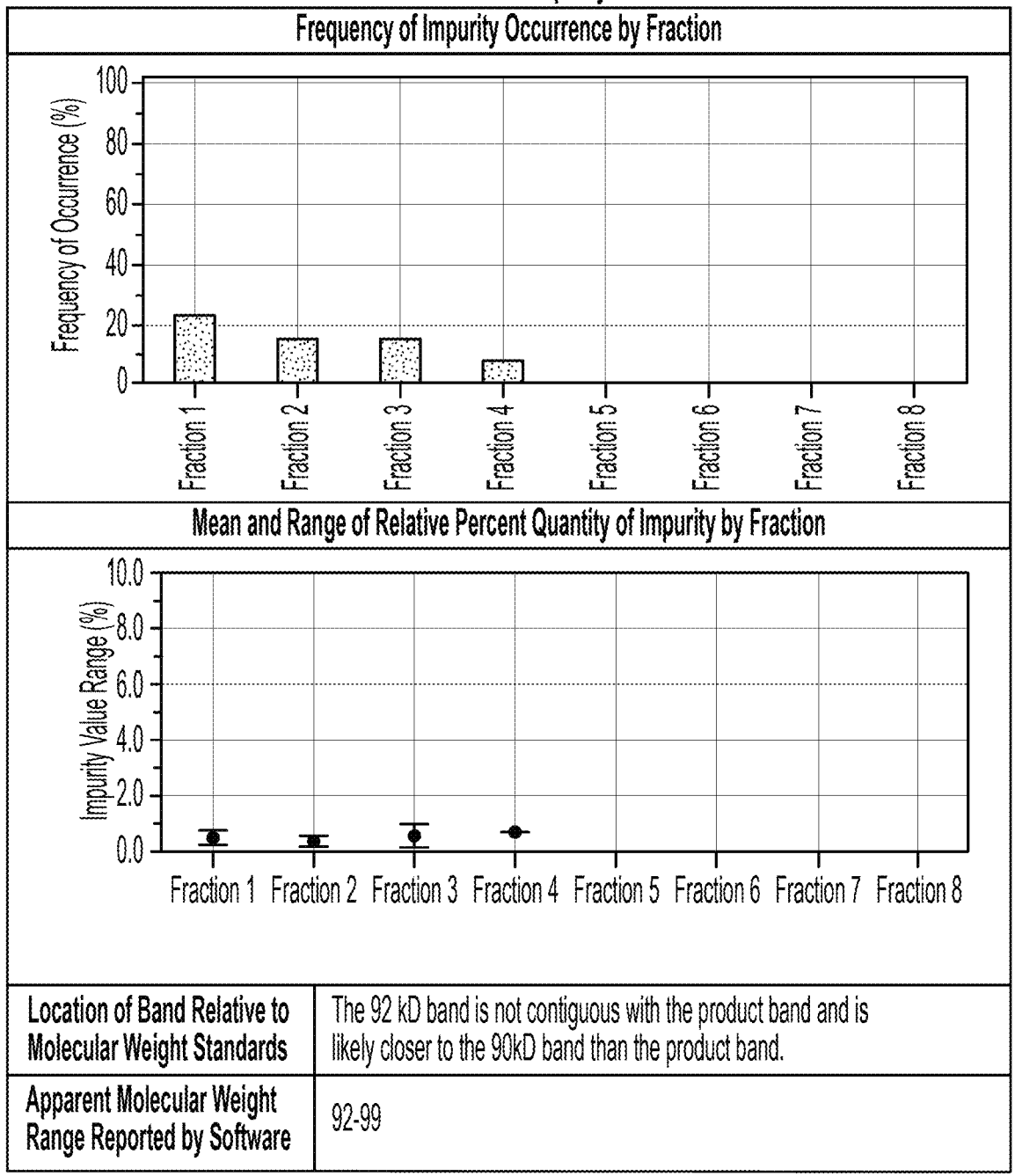
FIG. 15 shows the frequency of impurity occurrence by fraction and the mean and range of relative percent quantity of impurity by fraction for the AUX-II 92 kD impurity.

In FIG. 2, Lane 1 contains a molecular weight standard with bands of a known molecular weight. Lane 2 contains the appropriate AUX Intermediate reference standard. The remaining lanes contain a sample from each IEX fraction. The main product band is the top band of each lane and each additional lower band represents an impurity.

Trend analysis of the impurities observed in the IEX fractions can provide important process performance information. The impurities should be consistently categorized, based on molecular weight, from lot-to-lot for a successful trending analysis. While densitometry software may report an apparent molecular weight for each impurity, categories based on the reported apparent molecular weight have some normal variation in the gel image and the variation combined with the close proximity of the bands can lead to ambiguous and overlapping classification ranges. Instead, recommended molecular weight categories for the AUX-I and AUX-II impurities can be based on a visual comparison of the vertical (y-axis) position of the fraction impurities relative to the vertical position of the bands in the known molecular weight lanes.

A total of 128 AUX-I fractions and 99 AUX-II fractions were analyzed. Impurities that appeared in three or more of the 13 batches were assigned a category. A description of each category is provided below.

ii. Impurity Classification Results

AUX-I

AUX-I fraction impurity categories include: 33 kD, 45 kD, 55 kD, 80 kD, 90 kD, and 96 kD. A description of each impurity category is provided in FIG. 3 through FIG. 8. Each figure includes:

First Panel: The percent frequency that the given impurity was observed in each fraction of 13 lots included in the assessment.

Second Panel: The mean (dot) and range (error bars) of the relative quantity (reported as percent) for the given impurity by fraction number.

Third Panel: A description of the visual vertical location of the band relative to the molecular weight standards.

Fourth Panel: The range of apparent molecular weights reported for the given band by the software.

AUX-II

AUX-II fraction impurity categories include: 25 kD, 38 kD, 50 kD, 60 kD, 80 kD, 90 kD, 92 kD, and 96 kD. A description of each impurity is provided in FIG. 9 through FIG. 16. The figure panels are the same as described for AUX-I.

Of the 877 impurity bands analyzed, 3 bands were not appropriate for the above categories and were classified as "Other". Details of these impurities are included in Table 2.

TABLE 2

| Impurities Classified as "Others" | | | | | |
|---|---|---|---|---|---|
| AUX Peak | Batch Number | Fraction Number | Method Assigned Molecular Weight | Visually Assigned Molecular Weight | Relative Quantity (%) |
| AUX-I | C50-1000413 | 1 | 36.31 | 40 | 0.2 |
| AUX-II | C50-1000375 | 1 | 26.14 | 30 | 0.3 |
| | C50-1000413 | 2 | 67.87 | 62 | 1.2 |
| | | | 57.26 | 57 | 1.8 |

C. Impurity Trending i. Approach to Impurity Trending

After the impurities are categorized, they can be trended to monitor process performance. Fraction impurity trending can be complex because there are multiple impurities, multiple IEX fractions at different protein concentrations, and results are reported as relative quantities. However, trending can be simplified by reporting fraction impurities as the percent of the impurity-of-interest relative to the total protein per AUX peak as described below.

The quantity of protein in each IEX fraction can be determined by multiplying the fraction volume by the fraction protein concentration by $UV_{A280}$. The resultant value is the grams of protein per fraction. A typical profile of the grams of protein per fraction is provided in FIG. 17.

Figure 18:
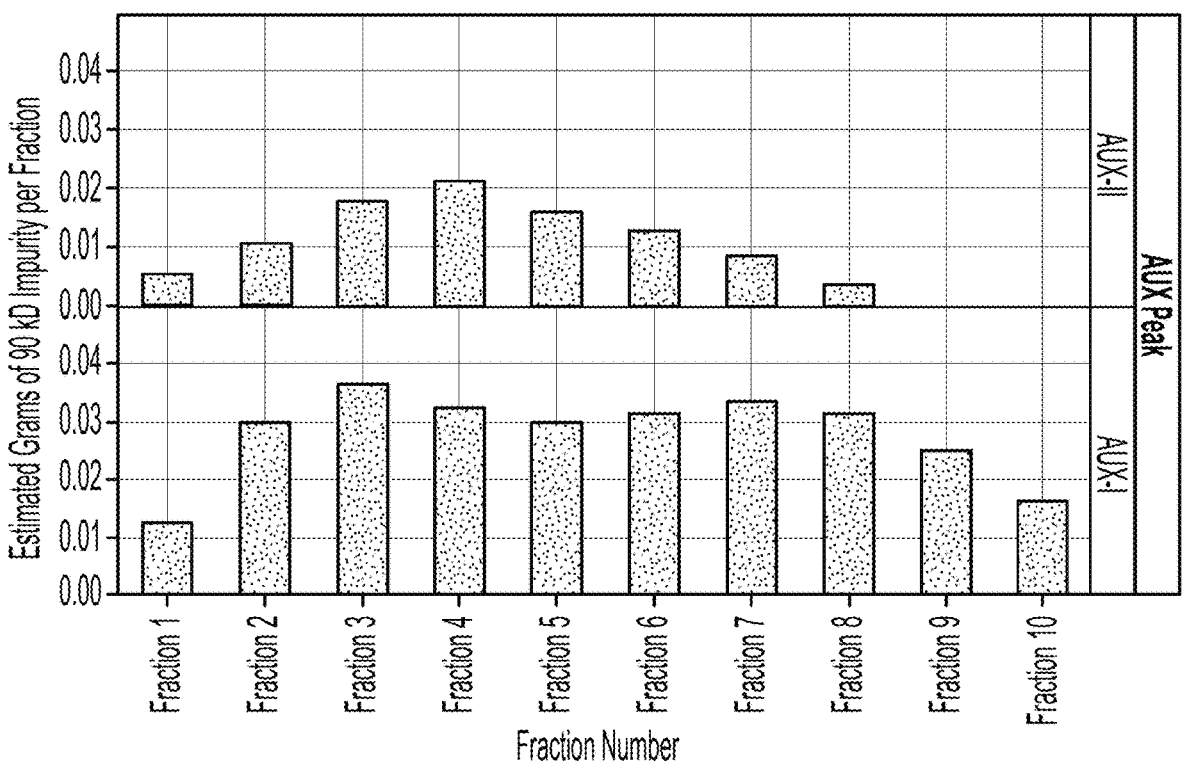
FIG. 18 illustrates a typical estimated grams of the 90 kD impurity per IEX fraction.

Utilizing SDS-PAGE and densitometry methods as described, results in IEX fraction impurities as a percent relative to total protein detected in each SDS-PAGE gel fraction lane. The same quantity of protein (1.5 μg protein/lane) is loaded into each fraction lane; therefore, the grams of each impurity in each fraction can be estimated by converting the impurity percentage to a decimal (dividing by 100), then multiplying by the grams of protein per fraction. For example, FIG. 18 shows a typical profile of the 90 kD impurity, which is commonly observed in both AUX-I and AUX-II fraction, expressed in grams.

Figure 19:
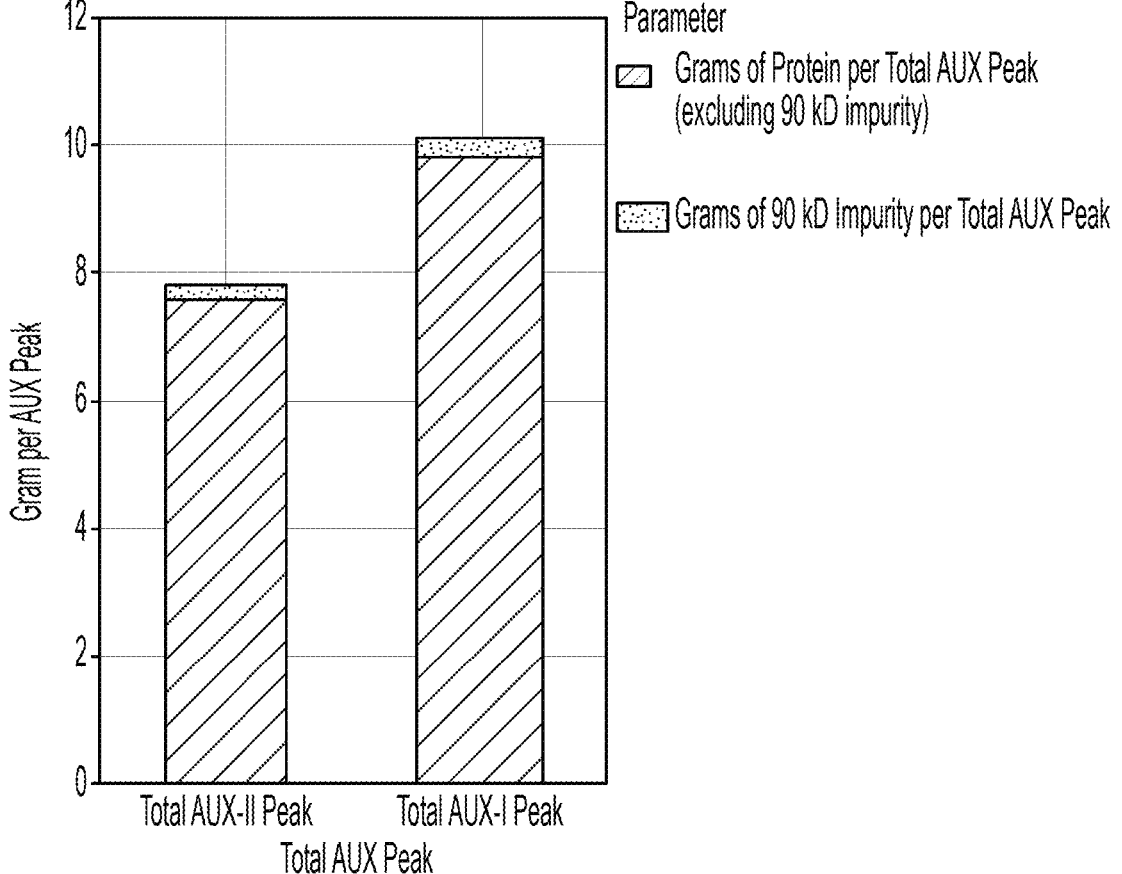
FIG. 19 shows estimated grams of 90 kD impurity relative to grams of protein per AUX peak.

The grams of protein for each AUX I, AUX II, or impurity can be calculated by fraction. Alternatively, the grams of protein per fraction and the impurity-of-interest can be summed by AUX peak. A visual representation of this mathematical operation is provided in FIG. 19.

The percent of the impurity-of-interest relative to the quantity of protein per AUX peak can then be calculated by dividing the grams of the impurity-of-interest by the total AUX peak grams of protein, then multiplying the resultant by 100 to convert the value to a percentage. The equation to get to the final value, expressed as the percent of the impurity-of-interest relative to the total protein per AUX peak, is summarized below:

$$\frac{\sum_{Fraction=i,impurity\ Category=j}^{Total\ Fractions,All\ Impurities\ Categories}\left(\frac{[Protein]_{i,j}}{L}\times V_{i,j}\times\frac{Impurity\ Value_{i,j}}{100}\right)}{\sum_{Fraction=i}^{Total\ Fractions}\left(\frac{[Protein]_i}{L}\times V_i\right)}\times 100$$

where:

[Protein]$_{i,j}$ is the protein concentration of the ith fraction containing the jth impurity $V_{i,j}$ is the volume in liters of the ith fraction containing the jth impurity Impurity Value$_{i,j}$ is the percent impurity of the jth impurity in the ith fraction

[Protein]$_i$ is the protein concentration of the ith fraction by $UV_{A280}$ $V_i$ is the volume in liters of the ith fraction L is one liter The above equation can be used to trend the quantity of each of the impurities detected to assess process performance. The above equation can also be easily modified to express the relative quantity of the impurity-of-interest in only the fractions that were forward processed.

Trending can be performed using a variety of methods. One method uses Shewhart control charts for individual values. A Shewhart control chart for individuals is a statistical tool used to distinguish between results that are due to routine variation (within the control chart limits) and results that are due to exceptional variation (beyond the control limits). The control limits are calculated using the moving range of two successive observations to estimate the process variability. The green horizontal line in the control charts represents the average result. Red horizontal lines represent the upper and lower control limits calculated as $\overline{X}\pm2.66\times\overline{mR}$, where $\overline{X}$ is the average and $\overline{mR}$ is the average moving range.

Limits generated using Shewhart control charts for individual values are not intended to indicate product quality. Accordingly, results outside the control limits would not automatically indicate a quality impact, and would need to be evaluated holistically in the context of all available data.

ii. Impurity Trending Results

Figure 20:
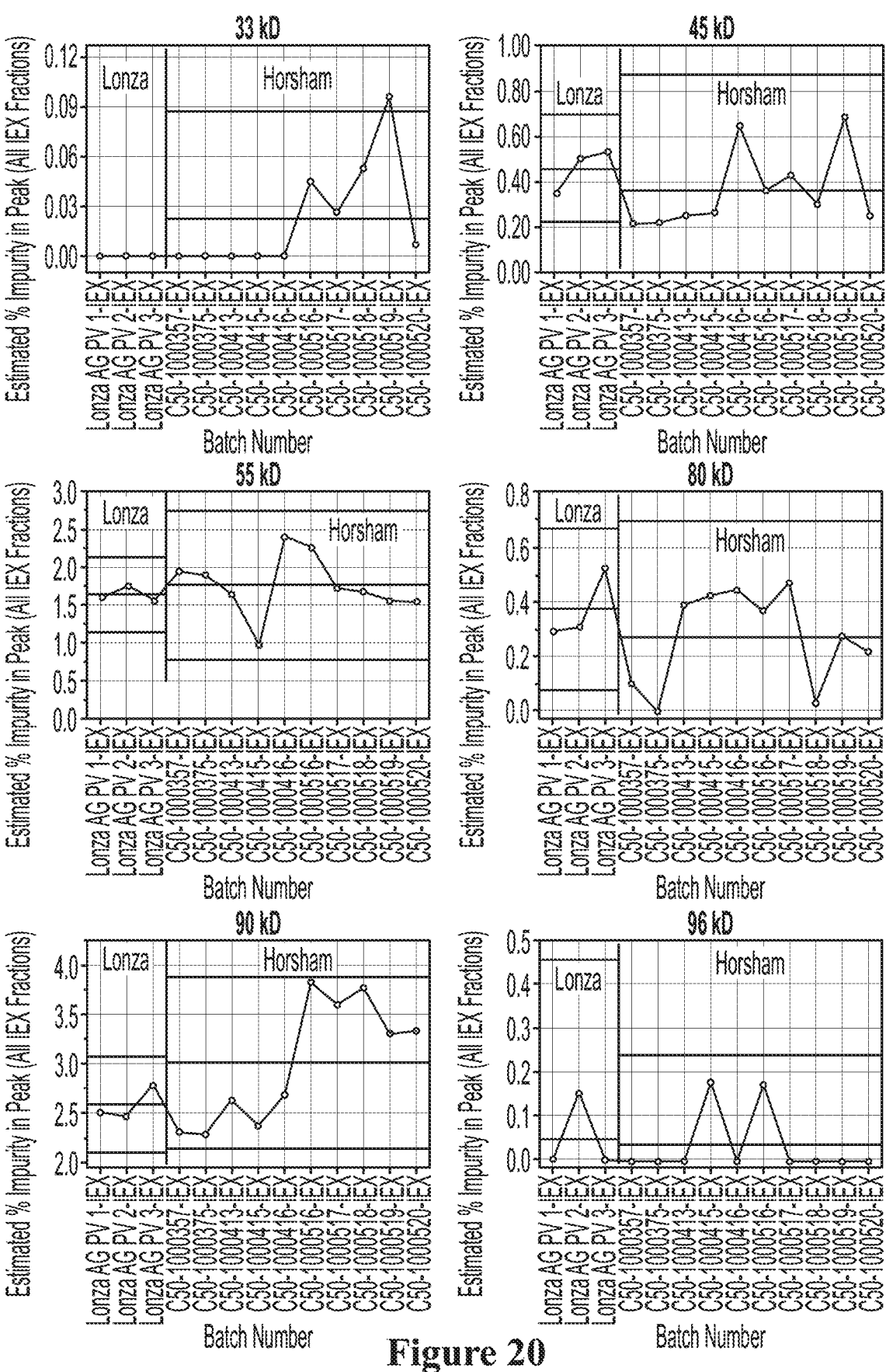
FIG. 20 shows control charts for AUX-I impurities.
Figure 21A:
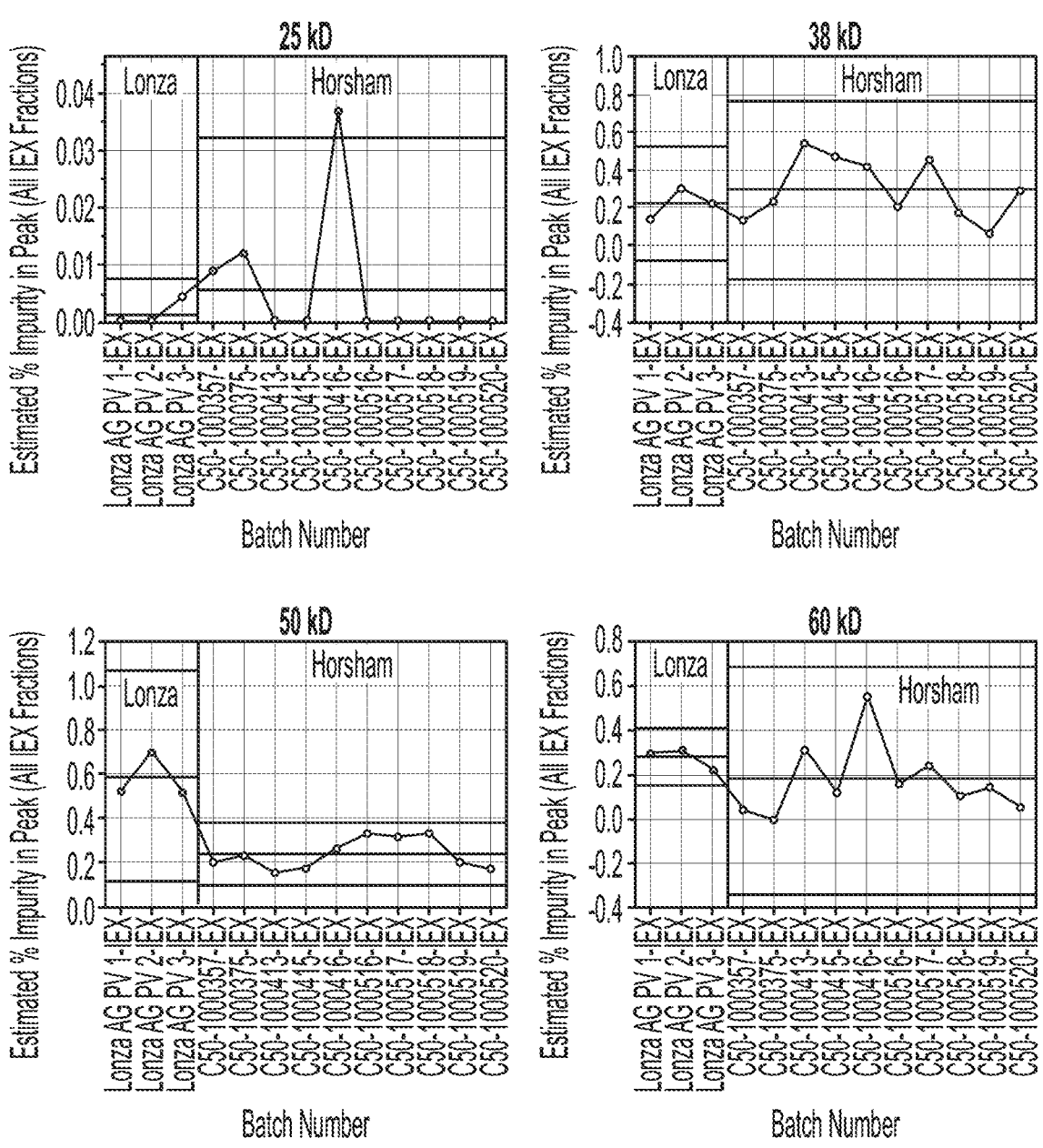
FIG. 21A and FIG. 21B show control charts for AUX-II impurities.
Figure 21B:
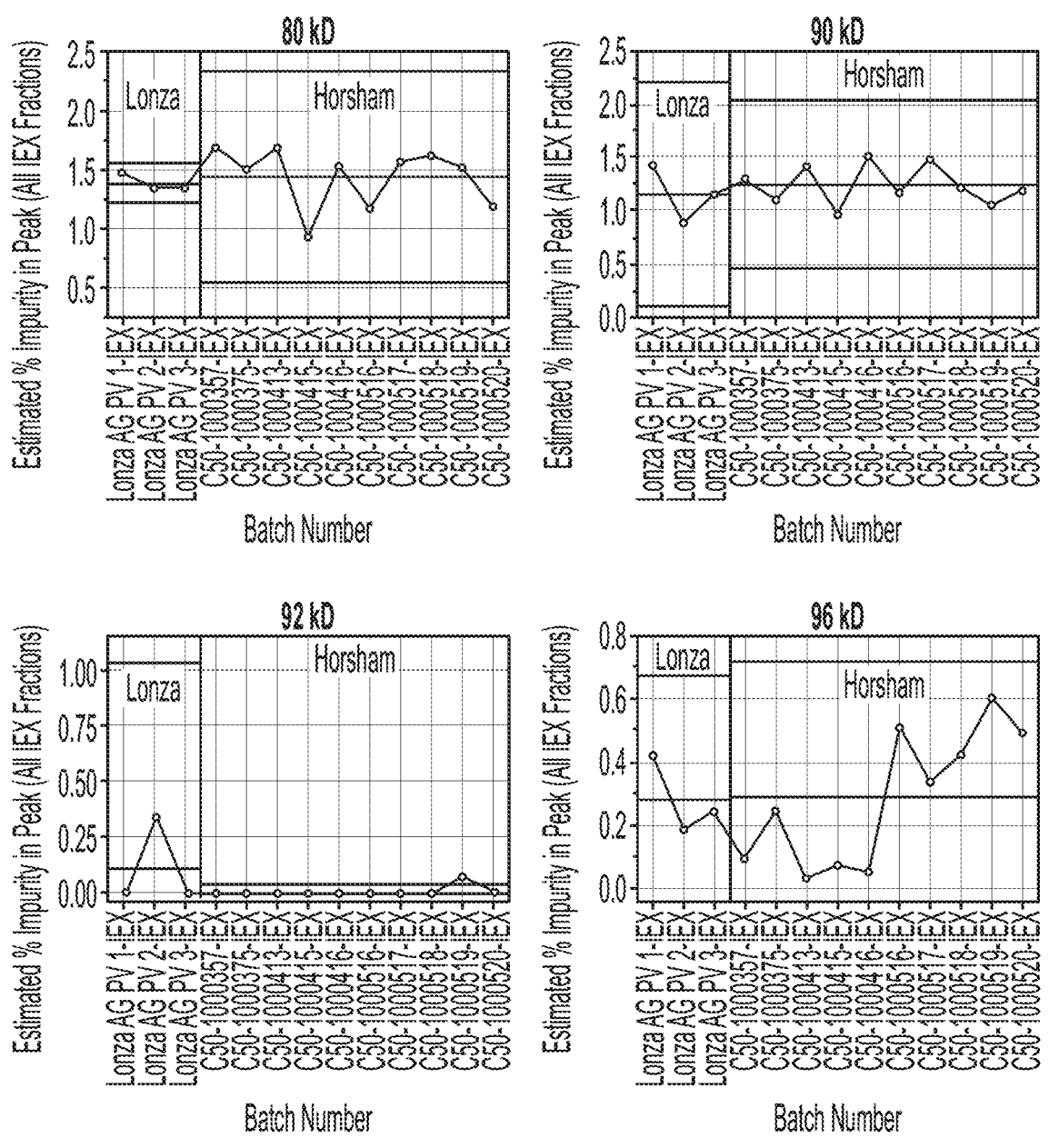

Shewhart control charts for individuals were used to trend the impurities of the lots listed in Table 1. AUX-1 impurities are trended in FIG. 20 and AUX-II impurities are trended in FIGS. 21A and 21B. The lots are phased by manufacturing site. Different x-axis scales were used for each control chart. The recommended impurity categories based on the assessment presented in this report are included in Table 3.

TABLE 3

| Common IEX Fraction Impurity Categories resolved using the Optimized SDS-PAGE Method | |
| --- | --- |
| AUX-I degradation products (MW) | AUX-II degradation products (MW) |
| about 33 kDa | about 25 kDa |
| about 45 kDa | about 38 kDa |
| about 55 kDa | about 50 kDa |
| about 80 kDa | about 60 kDa |
| about 90 kDa | about 80 kDa |
| about 96 kDa | about 90 kDa |
| — | about 92 kDa |
| — | about 96 kDa |
| Other | Other |

Trending of IEX fraction impurities can provide important process performance information. Reporting the impurities as the percent of the impurity-of-interest relative to the total protein per AUX peak is recommended to simplify impurity trending.

Example 2—Metals in the Purification Process

A. Abnormal Impurity Levels in the Manufacturing of Collagenase I and II Products A substantial decrease in purity of collagenase I and II products occurred during a normal manufacturing process. Analyses were performed, including determining the identity of the impurities seen after the ion-exchange chromatography (IEX) step of the manufacturing process. Collagenase I product has a molecular weight (MW) of about 113 kDa and collagenase II product has a MW of about 112 kDa. During routine manufacturing of collagenase, high levels of impurities occurred inexplicably, evident from the IEX step. These high levels of impurities appeared at 40 kDa, 50 kDa, 55 kDa, 80 kDa, 90 kDa, and 96 kDa on an optimized SDS-PAGE gel.

B. Potential Causes of Increased Impurity Products

The cause of the high levels of impurities was then investigated. *C. histolyticum* produces two proteases in addition to the collagenases (AUX-I and AUX-II), clostripain and neutral protease. Both proteases require metal cofactors for activity. Calcium is a cofactor for clostripain and is required for activity. Calcium is also a cofactor for neutral protease, but is only required for structural stability. If calcium is removed from neutral protease's binding sites the enzyme is degraded through autocatalysis. Zinc is a cofactor for neutral protease and is required for neutral protease activity.

Extensive product degradation in the manufacturing process stream was first detected following the hydrophobic interaction chromatography (HIC) unit operation during a manufacturing run. The HIC process buffer raw materials investigated included: Ammonium sulfate (AS), Tris-Base (tromethamine, or "Tris") and concentrated hydrochloric acid (HCl) at about 37%. The investigation included determination of the metal components in the raw materials. Ion coupled plasma mass spectroscopy (ICP-MS) was chosen to measure metal content due to its sensitivity and broad panel of metals which it can detect and quantify. ICP-MS has parts per billion (ppb) sensitivity for measuring thirty-four (34) metal ions, including calcium and zinc.

Trace metals tested by ICP-MS are presented below for each of the above raw material regarding the levels of calcium, nickel, and zinc. These particular metal levels were found in notably higher concentrations in some lots of ammonium sulfate tested (Tables 4-6) compared to Tris lots (Table 7) and HCl lots (Table 8). Tris-Base and concentrated HCl were ruled out for further testing based on the low levels of zinc, calcium, and nickel metals detected, as well as their relatively low concentrations used in the process buffers.

i. Ammonium Sulfate Testing:

TABLE 4

ICP-MS Trace Metals Data for Ammonium Sulfate Lots

| | Generated High Levels of Impurities (greater than 5% by area as measured by SDS-PAGE post IEX purification step) | | Low Levels of Impurities Generated (less than or equal to about 5% by area as measured by SDS-PAGE post IEX purification step) | | |
| Metal | Avantor Lot 70339 Rec# 1000726 (ppb) | Avantor Lot 99428 Rec# 1000979 (ppb) | Avantor Lot 335506 Rec# 1000476 (ppb) | Fisher Lot 147614A (ppb) | Fisher Lot 144586 (ppb) |
|---|---|---|---|---|---|
| Calcium | 770 | 960 | 870 | 2030 | 320 |
| Zinc | 84420 | 250 | 130 | 230 | 430 |
| Nickel | 1150 | 1020 | 170 | 130 | <100 |

Calcium was ruled out as causing the impurities because calcium levels of ammonium sulfate lots that generated low levels of impurities (less than or equal to about 5% by area as measured by SDS-PAGE) were higher than the lots of ammonium sulfate that cause high levels of impurities (greater than 5% by area as measured by SDS-PAGE). These data ruled out calcium contamination as a potential cause of collagenase I and II degradation to the impurities observed in the manufacturing runs. The lots of ammonium sulfate tested that generated high levels of impurities in collagenase manufacturing had increased levels of zinc and nickel present. These data suggested a possible link between nickel contamination and the product degradation observed. The influence of zinc on the manufacturing process was not clear by these data because both lots contained comparable high levels of nickel. The potential influence of zinc and nickel ion levels was explored in spiking studies discussed further below.

Historical lots of ammonium sulfate were also investigated.

TABLE 5

ICP-MS Trace Metals Data for Historic Ammonium Sulfate Lots

Low Levels of Impurities Generated (greater than 5% by area as measured by SDS-PAGE post IEX purification step)

| Metal | EMD Lot 46110619 (Rec# 2006-006) (ppb) | JT Baker Lot K46158 (Rec# 1000249) (ppb) | JT Baker Lot 25154 (Rec# 1000165) (ppb) | JT Baker Lot K21153 (Rec# 1000106, 1000147) (ppb) | Avantor Lot 33506 (Rec# 1000476) (ppb) |
|---|---|---|---|---|---|
| Calcium | 530 | 450 | 240 | 370 | 870 |
| Zinc | 140 | 1050 | 2980 | 2570 | 130 |
| Nickel | 140 | 180 | 180 | 150 | 170 |

TABLE 6

ICP-MS Trace Metals Data for EMD Millipore Emprove ® ACS, NF grade Ammonium Sulfate Low Levels of Impurities Generated (less than or equal to about 5% by area as measured by SDS-PAGE post IEX purification step)

| Metal | EMD Lot AM0556316 (Rec# 1001021) (ppb) | EMD Lot AM0464116 (Rec# N/A) (ppb) | EMD Lot AM0464316 (Rec# N/A) (ppb) | EMD Lot AM0464416 (Rec# N/A) (ppb) |
|---|---|---|---|---|
| Calcium | 400 | 350 | 180 | 240 |
| Zinc | 120 | 290 | 330 | 310 |
| Nickel | <100 | <100 | <100 | <100 |

Calcium levels for the five historic ammonium sulfate lots (Table 5) ranged from 240-870 ppb. Again, any elevated calcium levels did not generate the high levels of impurities seen in the manufacturing process abnormality. Zinc content ranged from about 130-2980 ppb. Nickel content of the historic lots ranged from about 140-180 ppb. Comparing these data to the nickel content of the two ammonium sulfate lots that generated high levels of product impurities, about 1150 ppb and about 1020 ppb respectively, the tolerance for nickel contamination is low. Although the relative difference in nickel between the ammonium sulfate lots is six to eight fold, this difference is much lower than other metals such as zinc, which varied greater than tenfold within the historic ammonium sulfate lots. Also, the low zinc content of Avantor ammonium sulfate lot 99428 (250 ppb) suggests the high level of impurities seen in the manufacturing process were highly nickel sensitive. In short, the investigation demonstrated that the products of the purification process were sensitive to both nickel and zinc levels in the process, but that the tolerance for zinc in the process was higher than the tolerance for nickel.

Calcium levels in the EMD-Millipore ammonium sulfate lots (Table 6) were lower than the deviation associated ammonium sulfate lots tested and were comparable to the historic ammonium sulfate lots calcium levels (Table 5). Zinc ion levels in the EMD-Millipore ammonium sulfate lots were generally lower than Avantor lots tested (Table 3). Nickel ion levels were below the limit of quantification (LOQ) of 100 ppb for the four development ammonium sulfate lots EMD-Millipore tested.

ii. Tris Testing:

The two lots of Tris-Base represent the raw material (Avantor lot 61712) used in commercial production prior to and through the manufacturing process that resulted in high levels of impurities, and a development material (Fisher lot 126928) used for lab scale investigational studies. As shown in Table 7, the Tris-Base contained comparable levels of calcium and nickel between the batches. The notable difference between the two lots was zinc content; the development material zinc content was below the LOQ, 100 ppb. Tris was discounted as a raw material contributing to collagenase degradation because the levels of nickel and zinc present in manufacturing processes generating high levels of impurities and low levels of impurities were very similar.

TABLE 7

| ICP-MS Trace Metals Data for Tris-Base | | |
| --- | --- | --- |
| Metal | Avantor Lot 61712 (Rec# 1000551) (ppb) (used in process where high impurity levels were found) | Fisher Lot 126928 (ppb) (used in process where low impurity levels were found) |
| Calcium | 690 | 850 |
| Zinc | 190 | <100 |
| Nickel | 460 | 410 | iii. HCl Testing:

Both HCl lots were raw materials used during the manufacturing process that generated the high level of impurities. Table 8 shows that the calcium levels were comparable to levels detected in the AS lots while zinc and nickel content were below the LOQ (100 ppb). HCl was discounted as a raw material contributing to collagenase degradation because the levels of nickel and zinc present for manufacturing processes generating high levels of impurities and low levels of impurities were very similar and below detectably limits.

TABLE 8

| ICP-MS Trace Metals Data for Concentrated HCl | | |
| --- | --- | --- |
| Metal | Avantor Lot 67027 (Rec# 1000608) (ppb) (used in process where high impurity levels were found) | Avantor Lot 72661 (Rec# 1000690) (ppb) (used in process where low impurity levels were found) |
| Calcium | 980 | 710 |
| Zinc | <100 | <100 |
| Nickel | <100 | <100 |

C. Zinc and Nickel Spiking Studies

Laboratory scale purification studies were executed using two different ammonium sulfate lots known to be essentially free of zinc or nickel (Fisher lot 1476214A, Table 4 and EMD lot AM0556316, Table 5) to determine if the presence of zinc or nickel at the relative concentrations detected in the deviation associated ammonium sulfate lots was responsible for the product degradation observed in manufacturing process that generated the high levels of impurities. Early investigational studies at lab scale using ammonium sulfate Fisher lot 1476214A produced typical numbers of passing AUX-I and AUX-II fractions, wherein nearly all of the AUX-I and AUX-II fractions have undegraded AUX-FAUX-II purities of at least 91.2% as measured by SDS-PAGE gel densitometry and the most abundant degraded AUX-I 0 or AUX-II impurity is no more than 5.8% as measure by SDS-PAGE gel densitometry. Testing of EMD ammonium sulfate lots showed zinc and nickel content below LOQ (<100 ppb).

Using these ammonium sulfate lots for the studies, control runs consisting of the qualified HIC and IEX small scale models were executed using as starting material thawed, previously frozen Mustang Q filtrate (MQF) from the manufacturing process that generated high levels of impurities. The MQF was processed through HIC, TFF, and IEX steps. Both the HIC and IEX steps were loaded at the mid-point of the validated load range for the chromatography step. All unit operations were executed under chilled conditions with a chromatography cabinet set to 10° C. for the HIC step and 4° C. for the IEX step. The IEX fractions were analyzed by SDS-PAGE with densitometry. Fractions that passed on for pooling required un-degraded collagenase I or II at 91.2% purity or higher and the most abundant degraded collagenase I or II impurity at 5.8% or less.

The zinc spiking study utilized ammonium sulfate from Fisher lot 1476214A. This study preceded the nickel spiking study, which utilized ammonium sulfate from EMD lot AMO556316. Both ammonium sulfate lots were determined to have less than 100 ppb levels of zinc and nickel.

In the zinc spiking study, ammonium sulfate from Fisher lot 1476214A was spiked with $ZnCl_2$ to raise the zinc concentration in the HIC buffer to about 84 ppm. IEX fraction results from material processed with the zinc spiked buffer were compared to IEX fraction results from material processed without the additional zinc added to the process buffer. For the nickel spiking study, ammonium sulfate from EMD lot AMO556316 was spiked with $NiCl_2$ to about 1.2 ppm. The studies are discussed separately below.

i. Zinc Spiking Study:

A control run, DEV-25C, produced typical results as measured by SDS-PAGE analysis of IEX fractions. DEV-25B, which was executed using zinc spiked buffer, resulted in significant degradation of AUX-I and AUX-II.

Figure 22:
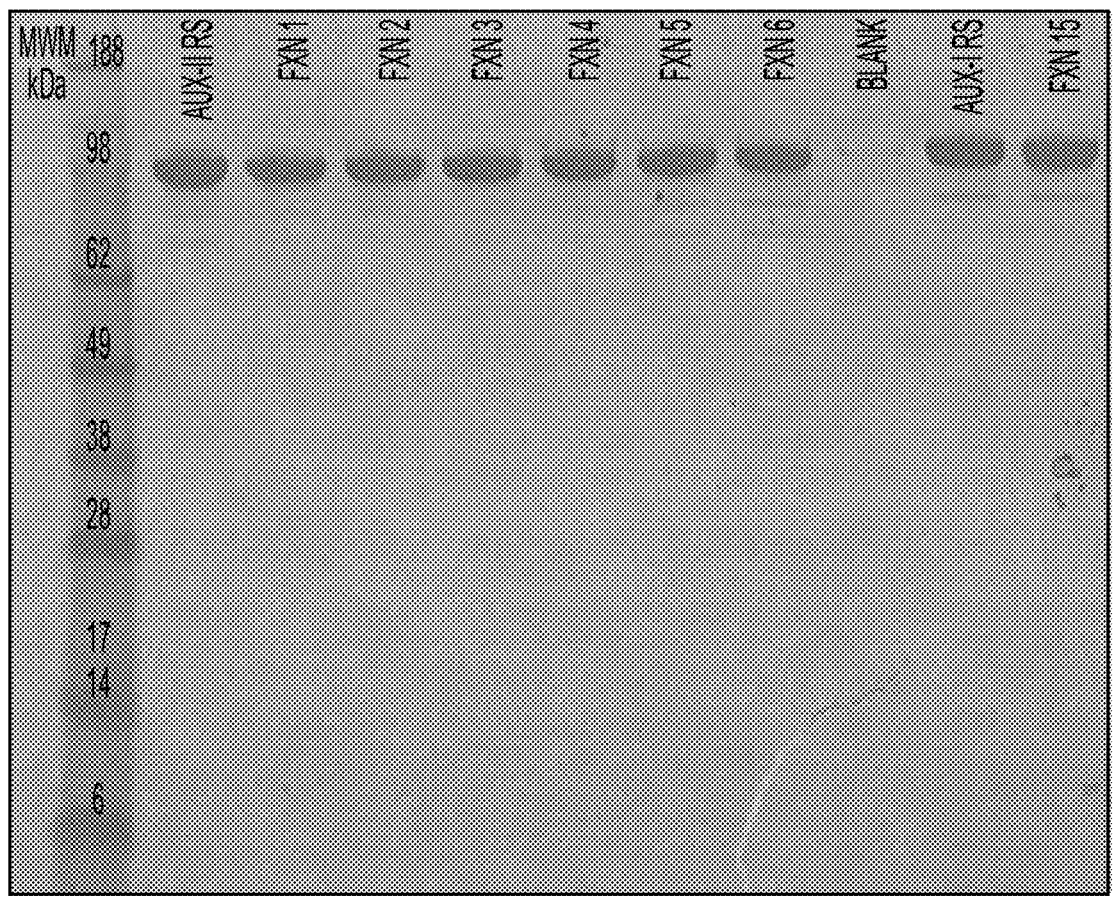
FIG. 22 is a SDS-PAGE Coomassie-stained gel showing impurities in AUX-II fractions after an IEX column during a control run from a zinc spiking study (DEV-25C). The AUX-II peak from the IEX column was collected in six (6) fractions. This gel shows the typical purity of the AUX-II fractions and the typical pattern of product-related impurities.

The IEX SDS-PAGE images for the control run, DEV-25C, are presented in FIGS. 22 and 23. Densitometry data for these figures are tabulated below in Tables 9 and 10. The AUX-II peak consisted of six fractions, of which, fractions one through five met pooling criteria. The last fraction failed pooling criteria, which is consistent with typical process performance (refer to FIG. 22 and Table 9). The AUX-I peak consisted of ten fractions (fractions 7-16), of which fractions nine through fifteen met pooling criteria. For an AUX-I fraction to meet pooling criteria, the fraction was required to be at least 91.2% purity of un-degraded AUX-I and the most abundant degraded AUX-I or AUX-II impurity to be at no more than 5.8% purity. Similarly, for an AUX-II fraction to meet pooling criteria, the fraction was required to be at least 91.2% purity of un-degraded AUX-I and the most abundant degraded AUX-I or AUX-II impurity to be at no more than 5.8% purity. Under these particular requirements, the first two AUX-I fractions (seven and eight) and the last AUX-I fraction (sixteen) failed pooling criteria (refer to FIG. 23 and Table 10). As the fractions represent a peak of AUX-I or AUX-II being purified, the bell-shaped purity curve across the fractions is usual.

TABLE 9

DEV-25C AUX-II Fractions Densitometry Results

| Fraction # | % Purity | % Most Abundant Impurity | Meets Pooling Criteria (Y/N) |
|---|---|---|---|
| 1 | 94.9 | 3.0 | Y |
| 2 | 98.1 | 1.5 | Y |
| 3 | 98.4 | 1.1 | Y |
| 4 | 97.3 | 1.8 | Y |
| 5 | 96.3 | 1.9 | Y |
| 6 | 89.9 | 3.8 | N |

TABLE 10

DEV-25C AUX-I Fractions Densitometry Results

| Fraction # | % Purity | % Most Abundant Impurity | Meets Pooling Criteria (Y/N) |
|---|---|---|---|
| 7 | 87.7 | 8.5 | N |
| 8 | 86.5 | 9.4 | N |
| 9 | 92.0 | 4.9 | Y |
| 10 | 95.8 | 2.3 | Y |
| 11 | 97.8 | 2.2 | Y |
| 12 | 97.1 | 2.9 | Y |
| 13 | 97.0 | 3.0 | Y |
| 14 | 96.8 | 3.2 | Y |
| 15 | 96.5 | 3.5 | Y |
| 16 | 89.8 | 6.7 | N |

By contrast, SDS-PAGE/densitometry analysis of the IEX fractions generated from the 84 ppm zinc spike run DEV-25B contained collagenase impurity fragments well above the maximum allowable limit (% most abundant impurity) of <5.8%. No AUX-I or AUX-II fractions met pooling criteria (FIGS. 24 and 25, Tables 11 and 12). This study shows that zinc contamination of the HIC buffers to the level found in ammonium sulfate from Avantor lot 70339 promotes collagenase degradation like that observed in the manufacturing process and generates high levels of impurities.

TABLE 11

DEV-25B AUX-II Fractions SDS-PAGE Densitometry Results

| Fraction # | % Purity | % Most Abundant Impurity | Meets Pooling Criteria (Y/N) |
|---|---|---|---|
| 1 | 66.4 | 27.8 | N |
| 2 | 75.5 | 20.7 | N |
| 3 | 79.5 | 17.9 | N |
| 4 | 76.7 | 20.2 | N |
| 5 | 72.1 | 22.2 | N |
| 6 | 63.9 | 22.5 | N |
| 7 | 52.9 | 24.4 | N |
| 8 | 45.0 | 29.2 | N |

TABLE 12

DEV-25B AUX-I Fractions SDS-PAGE Densitometry Results

| Fraction # | % Purity | % Most Abundant Impurity | Meets Pooling Criteria (Y/N) |
|---|---|---|---|
| 9 | 54.9 | 29.8 | N |
| 10 | 50.9 | 33.2 | N |

TABLE 12-continued

DEV-25B AUX-I Fractions SDS-PAGE Densitometry Results

| Fraction # | % Purity | % Most Abundant Impurity | Meets Pooling Criteria (Y/N) |
|---|---|---|---|
| 11 | 56.2 | 34.0 | N |
| 12 | 65.2 | 29.5 | N |
| 13 | 70.4 | 26.6 | N |
| 14 | 70.0 | 27.5 | N |
| 15 | 67.5 | 29.9 | N |
| 16 | 62.4 | 30.3 | N |
| 17 | 58.8 | 31.3 | N | ii. Nickel Spiking Study:

The IEX SDS-PAGE images for the control run, DEV-25A, are presented in FIGS. 26 and 27. Densitometry data for these figures are tabulated below in Tables 13 and 14. The AUX-II peak consisted of six fractions. All fractions met pooling criteria (refer to FIG. 26 and Table 13). The AUX-I peak consisted of ten fractions, of which fractions nine through fifteen met pooling criteria. The first three AUX-I fractions (fractions seven through nine) and the last AUX-I fraction (fraction sixteen) failing pooling criteria (refer to FIG. 27 and Table 14). Again, as the fractions represent a peak of AUX-I or AUX-II being purified, a the bell shaped purity curve across the fractions is usual.

TABLE 13

DEV-25A AUX-II Fractions SDS-PAGE Densitometry Results

| Fraction # | % Purity | % Most Abundant Impurity | Meets Pooling Criteria (Y/N) |
|---|---|---|---|
| 1 | 95.9 | 2.8 | Y |
| 2 | 97.1 | 1.9 | Y |
| 3 | 99.1 | 0.9 | Y |
| 4 | 98.2 | 1.3 | Y |
| 5 | 96.9 | 1.9 | Y |
| 6 | 92.3 | 4.2 | Y |

TABLE 14

DEV-25A AUX-I Fractions SDS-PAGE Densitometry Results

| Fraction # | % Purity | % Most Abundant Impurity | Meets Pooling Criteria (Y/N) |
|---|---|---|---|
| 7 | 85.6 | 8.5 | N |
| 8 | 85.2 | 9.1 | N |
| 9 | 90.7 | 4.9 | N |
| 10 | 95.5 | 3.3 | Y |
| 11 | 96.6 | 3.4 | Y |
| 12 | 97.0 | 3.0 | Y |
| 13 | 96.6 | 3.4 | Y |
| 14 | 96.8 | 3.2 | Y |
| 15 | 96.8 | 3.2 | Y |
| 16 | 90.8 | 6.4 | N |

By contrast, in Run 4 with spiked nickel, HIC buffers contained 1.2 ppm nickel chloride. The presence of nickel at 1.2 ppm in the HIC buffers generated product fragments in the AUX-I and AUX-II fractions comparable to those experienced in the manufacturing process generating high levels of impurities. No AUX-I or AUX-II fractions met pooling criteria (FIGS. 28 and 29, Tables 15 and 16). These results demonstrate that nickel contamination at 1.2 ppm in ammonium sulfate lots promotes collagenase degradation consistent with the high levels of impurities seen from the abnormal manufacturing process.

TABLE 15

DEV 25D AUX-II Fractions SDS-PAGE Densitometry Results

| Fraction # | % Purity | % Most Abundant Impurity | Meets Pooling Criteria (Y/N) |
|---|---|---|---|
| 1 | 74.8 | 19.5 | N |
| 2 | 81.8 | 14.4 | N |
| 3 | 84.6 | 10.9 | N |
| 4 | 85.6 | 10.2 | N |
| 5 | 83.0 | 11.1 | N |
| 6 | 72.3 | 13.3 | N |
| 7 | 64.9 | 16.0 | N |

TABLE 16

DEV 25D AUX-I Fractions SDS-PAGE Densitometry Results

| Fraction # | % Purity | % Most Abundant Impurity | Meets Pooling Criteria (Y/N) |
|---|---|---|---|
| 8 | 62.7 | 21.7 | N |
| 9 | 60.3 | 22.6 | N |
| 10 | 67.6 | 21.5 | N |
| 11 | 81.6 | 16.5 | N |
| 12 | 84.7 | 14.7 | N |
| 13 | 84.1 | 15.9 | N |
| 14 | 82.6 | 17.4 | N |
| 15 | 82.0 | 18.0 | N |
| 16 | 72.4 | 18.1 | N |
| 17 | 68.6 | 18.2 | N |

D. Isolation and Identification of Neutral Protease from HIC CIP Water Wash

Prior to the present invention, impurities in the form of fragments of collagenase I or II were thought to be the result of clostripain degradation, a known host cell contaminant during the collagenase purification process. Clostripain was thought to cleave collagenase I and II into fragments and it was known to be both present and active in *C. histolyticum* fermentations, as well as during the collagenase purification process. Previous homology modeling and genomic sequence analysis in Herber (U.S. 2015/0010532) had predicted that neutral protease (another cleaving enzyme) was secreted during fermentation, but that it was non-functional due to significant mutations in the auto-catalysis region between the C-terminal end of the prosequence region and the N-terminal end of the mature protein.

The increased level of impurities in a routine manufacturing process required further investigation. This investigation determined that the impurities were fragments of collagenase I (AUX-I) and collagenase II (AUX-II) generated by neutral protease from *C. histolyticum*. The amino acid sequences of AUX-I and AUX-II were used in the Peptide Cutter program on the bioinformatics resource portal ExPASy.org to generate theoretical protein cleavage site lists using clostripain and thermolysin cleavage rules. Thermolysin was selected as the model protease for neutral protease from *C. histolyticum* since it is in the holotype of the M4 family. Interrogation of cleavage sites generated by clostripain and thermolysin in AUX-I and AUX-II sequences resulted in positive matches of terminal cleavage sites for the majority of characterized, routine product fragments contained in the IEX fractions (40 kDa, 50 kDa, 55 kDa, 80 kDa, 90 kDa, and 96 kDa). A summary of the characterization of the major product fragments and their respective cleavage enzymes is summarized below in Table 17:

TABLE 17

IEX Fragments Characterization Data and Cleavage Termini Matches Using Clostripain and Thermolysin Cleavage Rules

| Fragment Class | Theoretical Mass | N-terminus | C-terminus | Clostripain | Neutral Protease |
|---|---|---|---|---|---|
| 40 kDa: AUX-I Peak | 33890 | Y686LPNEGDSKNSL (residue 686-697 of SEQ ID NO: 5) | EGSVGR991 (residues 986-991 of SEQ ID NO: 5) | No match | Y686 |
| 50 kDa: AUX-II Peak | 45404 | R584HAYKNPNEIYS (residues 584-595 of SEQ ID NO: 5) or H585AYKNPNEIYSE (residues 585-596 of SEQ ID NO: 5) | IEGSVG990 (residues 985-990 of SEQ ID NO: 5) or EGSVGR991 (residues 986-991 of SEQ ID NO: 5) | R584 | H585 |
| 55 kDa: AUX-I Peak | 49371 | L565VSDDYLKDHG (residues 565-575 of SEQ ID NO: 4) | ELRVNK1008 (residues 1003-1008 of SEQ ID NO: 4) | No match | L565 |
| 80 kDa: AUX-II Peak | 79009 | I1ANTNSEKYDFE (residues 1-12 of SEQ ID NO: 4) | PIAKVT693 (residues 688-693 of SEQ ID NO: 4) | No match | No match |
| 90 kDa: AUX-I Peak | 87872 and 87985 | Two species with same n-terminus I1ANTNSEKYDFE (residues 1-12 of | NEDTTTP776 (residues 770-776 of SEQ ID NO: 4) | No match | 1777 |

TABLE 17-continued

IEX Fragments Characterization Data and Cleavage Termini Matches
Using Clostripain and Thermolysin Cleavage Rules

| Fragment Class | Theoretical Mass | N-terminus | C-terminus | Clostripain | Neutral Protease |
|---|---|---|---|---|---|
| | | SEQ ID NO: 4) | or EDTTTPI777 (residues 771-777 of SEQ ID NO: 4) | | |
| 96 kDa: AUX-II Peak | H838 - 95968.17 I817 - 93541.72 R174 - 93196.71 R851 - 97507.97 V847 - 97038.38 | Not determined | Not determined | R174 R851 | I817 H838 V847 |

A full listing of the IEX fraction impurity categories from IEX fractions is described in Example 1 at Table 3. Impurities may occur at any one of the molecular weights (MW) recorded in Table 3; however, the most common impurities occur at 45 kDa, 55 kDa, 80 kDa and 90 kDa for AUX-I, and at 38 kDa, 50 kDa, 60 kDa, 80 kDa, and 90 kDa for AUX-II. Occasionally, impurities at molecular weights other than those specified in Table 3 may occur (designated as "other" in Table 3).

To generate purified neutral protease from *C. histolyticum*, a method to purify neutral protease from the clean-in-place (CIP) waste stream of the hydrophobic interaction chromatography (HIC) step was developed. Two liter fractions of the HIC CIP water wash effluent were manually collected across the peak. The fraction containing the peak maximum was concentrated tenfold, by volume, before buffer exchanging with six diavolumes of 10 mM Tris, 3 mM CaCl₂, pH 8.0 at 5° C. This operation was carried out using a single 0.1 m² Pellicon® 5 kDa nominal molecular weight cut off tangential flow filter. The concentrated buffer exchanged water wash was loaded onto a Q Sepharose High Performance (Q HP) column equilibrated with 10 mM Tris, 3 mM CaCl₂, pH 8.0. The column was washed after loading with the equilibration buffer prior to using a 25 column volume gradient from 0-50% buffer B (10 mM Tris, 3 mM CaCl₂, 360 mM NaCl, pH 8.0). Two clusters of merged peaks eluted from the column and were collected by automated fractionation. SDS-PAGE analysis with Coomassie staining showed that a 34 kDa protein eluted free of other protein species within the detectable limits, within the second peak cluster (FIG. 30, Gel lane 3). The peak maximum sample was buffer exchanged into 20 mM potassium phosphate and stored frozen at −70° C.

This waste stream, the water wash step of the HIC clean in place (CIP) procedure, is generated by flushing the HIC column with water for injection (WFI) following completion of the HIC unit operation prior to flushing the column with 0.5 M NaOH to commence CIP. The water wash caused elution of neutral protease from the HIC column. Isolation of neutral protease from this waste stream was successful, and confirms the enzyme's presence in collagenase manufacturing processes, albeit in the HIC process waste stream. The isolated neutral protease had an apparent molecular weight of 34 kDa.

The 80 kDa fragment was the only characterized fragment which did not match either protease cleavage rule using the Peptide Cutter program, due to a proline residue in the P2' position of potential cleavage site. However, the 80 kDa fragment was recreated by mixing AUX-I with either the process isolated neutral protease or with a commercial version of *C. histolyticum* neutral protease (from Serva). Further, evaluation of the cleavage site for the 80 kDa fragment using the MEROPS database revealed that thermolysin was capable of cleaving the Thr-693-Gly694 peptide bond to create the 80 kDa fragment from AUX-I. Accordingly, all five AUX-I and AUX-II product fragments that typically appear in the manufacturing of collagenase products are proteolytic cleavage products of neutral protease. Under manufacturing conditions, the 50 kDa and 96 kDa impurities can also be cleavage products from clostripain degradation.

The non-characterized 96 kDa fragment, present in AUX-II fractions was theoretically matched to multiple cleavage sites, both N- and C-termini, for both clostripain and neutral protease. The 96 kDa fragment was recreated by exposing AUX-II to the neutral protease. This in-silico analysis and the neutral protease digestion studies implicate neutral protease as the responsible enzyme for product fragment formation in *C. histolyticum* fermentations and/or purifications.

As stated above, the isolated neutral protease from the collagenase manufacturing process has an apparent molecular weight of 34 kDa. This indicates the prosequence of neutral protease had been cleaved whether by auto-activation or by another host enzyme, and suggests neutral protease is active in *C. histolyticum* manufacturing processes.

Next, an investigation was performed to determine whether the prosequence auto-cleaved itself to generate the active and mature neutral protease, even though it was predicted to be unable to do so. Identification of the N-terminus of neutral protease would provide key data to evaluate the autocatalysis competency of the proenzyme by comparing consensus sequence requirements for thermolysin to the sequence flanking the N-terminus of *C. histolyticum* neutral protease. The subsequent purified neutral protease was subjected to N-terminus identification and identified residue Gln220 as the N-terminus of the enzyme. This N-terminus matches the recently published N-terminus of *C. histolyticum* neutral protease by Maeda et al. in 2015.

Additionally, it was discovered that neutral protease, not clostripain, is the proteolytic enzyme which generates all of the routine collagenase fragments observed during the collagenase manufacturing process. Use of isolated neutral protease from the HIC CIP water wash in AUX-FAUX-II digestion studies generated product fragments consistent with the routine fragments apparent molecular weights, as determined by SDS-PAGE analysis. These digestion studies used neutral protease isolated from the manufacturing process as described above.

E. Identification of *C. Histolyticum* Neutral Protease N-Ter-minus

The N-terminus identity methods used were orthogonal, being Edman Degradation sequencing and N-terminus iden-tification by LC-MS/MS following digestion with Lys-C/ Trypsin. Samples for both tests were prepared from the same purification run and represented different fractions of the neutral protease elution peak. The Edman Degradation analysis identified the following five residues of the N-ter-minal region of neutral protease: Gln220-Ala224. The LC-MS/MS digest analysis identified a larger stretch of the N-terminal region of neutral protease, detected as two pep-tides in the analysis: Gln220Ala-Arg227 and Gly228-Lys236. The identified amino acids are highlighted in FIG. 31.

The hexapeptide consensus sequence region of the proen-zyme was examined using the identified N-terminus of neutral protease. The consensus sequence corresponds to the three residues of the C-terminus of the prosequence of thermolysin, combined with the N-terminus and subsequent two residues of the mature enzyme. For thermolysin, the consensus sequence is Val230LysSerIleTherGly236 (SEQ ID NO: 6). Ile233 is the N-terminus of thermolysin. The protease subsite nomenclature of Schechter & Berger will be used to describe the consensus sequence (refer to FIG. 32). The amino acid features needed for autocatalysis of ther-molysin are a nonpolar residue in position P3 (Gly, Ala, Ile, Leu, or Val), a polar residue or proline in position P1 (Ser, His, Glu, P) and nonpolar residue in position P1'. Inspection of thermolysin's consensus sequence shows that it satisfies all three requirements.

Using the identified N-terminus of *C. histolyticum* neutral protease (Gln220), the theoretical consensus sequence is Lys217SerCysGlnAlaThr222 (SEQ ID NO: 7). This hexa-peptide region does not follow any of the subsite features for autocatalysis, except that Cys219 is a polar residue; how-ever, it is not listed as a suitable residue in the rule. It is not clear based on the literature whether structural features of cysteine exclude it from the suitable residues of the P1 site or was not studied by the researchers. Based on thermoly-sin's autocatalysis sequence rules, *C. histolyticum* neutral protease should not be autocatalysis competent.

The full gene product sequence (secretion sequence, prosequence, and mature sequence) of *C. histolyticum* ATTC19401 neutral protease has been recently published by Maeda et al. 2015. The gene product was cloned and expressed to allow study of neutral protease substrate speci-ficity, resulting in an active neutral protease. Sequence alignment of recombinant neutral protease (ᵣnprA) and the *C. histolyticum* neutral protease gene product sequences resulted in 100% homology (refer to FIG. 33). Accordingly, it was determined that the neutral protease in the collagenase *C. histolyticum* (CCH) manufacturing process is autocataly-sis competent, is secreted as an inactive pre-proenzyme which self-cleaves the prosequence in the growth media to become a functional mature enzyme, and is a typical feature of CCH fermentations.

F. Investigating the Presence of Neutral Protease During the Manufacturing Process An investigation was performed to determine if the active neutral protease was unique to the abnormal manufacturing process run or a routine feature of the process. The colla-genase fragment patterns in the manufacturing process were analyzed. The degradation patterns of AUX-I and AUX-II IEX fractions in the abnormal manufacturing process run were consistent with typical fragment relative molecular weights in typical manufacturing process runs, but at much higher levels. Evaluating the cleavage site of each charac-terized product fragment against clostripain and neutral protease cleavage rules suggested neutral protease was gen-erating the product fragments identified as impurities. SDS-PAGE analysis of the entire HIC unit operation, including the CIP waste stream, was undertaken to determine if a protein band of approximately 34 kDa was present in both of the process streams. The water wash portion of the CIP method contained a band consistent with this apparent molecular weight by SDS-PAGE evaluation. The HIC water wash sample was also shown to degrade AUX-I and AUX-II (similar to the pattern observed in the abnormal manufac-turing process run) in analytical spiking studies.

Besides these steps in the collagenase manufacturing process, residual neutral protease was found in HIC eluate and TFF-1 concentrate product streams. Investigation of IEX fractions, AUX-I and AUX-II IEX pools, AUX-I inter-mediate, AUX-II intermediate, and drug product revealed that neutral protease was sequestered to the tail AUX-I fractions of the IEX unit operation, where it co-eluted with the AUX-I peak tail. These fractions may be eliminated from the product stream due to the fractions failing in-process purity limits of the SDS-PAGE/densitometry analysis.

Example 3—Process Controls

Neutral protease activity was found in Mustang Q filtrate, HIC eluate, and tangential flow filtration (TFF) concentrate process samples of three manufacturing process runs. IEX AUX-I fractions of a routine manufacturing run were tested in neutral protease Zymography activity assays and the protease showed activity in tail fractions of these samples. These data suggest that residual neutral protease co-eluting from the HIC column is sequestered in the tail AUX-I fractions eluting from the IEX column. Most of the tail fractions will fail purity in-process limits of the SDS-PAGE densitometry fraction testing and so will not pooled to generate the AUX-I intermediate. However, additional pro-cedural controls have been implemented that ensure that fractions containing low amounts neutral protease are not forward processed. The additional procedures serve to reject additional AUX-I tail fractions from forward processing. The apparent positional nature of neutral protease elution, suggested by the Zymography activity analysis, shows these procedures act to eliminate neutral protease from the product stream prior to formulating the drug product. These process controls will be discussed below.

Zymography is an electrophoresis based enzymatic activ-ity assay that utilizes co-polymerized substrate (casein) within the SDS-PAGE gel, and certain enzymes' ability to renature upon removal of SDS from the gel. The renatured enzyme is allowed to incubate for a period of time after SDS removal to allow for degradation of the copolymerized casein substrate. The activity is detected by Coomassie staining where the degraded casein region, corresponding to the apparent molecular weight of the enzyme, appears as a white zone that does not absorb the stain. The remainder of the gel is stained blue by Coomassie dye complexing with the casein contained in the gel. Casein is bovine milk protein susceptible to proteolytic attack by *C. histolyticum* neutral protease, but not *C. histolyticum* clostripain or collagenases. Therefore, this PAGE based activity assay provided the ability to screen manufacturing product streams for the presence of active neutral protease.

The assay demonstrated neutral protease signals in the Mustang Q Filtrate, HIC eluate, TFF-1 concentrate, and the last IEX AUX-I tail fraction. The neutral protease is predominantly removed at the HIC step, remaining strongly bound to the column, eluting in the water wash of the column cleaning process. A trace amount of neutral protease co-purifies from the HIC column with the collagenases and binds to the IEX column. This trace amount of neutral protease begins to desorb from the column at the end of product collection in the last AUX-I fraction. Neutral protease can be removed by implementing at least one of the following elimination steps after separating collagenase I from collagenase II and collecting the respective elutes in fractions across the eluate peaks: (1) incorporating improved criteria limits for collagenase I, collagenase II, or both collagenase I and collagenase II fractions that may be pooled, (2) incorporating an improved fraction pooling strategy that rejects fractions containing detectable levels of neutral protease as tested by SDS-PAGE or Zymography electrophoresis, and (3) incorporating an about 1:1 (equal yield) pooling strategy of AUX-I and AUX-II purified fractions. The Zymography data and IEX process controls will now be discussed.

A. Improving Pooling—Collecting Only Fractions Free of Neutral Protease as Casein Zymography Electrophoresis Samples of laboratory scale runs of Mustang Q filtrate, HIC eluate, TFF-1 concentrate, AUX-I and AUX-II intermediates, and drug product were tested by Zymography electrophoresis. The data are presented in FIGS. 34 and 35. These samples were from two different runs (Dev-13 and Dev 25A) The Zymography images were scanned by densitometry and the annotated images used to assist in highlighting the neutral protease band as some sample types exhibited low neutral protease signal. To assist in band visualization, the inverse image of the gel was used to generate a typical Coomassie gel image (proteolytic band stained blue). Neutral protease was detected in early process samples such as MQF, HIC Load, and HIC eluate (refer to FIG. 34). The neutral protease band is easily observed at ~34 kDa apparent molecular weight in the MQF and HIC load samples. Note that the total protein load increases from 2 μg (MQF), 3 μg (HIC load), and 4 μg (HIC eluate) for these three sample types, yet the HIC eluate neutral protease response is substantially lower. The neutral protease band in the HIC eluate sample was faint enough to require highlighting using the 'select band' feature of the densitometry software. This demonstrates a significant clearance of the neutral protease across the HIC step.

A higher loading mass of 10 μg total protein was used for the TFF-1 concentrate, AUX-I and AUX-II pools, intermediates and drug product to amplify potential neutral protease signal in these samples. The TFF-1 concentrate (Dev-25A) sample contained neutral protease in sufficient concentration to generate a diffuse band at ~34 kDa. The AUX-I pool, AUX-I intermediate, and drug product contained detectable neutral protease, highlighted by the densitometry software and observable in lanes 6, 8, and 12 (refer to FIG. 35). The 34 kDa bands were visible in the gel; however, the resultant image was not of sufficient fidelity to clearly see the bands. AUX-II intermediate did not contain detectable neutral protease, nor did its predecessor AUX-II pool (FIG. 34). These data demonstrate neutral protease is separated from the product across the IEX step and co-elutes in the AUX-I peak as evident in the AUX-I pool and AUX-I intermediate. These data also demonstrate that any fractions containing detectable levels of neutral protease as measured by Zymography should be rejected and not included in the pooling step.

IEX fractions of AUX-I and AUX-II eluate peaks from a typical manufacturing process run the casein Zymography assay to determine if neutral protease was detectable in the fractions and if it was contained in a specific location. FIGS. 36 and 37 contain the gel images from the assays. None of the fractions of AUX-II contained neutral protease at concentrations detectable by this method. Select samples were run at higher concentrations to rule out neutral protease presence in the IEX fractions (refer to FIG. 38).

A low neutral protease signal was detected in the last AUX-I fraction (17) of this typical manufacturing run. This positional nature of neutral protease elution from the IEX column is illustrated in FIGS. 38 (lanes 9, 10) and 39 (lanes 8, 10, and 12). This detection again indicates that residual neutral protease (not cleared at the HIC or TFF-1 steps) partially desorbs from the IEX column at the end of AUX-I peak collection. The positional nature of the neutral protease contamination in the AUX-I peak tail of that manufacturing run and the inclusion of the last AUX-I fraction in the old manufacturing method's AUX-I pool explains the presence of neutral protease detected in AUX-I pool, AUX-I intermediate, and drug product of manufacturing run seen in FIG. 35. Accordingly, pooling fractions containing no detectable levels of neutral protease as measured by a casein Zymography assay can yield a collagenase composition essentially free of neutral protease.

The present invention may also include an auto-rejection feature. Prior to present invention, these AUX-I fractions were manually rejected during mixing of the passing AUX-I fractions to create the AUX-I pool. The auto rejection of at least the last two AUX-I fractions prevents residual neutral protease from entering the AUX-I intermediate, since it typically co-elutes in these fractions.

As described in the next sections, the implementation of an improved IEX pooling strategy removes this tail-end contamination during pooling of AUX-I fractions and AUX-II fractions.

B. Improving Pooling—Collecting Fractions that Meet Minimum Purity Limits as Measured by SDS-PAGE The collagenases, AUX-I and AUX-II, elute from the IEX column as discrete peaks during the gradient elution with AUX-II eluting first, followed by AUX-I. The peaks are collected by manual fractionation in about one liter aliquots. These fractions are tested for purity using SDS-PAGE with densitometry. Contiguous AUX-I or AUX-II fractions are available for pooling to create collagenase I product or collagenase II product. Historically, fractions of AUX-I or AUX-II that were pure to at least 88.5% by area as measured by SDS-PAGE with densitometry and had no single impurity greater than 10% by area as measured by SDS-PAGE with densitometry were pooled to generate collagenase I product or collagenase II product. Fractions failing these limits were not forward processed and thus, eliminated from the product stream.

Improving the criteria for passing fractions improves not only the overall purity of the collagenase compositions, it also serves to further eliminate neutral protease from the AUX-I tails. Raising the limits for passing fraction can remove neutral protease when AUX-I and AUX-II fractions have a purity of AUX-I or AUX-II of at least 91.2% by area as measured by SDS-PAGE with densitometry, and the highest single impurity to be no greater than 5.8% by area as measured by SDS-PAGE with densitometry.

As part of the investigation, a planned deviation to pool AUX-I and AUX-II fractions based on historical batch data was carried out. AUX-I fractions 12-16 and AUX-II fractions 2-5 were pooled and forward processed to create drug substance (sometimes called bulk drug substance or BDS). Release testing of the drug product resulted in out of specification (OOS) purity of the higher limits by SDS-PAGE and out of trend (OOT) purity by reverse phase HPLC (RP-HPLC), confirming the lower purity of the IEX fractions. This planned deviation resulted in the data presented in FIG. 35. The neutral protease detected in the AUX-I pool, AUX-I intermediate, and drug product from the manufacturing run was contributed by the tail AUX-I fraction (16) which was pooled as per the planned deviation. The limit of detection on the Zymography electrophoresis assay is about 0.5 ng of neutral protease. The bands in FIG. 35 were visible on the actual casein Zymography gel itself, but were just below the 0.5 ng limit—approximately 0.2-0.3 ng of neutral protease using a 10 microgram load amount of collagenase composition.

C. Improving Pooling—Matching AUX-II Yield to Minimize Excess AUX-I Yields

The present invention may also include evaluating the theoretical gram amount of AUX-II generated by pooling the passing AUX-II fractions and pools passing AUX-I fractions to generate a pool of about 1:1 mass ratio of AUX-I to AUX-II at the pooling step. For example, the amount of AUX-I pooled may be 1.3 times the grams of AUX-II. Any excess of AUX-I or AUX-II can be disposed of after manufacturing the Bulk Drug Substance (collagenase composition). This typically results in one or more tail AUX-I fractions that have met the initial in-process limits to be excluded from the AUX-I pool. This implementation is a secondary process control for eliminating neutral protease in the manufacturing process.

As an example, the peak fractions of collagenase I fractions collected from an IEX elution are forward processed based on the fraction meeting the desired purity and impurity criteria, along with pooling only collagenase I peak fractions until the approximate amount of collagenase I pooled matches the approximate amount of collagenase II produced by the process. First, a theoretical amount of total AUX-II from the process can be calculated after AUX-II fractions have been collected, excluding the final tail fraction. Second, a theoretical amount of AUX-I in each fraction is determined. Then, beginning at the first AUX-I fraction containing a purity of at least 91.2% by area as measured by SDS-PAGE with densitometry and no single impurity greater than about 5.8% as measured by SDS-PAGE with densitometry, consecutive fractions are pooled for AUX-I until the amount of AUX-I pooled is about 1.3 times the total amount calculated for AUX-II. Collagenase compositions produced by this method are essentially free of neutral protease.

This control strategy results in the elimination of additional end fractions of the collagenase I peak, such that the pooled fractions of collagenase I are essentially free of neutral protease.

Example 4—Clearance of Neutral Protease from the Process

The amplification of intrinsic neutral protease activity due to nickel or zinc was demonstrated by the small scale spiking studies discussed above, resulting in higher impurity levels of the IEX fractions. Importantly, the neutral protease clearance study found detectable neutral protease activity in only one of the three HIC eluates included in the study (lot 0011338) while all three lots contained detectable neutral protease activity in the TFF-1 concentrate samples. The trace levels present in typical HIC eluate and TFF-1 concentrate do not promote elevated product fragments in the IEX fractions, yet the manufacturing process runs generating high levels of impurities and the small scale spiking study runs contained increased fragments present in HIC eluate, TFF-1 concentrate, and IEX fractions. These results suggest nickel and zinc ions amplify the neutral protease specific activity in the HIC and TFF-1 unit operations, causing increased product fragment impurities in the IEX unit operation.

A neutral protease clearance study was performed to confirm it is effectively eliminated from the product stream of the collagenase manufacturing process prior to creating the drug product. This study was executed on three historic drug product lots by testing product stream retain samples of the downstream process using two recently developed neutral protease activity based test methods: (1) rejection from the AUX-I pooling steps of AUX I elution fractions from the ion exchange step containing detectable levels of neutral protease, as measured by SDS-PAGE or Zymography assays, and (2) pooling maximum peak fractions of AUX I based on an approximate 1:1 mass ratio of AUX II pooled from the ion exchange step. The product streams tested in this study are listed in Table 19 below. The test methods for detection of neutral protease activity in manufacturing product streams are a fluorescence based microplate assay and a SDS-PAGE Zymography method. The data from each of these test methods will be discussed separately below.

TABLE 19

| Product Streams Tested for in the Neutral Protease Clearance Study | |
| --- | --- |
| Sample Type | *C. Histolyticum* Collagenase Lots Tested |
| Mustang Q Filtrate | Drug Product Lots 1-3 |
| HIC Eluate | 0009749, 0010987, 0011338 |
| TFF-1 Concentrate | |
| AUX-I Pool | |
| AUX-II Pool | |
| AUX-I Intermediate | |
| AUX-II Intermediate | |
| Bulk Drug Substance | |

A. Fluorescent Microplate Neutral Protease Activity Assay

The sample types listed in Table 19 were tested using the semi-quantitative fluorescent activity assay. This assay utilizes a commercial preparation of thermolysin (TL) for the standard curve as the sole commercial source of neutral protease was not suitably pure for use. The limit of quantification (LOQ) for the assay is 0.0625 AU/mL (0.01866 AU/mg TL). Only the Mustang Q Filtrate contained quantifiable levels of neutral protease activity. All sample types further downstream were below the LOQ of the assay. The data for the three manufacturing lots tested are presented below in Table 20.

TABLE 20

| Neutral Protease Activity of *C. histolyticum* Product Streams by Fluorescence Microplate Assay | | | |
| --- | --- | --- | --- |
| Sample | Lot 0009749 | Lot 0010987 | Lot 0011338 |
| Mustang Q Filtrate | 0.77 AU/mg | 1.13 AU/mg | 0.96 AU/mg |
| HIC Eluate | <LOQ | <LOQ | <LOQ |
| TFF-1 Concentrate | <LOQ | <LOQ | <LOQ |
| AUX-I Pool | <LOQ | <LOQ | <LOQ |
| AUX-II Pool | <LOQ | <LOQ | <LOQ |
| AUX-I Intermediate | <LOQ | <LOQ | <LOQ |
| AUX-II Intermediate | <LOQ | <LOQ | <LOQ |
| Bulk Drug Substance | <LOQ | <LOQ | <LOQ |

B. Zymography Assay

The Zymography assay for neutral protease activity resulted in positive neutral protease band detection in all Mustang Q Filtrate samples, one lot of HIC eluate (Lot 0011338), and all TFF-1 concentrate samples. No sample types downstream of the TFF-1 concentrate exhibit neutral protease activity. The data from *C. histolyticum* lots 0009749, 0010987, and 0011338 are presented below in Table 21. Zymography gel images of lot 0010987 are presented in FIG. 40. The images are inverse Coomassie stain representations which provide improved contrast to allow for low amplitude signal detection, e.g.—neutral protease band.

TABLE 21

Qualitative Activity Results from
Neutral Protease Zymography Assay

| Sample Description | Lot 0009749 | Lot 0010987 | Lot 0011338 |
|---|---|---|---|
| Mustang Q Filtrate | Detected* (2.0 µg load; TQ = 0.163) | Detected (2.1 µg load; TQ = 0.129) | Detected (2.0 µg load; TQ = 0.168) |
| HIC Eluate | ND (4.5 µg load) | ND (4.9 µg load) | Detected (4.6 µg load; TQ = 0.004) |
| TFF-1 Concentrate | Detected (10 µg load; TQ = 0.008) | Detected (10 µg load; TQ = 0.022) | Detected (10 µg load; TQ = 0.004) |
| AUX-I Pool | ND | ND | ND |
| AUX-II Pool | ND | ND | ND |
| AUX-I Intermediate | ND | ND | ND |
| AUX-II Intermediate | ND | ND | ND |
| Drug Substance | ND | ND | ND |

ND = Not Detected; TQ = Optical Density (OD) × mm and is a measure of the area under the lane trace curve using densitometry software as described in the method.
*Total protein loads on gel and trace quantity (area under curve) from Quantity One software indicated in parentheses.

The neutral protease clearance study demonstrates that neutral protease is predominantly cleared at the HIC Chromatography step, as evident by the lack of detectable activity after the Mustang Q Filtrate sample in the microplate assay, and the low level of activity present in one of the HIC eluate samples (lot 0011338) as evaluated by the Zymography assay. The Zymography assay revealed low neutral protease activity in all three TFF-1 concentrate samples, confirming that neutral protease partially desorbs from the HIC column during the elution step, while the majority of the enzyme remains bound to the column. The lack of neutral protease activity in the two HIC eluate samples with low activity detected in the respective TFF-1 concentrates is due to the six fold concentration that occurs prior to diafiltration commencing in this unit operation. The residual neutral protease present in the TFF-1 concentrate is eliminated from the product stream during the IEX unit operation, where the neutral protease partially co-elutes with the AUX-I tail fractions (see FIG. 39). The IEX fraction purity process limits and procedural controls (auto rejection of last two AUX-I fractions, targeting equivalent mass of intermediates) exclude the tail AUX-I fractions from AUX-I pooling which removes residual neutral protease from the manufacturing process prior to generating AUX-I intermediate and drug product.

Example 5—Effect of Removing Trace Amounts of Neutral Protease

As shown in Example 4, pooling fewer $A_{280}$ collagenase peak fractions at the tail end of the collagenase peak removes most, if not all, of the trace amounts of the neutral protease as well, such that the collagenase I product created by pooling fractions of AUX I is essentially free from neutral protease. A quantitative assessment of the pooled elution fractions was performed after the IEX purification step of each collagenase to compare the effect of the improved manufacturing process to the previous manufacturing process.

Trend analysis of the relative purity and impurity levels observed in the IEX fractions provides important process performance information. One such method is described in Example 1. In this example, collagenase I and collagenase II were tested from the following lots:

TABLE 22

Lots Used in Comparing Purities and Impurities
in Collagenase I and Collagenase II Fractions

| Lot Description | Lot Number |
|---|---|
| Lots produced prior to DI 3737 (previous manufacturing process) | C50-1000357 |
| | C50-1000375 |
| | C50-1000413 |
| | C50-1000415 |
| | C50-1000416 |
| | C50-1000516 |
| | C50-1000517 |
| | C50-1000518 |
| | C50-1000519 |
| | C50-1000520 |
| | C50-1000656 |
| | C50-1000807 |
| Atypical lots affected by DI 3797 (high levels of trace amounts of zinc and nickel) | C50-1000808 |
| | C50-1000809 |
| | C50-1000810 |
| | C50-1000811 |
| Lots produced after DI 3797 (improved manufacturing process) | C50-1001031 |
| | C50-1001032 |
| | C50-1001045 |
| | C50-0005725 |
| | C50-0006126 |
| | C50-0006337 |
| | C50-0006544 |
| | C50-0006775 |
| | C50-0006955 |
| | C50-0007273 |
| | C50-0007449 |

For each manufacturing run listed in Table 22, AUX I and AUX II elution fractions were measured for purity of product and percentage of impurities as described in Example 1. The percentage of impurities in each fraction was measured both on a per-fragment basis as well as on a total impurity basis.

The percent purity and percent of each impurity affected by the atypical ammonium sulfate lot relative to the quantity of the total protein in each AUX I or AUX II elution peak were plotted using the computer program Control Charts for Individuals. Control Chart for Individuals is a statistical tool used to distinguish between results that are due to routine variation (within the control chart limits) and results that are due to exceptional variation (beyond the control chart limits). The control limits are calculated using the moving range of two successive observations to estimate the process variability. The green horizontal line in the control charts represents the average result. The red horizontal lines represent the upper and lower control chart limits calculated as $\bar{X} \pm 2.66 \times \overline{mR}$ where $\bar{X}$ is the average and $\overline{mR}$ is the average moving range.

The percent purity of the AUX-I and AUX-II product relative to the quantity of the total protein in each AUX elution peak are provided in FIG. 42 and FIG. 43. The decrease in percent purity levels of the AUX-I and AUX-II elution peaks seen in FIGS. 42 and 43 was primarily due to elevated levels of the AUX-I 90 kDa and AUX-II 96 kDa impurities as shown in FIG. 44 and FIG. 45 respectively.

The raw data for AUX I and AUX II product peak percentages in typical manufacturing runs are shown in FIGS. 46A and 46B, and the corresponding raw data for AUX I and AUX II primary impurity percentages are shown in FIGS. 46B-46D. The primary impurities are the 90 kDa and 96 kDa degradation products from collagenase I and collagenase II due to neutral protease presence in the upstream manufacturing process.

As shown in FIGS. 46A-46D, the raw data for collagenase I purified using the previous processing methods has an average purity of 94.5%+/−1.0%. The raw data for collagenase I purified using the improved processing methods has an improved average purity of 95.8%+/−1.0%. The statistically significant improvement of 0.3% for the AUX I pooling is further evidence a collagenase I product essentially free of neutral protease is generated by using the improved method of manufacture. Unsurprisingly, the purity of collagenase II (AUX-II) remains unchanged as neutral protease does not elute from the ion exchange column with AUX II. The lingering presence of the 90 kDa and 96 kDa collagenase impurity peaks in the purification product is not unexpected as even with the improved process, neutral protease remains in the earlier steps of purification even in the improved process.

The embodiments of the invention described above are intended to be merely exemplary; numerous variations and modifications will be apparent to those skilled in the art. All such variations and modifications are intended to be within the scope of the present invention as defined in any appended claims.

SEQUENCE LISTING

```
Sequence total quantity: 7
SEQ ID NO: 1              moltype =    length =
SEQUENCE: 1
000

SEQ ID NO: 2              moltype = AA   length = 532
FEATURE                   Location/Qualifiers
REGION                    1..531
                          note = Description of Unknown: nprA sequence
source                    1..532
                          mol_type = protein
                          organism = unidentified
SEQUENCE: 2
MKKKFLSFII ISAISLNISS MTVGAKQVKE IKPPKDKESI SVLKTDLEKT KNIKSNNKEG  60
DDVTKVVKSA LKEEGNLGDF KVDNKETDVK GKKHLRSQMF IDGIPVYGSQ VIIHTNKDGQ  120
VYSVNGKVDK QPKAQSFKNR VRIKDDKAIK IAEDSLGKEI KKNKNYHSES KLYLYKVNGD  180
LQPVYLVKIS STEPEASFWH MFVSAENGKI VDKYNALSCQ ATHAQVRGVN SSGEHKILNG  240
MFENGRYFLA DSTRPSNGYI LTYDANNQEY GFPGSLFSNL TGIFDSDRQK AGVDAHHNLT  300
QVYDYYKNVL NRDSFDGKGA SIISSVHVGN NLNNAFWNGR QILFGDGDGV TFSNLAKCLE  360
VTAHEFTHAV TQSTAGLEYR FQSGALNEAF SDILGIAVHS DPNDWEIGED IYTPNVAGDA  420
LRSMSNPRLY RQPDHMKDYL YWDYSMDKGG VHYNSGIPNK AAYLMGKEVG KDSMAKIYYH  480
ALVNYLTPQS TFEDARNAVV SSAIDLHGEN SKEHKLAIKS WADVGVGEEA VR            532

SEQ ID NO: 3              moltype = AA   length = 532
FEATURE                   Location/Qualifiers
source                    1..532
                          mol_type = protein
                          organism = Clostridium histolyticum
SEQUENCE: 3
MKKKFLSFII ISAISLNISS MTVGAKQVKE IKPPKDKESI SVLKTDLEKT KNIKSNNKEG  60
DDVTKVVKSA LKEEGNLGDF KVDNKETDVK GKKHLRSQMF IDGIPVYGSQ VIIHTNKDGQ  120
VYSVNGKVDK QPKAQSFKNR VRIKDDKAIK IAEDSLGKEI KKNKNYHSES KLYLYKVNGD  180
LQPVYLVKIS STEPEASFWH MFVSAENGKI VDKYNALSCQ ATHAQVRGVN SSGEHKILNG  240
MFENGRYFLA DSTRPSNGYI LTYDANNQEY GFPGSLFSNL TGIFDSDRQK AGVDAHHNLT  300
QVYDYYKNVL NRDSFDGKGA SIISSVHVGN NLNNAFWNGR QILFGDGDGV TFSNLAKCLE  360
VTAHEFTHAV TQSTAGLEYR FQSGALNEAF SDILGIAVHS DPNDWEIGED IYTPNVAGDA  420
LRSMSNPRLY RQPDHMKDYL YWDYSMDKGG VHYNSGIPNK AAYLMGKEVG KDSMAKIYYH  480
ALVNYLTPQS TFEDARNAVV SSAIDLHGEN SKEHKLAIKS WADVGVGEEA VR            532

SEQ ID NO: 4              moltype = AA   length = 1008
FEATURE                   Location/Qualifiers
source                    1..1008
                          mol_type = protein
                          organism = Clostridium histolyticum
SEQUENCE: 4
IANTNSEKYD FEYLNGLSYT ELTNLIKNIK WNQINGLFNY STGSQKFFGD KNRVQAIINA  60
LQESGRTYTA NDMKGIETFT EVLRAGFYLG YYNDGLSYLN DRNFQDKCIP AMIAIQKNPN  120
FKLGTAVQDE VITSLGKLIG NASANAEVVN NCVPVLKQFR ENLNQYAPDY VKGTAVNELI  180
KGIEFDFSGA AYEKDVKTMP WYGKIDPFIN ELKALGLYGN ITSATEWASD VGIYYLSKFG  240
LYSTNRNDIV QSLEKAVDMY KYGKIAFVAM ERITWDYDGI GSNGKKVDHD KFLDDAEKHY  300
LPKTYTFDNG TFIIRAGEKV SEEKIKRLYW ASREVKSQFH RVVGNDKALE VGNADDVLTM  360
KIFNSPEEYK FNTNINGVST DNGGLYIEPR GTFYTYERTP QQSIFSLEEL FRHEYTHYLQ  420
ARYLVDGLWG QGPFYEKNRL TWFDEGTAEF FAGSTRTSGV LPRKSILGYL AKDKVDHRYS  480
LKKTLNSGYD DSDWMFYNYG FAVAHYLYEK DMPTFIKMNK AILNTDVKSY DEIIKKLSDD  540
ANKNTEYQNH IQELADKYQG AGIPLVSDDY LKDHGYKKAS EVYSEISKAA SLTNTSVTAE  600
KSQYFNTFTL RGTYTGETSK GEFKDWDEMS KKLDGTLESL AKNSWSGYKT LTAYFTNYRV  660
```

-continued

```
TSDNKVQYDV VFHGVLTDNA DISNNKAPIA KVTGPSTGAV GRNIEFSGKD SKDEDGKIVS    720
YDWDFGDGAT SRGKNSVHAY KKTGTYNVTL KVTDDKGATA TESFTIEIKN EDTTTPITKE    780
MEPNDDIKEA NGPIVEGVTV KGDLNGSDDA DTFYFDVKED GDVTIELPYS GSSNFTWLVY    840
KEGDDQNHIA SGIDKNNSKV GTFKATKGRH YVFIYKHDSA SNISYSLNIK GLGNEKLKEK    900
ENNDSSDKAT VIPNFNTTMQ GSLLGDDSRD YYSFEVKEEG EVNIELDKKD EFGVTWTLHP    960
ESNINDRITY GQVDGNKVSN KVKLRPGKYY LLVYKYSGSG NYELRVNK               1008

SEQ ID NO: 5              moltype = AA  length = 991
FEATURE                   Location/Qualifiers
source                    1..991
                          mol_type = protein
                          organism = Clostridium histolyticum
SEQUENCE: 5
AVDKNNATAA VQNESKRYTV SYLKTLNYYD LVDLLVKTEI ENLPDLFQYS SDAKEFYGNK    60
TRMSFIMDEI GRRAPQYTEI DHKGIPTLVE VVRAGFYLGF HNKELNEINK RSFKERVIPS    120
ILAIQKNPNF KLGTEVQDKI VSATGLLAGN ETAPPEVVNN FTPIIQDCIK NMDRYALDDL    180
KSKALFNVLA APTYDITEYL RATKEKPENT PWYGKIDGFI NELKKLALYG KINDNNSWII    240
DNGIYHIAPL GKLHSNNKIG IETLTEVMKI YPYLSMQHLQ SADQIERHYD SKDAEGNKIP    300
LDKFKKEGKE KYCPKTYTFD DGKVIIKAGA RVEEEKVKRL YWASKEVNSQ FFRVYGIDKP    360
LEEGNPDDIL TMVIYNSPEE YKLNSVLYGY DTNNGGMYIE PDGTFFTYER KAEESTYTLE    420
ELFRHEYTHY LQGRYAVPGQ WGRTKLYDND RLTWYEEGGA ELFAGSTRTS GILPRKSIVS    480
NIHNTTRNNR YKLSDTVHSK YGASFEFYNY ACMFMDYMYN KDMGILNKLN DLAKNNDVDG    540
YDNYIRDLSS NHALNDKYQD HMQERIDNYE NLTVPFVADD YLVRHAYKNP NEIYSEISEV    600
AKLKDAKSEV KKSQYFSTFT LRGSYTGGAS KGKLEDQKAM NKFIDDSLKK LDTYSWSGYK    660
TLTAYFTNYK VDSSNRVTYD VVFHGYLPNE GDSKNSLPYG KINGTYKGTE KEKIKFSSEG    720
SFDPDGKIVS YEWDFGDGNK SNEENPEHSY DKVGTYTVKL KVTDDKGESS VSTTTAEIKD    780
LSENKLPVIY MHVPKSGALN QKVVFYGKGT YDPDGSIAGY QWDFGDGSDF SSEQNPSHVY    840
TKKGEYTVTL RVMDSSGQMS EKTMKIKITD PVYPIGTEKE PNNSKETASG PIVPGIPVSG    900
TIENTSDQDY FYFDVITPGE VKIDINKLGY GGATWVVYDE NNNAVSYATD DGQNLSGKFK    960
ADKPGRYYIH LYMFNGSYMP YRINIEGSVG R                                 991

SEQ ID NO: 6              moltype = AA  length = 6
FEATURE                   Location/Qualifiers
REGION                    1..6
                          note = Description of Artificial Sequence: Synthetic peptide
source                    1..6
                          mol_type = protein
                          organism = synthetic construct
SEQUENCE: 6
VKSITG                                                              6

SEQ ID NO: 7              moltype = AA  length = 6
FEATURE                   Location/Qualifiers
REGION                    1..6
                          note = Description of Artificial Sequence: Synthetic peptide
source                    1..6
                          mol_type = protein
                          organism = synthetic construct
SEQUENCE: 7
KSCQAT                                                              6
```

What is claimed:

1. A composition for purification of a collagenase, the composition comprising:
- a collagenase derived from *Clostridium histolyticum;*
- a metalloprotease derived from *Clostridium histolyticum,* wherein the metalloprotease is not a collagenase enzyme;
- ammonium sulfate;
- a zinc content of less than about 80 ppm; and
- a nickel content of less than about 2.0 ppm.

2. The composition of claim 1, wherein the collagenase comprises:
- a collagenase I enzyme;
- a collagenase II enzyme; or
- a collagenase I enzyme and a collagenase II enzyme.

3. The composition of claim 1, wherein the metalloprotease is an M4 metalloprotease.

4. The composition of claim 3, wherein the M4 metalloprotease is a neutral protease.

5. The composition of claim 1, wherein the nickel content is less than about 1.2 ppm, less than about 1.0 ppm, less than about 0.9 ppm, less than about 0.8 ppm, less than about 0.7 ppm, less than about 0.6 ppm, less than about 0.5 ppm, less than about 0.4 ppm, less than about 0.3 ppm, less than about 0.2 ppm, less than about 0.1 ppm, less than about 0.09 ppm, less than about 0.08 ppm, less than about 0.07 ppm, less than about 0.06 ppm, less than about 0.05 ppm, less than about 0.04 ppm, less than about 0.03 ppm, less than about 0.02 ppm, or less than about 0.01 ppm.

6. The composition of claim 1, wherein the zinc content is less than about 50 ppm, less than about 25 ppm, less than about 10 ppm, less than about 5 ppm, less than about 3 ppm, or less than about 1 ppm.

7. The composition of claim 1, further comprising low levels of metals selected from aluminum, arsenic, calcium, cadmium, chromium, copper, iron, magnesium, and lead.

8. The composition of claim 1, wherein the ammonium sulfate is present at a concentration of about 0.8 M to about 1.2 M.

9. The composition of claim 8, wherein the ammonium sulfate is present at a concentration of about 1 M.

10. The composition of claim 1, further comprising a protease inhibitor.

11. The composition of claim 10, wherein the protease inhibitor is leupeptin.

\* \* \* \* \*